US011136620B2

(12) United States Patent
Klapperich et al.

(10) Patent No.: US 11,136,620 B2
(45) Date of Patent: Oct. 5, 2021

(54) DETECTION DEVICE HAVING CAPTURE REGION AND DETECTION REGION

(71) Applicant: Trustees of Boston University, Boston, MA (US)

(72) Inventors: Catherine M. Klapperich, Brookline, MA (US); Natalia M. Rodriguez, West Lafayette, IN (US); Jacqueline C. Linnes, West Lafayette, IN (US)

(73) Assignee: Trustees of Boston University, Boston, MA (US)

( * ) Notice: Subject to any disclaimer, the term of this patent is extended or adjusted under 35 U.S.C. 154(b) by 229 days.

(21) Appl. No.: 16/061,129

(22) PCT Filed: Dec. 12, 2016

(86) PCT No.: PCT/US2016/066157
§ 371 (c)(1),
(2) Date: Jun. 11, 2018

(87) PCT Pub. No.: WO2017/100765
PCT Pub. Date: Jun. 15, 2017

(65) Prior Publication Data
US 2019/0062820 A1    Feb. 28, 2019

Related U.S. Application Data

(60) Provisional application No. 62/266,424, filed on Dec. 11, 2015.

(51) Int. Cl.
*C12Q 1/6844*    (2018.01)
*G01N 33/558*    (2006.01)
*B01L 3/00*    (2006.01)

(52) U.S. Cl.
CPC .......... *C12Q 1/6844* (2013.01); *B01L 3/5023* (2013.01); *G01N 33/558* (2013.01);
(Continued)

(58) Field of Classification Search
CPC ..... B01L 2300/0816; B01L 2300/0825; B01L 3/5023; C12Q 1/6844; G01N 33/558
See application file for complete search history.

(56) References Cited

U.S. PATENT DOCUMENTS 5,792,943 A    8/1998 Craig
6,803,019 B1    10/2004 Bjornson et al.
(Continued)

OTHER PUBLICATIONS

Fenton et al., "Multiplex Lateral-Flow Test Strip Fabricated by Two-Dimensional Shaping," ACS Applied Materials & Interfaces, vol. 1, No. 1, pp. 124-129. (Year: 2009).*
(Continued)

*Primary Examiner* — Young J Kim
(74) *Attorney, Agent, or Firm* — Clark & Elbing LLP

(57) ABSTRACT

The invention features a fully-integrated rapid molecular diagnostic device that is low-cost, easy to manufacture, and simple to use. The device can serve as a molecular diagnostic platform for any disease, requiring little or no preparation or customization and can be made from simple materials (e.g., paper and adhesive film), making it inexpensive, portable, and disposable. The invention also provides methods of using the device for detection of one or more targets in a sample.

24 Claims, 39 Drawing Sheets
Specification includes a Sequence Listing.

(52) U.S. Cl.
CPC ............... *B01L 2300/0816* (2013.01); *B01L 2300/0825* (2013.01)

(56) References Cited

U.S. PATENT DOCUMENTS

| | | | |
|---|---|---|---|
| 6,827,906 | B1 | 12/2004 | Bjornson et al. |
| 6,841,131 | B2 | 1/2005 | Zimmermann et al. |
| 7,275,562 | B2 | 10/2007 | Barth et al. |
| 2001/0036634 | A1* | 11/2001 | Chow ............... B01L 3/5023 435/6.12 |
| 2002/0191056 | A1* | 12/2002 | Ardito ............... B41J 2/17559 347/86 |
| 2004/0110167 | A1 | 6/2004 | Gerdes et al. |
| 2005/0079104 | A1 | 4/2005 | Polwart et al. |
| 2006/0018789 | A1* | 1/2006 | LaStella ............ A61B 10/0038 422/417 |
| 2008/0038738 | A1* | 2/2008 | Weigum ............. A61B 5/0059 435/6.12 |
| 2012/0285560 | A1 | 11/2012 | Cooksey et al. |
| 2013/0247694 | A1* | 9/2013 | Chen .................. B01L 3/5055 73/864 |
| 2013/0330713 | A1 | 12/2013 | Jakubowicz et al. |
| 2015/0056687 | A1* | 2/2015 | Tyrrell ............... B01L 3/5023 435/287.2 |
| 2015/0132742 | A1 | 5/2015 | Thuo et al. |
| 2015/0167065 | A1 | 6/2015 | Nelson et al. |
| 2017/0022550 | A1* | 1/2017 | Moore ................ C12Q 1/6844 |

OTHER PUBLICATIONS

Posthuma-Trumpie et al., "Lateral flow (immunoassay: its strength, weakness, opportunities and threats. A literature survey," Anal. Bioannal. Chem., vol. 393, pp. 569-582. (Year: 2009).*

Boom et al., "Rapid and simple method for purification of nucleic acids," J Clin Microbiol. 28(3):495-503 (1990).

Cao et al., "Microfluidic chip for molecular amplification of influenza A RNA in human respiratory systems," PLoS One. 7(3): e33176 (2012) (11 pages).

Choi et al., "An integrated paper-based sample-to-answer biosensor for nucleic acid testing at the point of care," Lab Chip. 16(3):611-21 (2016).

Craw et al., "Isothermal nucleic acid amplification technologies for point-of-care diagnostics: a critical review," Lab Chip. 12(14): 2469-86 (2012).

Govindarajan et al., "A low cost point-of-care viscous sample preparation device for molecular diagnosis in the developing world; an example of microfluidic origami," Lab Chip. 12(1):174-81 (2012).

Horst et al., "A paperfluidic platform to detect *Neisseria gonorrhoeae* in clinical samples," available in PMC Sep. 25, 2018, published in final edited form as: Biomed Microdevices. 20(2): 35 (2018) (14 pages).

Huang et al., "Low cost extraction and isothermal amplification of DNA for infectious diarrhea diagnosis," PLoS One. 8(3): e60059 (2013) (10 pages).

International Search Report and Written Opinion for International Application No. PCT/US16/66157, dated Apr. 17, 2017 (15 pages).

Jangam et al., "Rapid, point-of-care extraction of human immunodeficiency virus type 1 proviral DNA from whole blood for detection by real-time PCR," J Clin Microbiol. 47(8):2363-8 (2009).

Kamachi et al., "Development and evaluation of a loop-mediated isothermal amplification method for rapid diagnosis of *Bordetella pertussis* infection," J Clin Microbiol. 44(5):1899-1902 (2006).

Kubo et al., "Development of a reverse transcription-loop-mediated isothermal amplification assay for detection of pandemic (H1N1) 2009 virus as a novel molecular method for diagnosis of pandemic influenza in resource-limited settings," J Clin Microbiol. 48(3):728-35 (2010).

Linnes et al., "Paper-based molecular diagnostic for *Chlamydia trachomatis*," available in PMC Jan. 1, 2015, published in final edited form as: RSC Adv. 4(80): 42245-51 (2014) (18 pages).

Linnes et al., "Polyethersulfone improves isothermal nucleic acid amplification compared to current paper-based diagnostics," available in PMC May 4, 2016, published in final edited form as: Biomed Microdevices. 18(2): 30 (2016) (22 pages).

Luo et al., "Visual detection of high-risk human papillomavirus genotypes 16, 18, 45, 52, and 58 by loop-mediated isothermal amplification with hydroxynaphthol blue dye," J Clin Microbiol. 49(10): 3545-50 (2011).

Notomi et al., "Loop-mediated isothermal amplification of DNA," Nucleic Acids Res. 28(12): E63 (2000) (7 pages).

Rodriguez et al., "A fully integrated paperfluidic molecular diagnostic chip for the extraction, amplification, and detection of nucleic acids from clinical samples," available in PMC Feb. 21, 2016, published in final edited form as: Lab Chip. 16(4): 753-63 (2016) (22 pages).

Rodriguez et al., "Paper-based RNA extraction, in situ isothermal amplification, and lateral flow detection for low-cost, rapid diagnosis of influenza A (H1N1) from clinical specimens," Anal Chem. 87(15):7872-9 (2015).

Rodriguez, Natalia M. Thesis: "A paper-based point-of-care molecular diagnostic platform for the developing world," Doctor of Philosophy, Boston University, 2016 (132 pages).

Van Duin et al., "Human papillomavirus 16 load in normal and abnormal cervical scrapes: an indicator of CIN II/III and viral clearance," Int J Cancer. 98(4): 590-5 (2002).

* cited by examiner

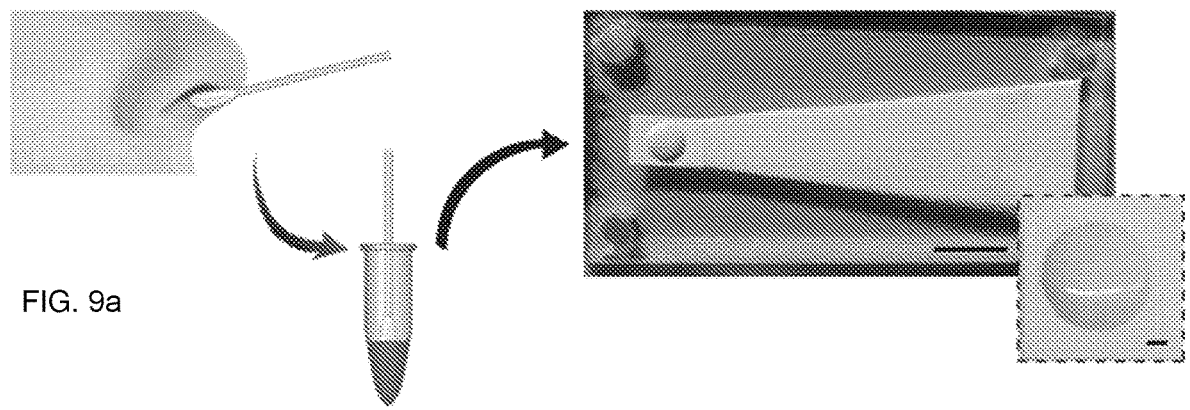
FIG. 9a
FIG. 9b
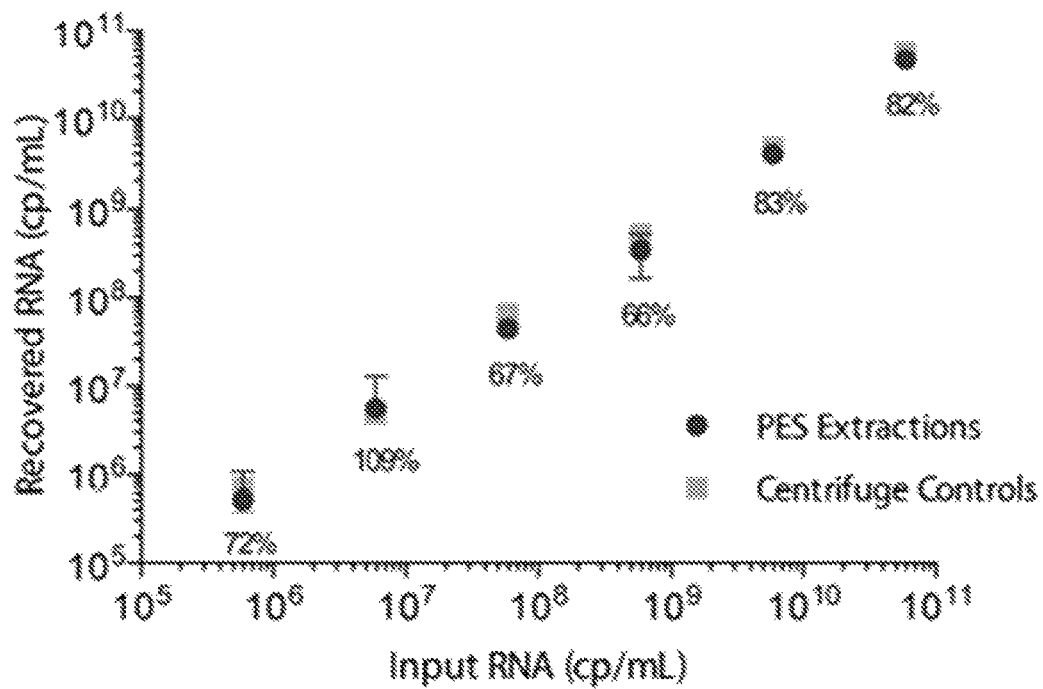

1. Extract RNA onto PES

2. Add RT-LAMP mix directly onto PES

3. Incubate in 65C heat block for 23 min

4. Elute directly onto LFS tape
PES
absorbent pad
tape
LFS tape
PES
tape
LFS tape
PES
LFS

SEQUENCE LISTING

<160> NUMBER OF SEQ ID NOS: 11

<210> SEQ ID NO 1
<211> LENGTH: 21
<212> TYPE: DNA
<213> ORGANISM: Artificial Sequence
<220> FEATURE:
<223> OTHER INFORMATION: Synthetic Construct

<400> SEQUENCE: 1
agctcagagg aggaggatga a                                            21

<210> SEQ ID NO 2
<211> LENGTH: 23
<212> TYPE: DNA
<213> ORGANISM: Artificial Sequence
<220> FEATURE:
<223> OTHER INFORMATION: Synthetic Construct

<400> SEQUENCE: 2
ggttacaata ttgtaatggg ctc                                          23

<210> SEQ ID NO 3
<211> LENGTH: 22
<212> TYPE: DNA
<213> ORGANISM: Artificial Sequence
<220> FEATURE:
<223> OTHER INFORMATION: Synthetic Construct

<400> SEQUENCE: 3
ccagctggac aagcagaacc gg                                           22

<210> SEQ ID NO 4
<211> LENGTH: 36
<212> TYPE: DNA
<213> ORGANISM: Artificial Sequence
<220> FEATURE:
<223> OTHER INFORMATION: Synthetic Construct

<400> SEQUENCE: 4
ccgaactagt atgcatggag atacacctac attgca                            36

<210> SEQ ID NO 5
<211> LENGTH: 36
<212> TYPE: DNA
<213> ORGANISM: Artificial Sequence
<220> FEATURE:
<223> OTHER INFORMATION: Synthetic Construct

<400> SEQUENCE: 5
gattgacgtc ttatggtttc tgagaacaga tggggc                            36

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
agacaactga tctctactgt t                                            21

<210> SEQ ID NO 7
<211> LENGTH: 22
<212> TYPE: DNA
<213> ORGANISM: Artificial Sequence

```
<220> FEATURE:
<223> OTHER INFORMATION: Synthetic Construct

<400> SEQUENCE: 7
cttccaaagt acgaatgtct ac                                                    22

<210> SEQ ID NO 8
<211> LENGTH: 42
<212> TYPE: DNA
<213> ORGANISM: Artificial Sequence
<220> FEATURE:
<223> OTHER INFORMATION: Synthetic Construct

<400> SEQUENCE: 8
ttctgcttgt ccagctggac gcaattaaat gacagctcag ag                              42

<210> SEQ ID NO 9
<211> LENGTH: 39
<212> TYPE: DNA
<213> ORGANISM: Artificial Sequence
<220> FEATURE:
<223> OTHER INFORMATION: Synthetic Construct

<400> SEQUENCE: 9
ccggacagag cccattacaa tgtgtgtgct ttgtacgca                                  39

<210> SEQ ID NO 10
<211> LENGTH: 19
<212> TYPE: DNA
<213> ORGANISM: Artificial Sequence
<220> FEATURE:
<223> OTHER INFORMATION: Synthetic Construct

<400> SEQUENCE: 10
catctatttc atcctcctc                                                        19

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
tgcaagtgtg actctacgct                                                       20
```

DETECTION DEVICE HAVING CAPTURE REGION AND DETECTION REGION

STATEMENT REGARDING FEDERALLY SPONSORED RESEARCH

This invention was made with Government Support under Contract Nos. AI113927, EB015403 and AI110023 awarded by the National Institutes of Health. The Government has certain rights in the invention.

BACKGROUND OF INVENTION

Infectious diseases disproportionately affect the developing world where standard molecular diagnostic approaches requiring expensive equipment, highly skilled technicians, and established laboratory and sample transportation infrastructure are unavailable. For example, cervical cancer is highly preventable and easily treated upon early detection, but over a half million new cases and over a quarter million deaths occur each year (Ferlay et al, *Int. J. Cancer,* 2010, 127:2893-2917). From a total of 528,000 new cases worldwide in 2012, 445,000 cases (84%) occurred in the developing world (Ferlay et al, *Int. J. Cancer,* 2014, 136, E359-E386), where, according to the World Health Organization (WHO), less than 5% of women have access to screening even once in their lifetime (Denny et al, *Vaccine,* 2006, 24:S71-S77).

HPV is a common sexually transmitted infection, which in the majority of cases is transient, asymptomatic, and clinically insignificant. In some women, however, the infection becomes persistent and may lead to the development of cervical cancer. Over 99% of cervical cancer cases are caused by HPV (Schiffman et al, *Lancet,* 2007, 370:890-907), more than half of which are caused by the HPV 16 subtype (Clifford et al, *Vaccine,* 2006, 24:S26-S34). Given the limitations of cytology, much work has been focused on molecular diagnostics for cervical cancer through HPV DNA testing. These methods typically have very high sensitivity (>96-100%) and specificity (>90-100%) (Ying et al, *Sci. Rep.,* 2014, 4), and are typically based on the chemiluminescent detection of RNA probes hybridizing to target DNA, like the Qiagen Digene Hybrid Capture II (HC2) test, the first HPV test approved by the FDA. This assay is performed in a laboratory with a plate reader and can take 6-7 hours. Other molecular diagnostics for HPV detection include careHPV, a lower cost version of the Digene test developed by PATH and Qiagen, Hologic's Cervista, and Roche's cobasHPV test, which use similar hybridization technology (Kuhn et al, *J. Natl. Cancer Inst.* 2000, 92, 818-825). A landmark study in rural India showed that a single round of HPV testing was associated with a significant reduction in the numbers of advanced cervical cancers and deaths from cervical cancer over time compared to cytology or VIA (Sankaranarayanan et al, *New Engl J Med,* 2009, 360, 1385-1394). While these results validate the use of HPV DNA testing, a significant drawback is the high cost and the need for sophisticated laboratory equipment. Furthermore, current HPV DNA tests still require highly trained laboratory personnel and incur turnaround times of hours to days, depending on how far the sample has to travel to a central laboratory (Villa et al, *Int. J. of Gynecology & Obstetrics,* 2006, 94, S71-S80).

Translating the molecular testing process to the point of care can minimize these limitations by providing results faster, on the order of minutes, allowing doctors to diagnose, advise and potentially treat patients in the same visit. Asymptomatic patients positive for high-risk HPV strains like 16 could be screened more closely, thus allocating precious resources to those most at risk. A point-of-care diagnostic device could be taken to remote settings beyond a standard clinic or laboratory, eliminating transport turnaround time. Additionally, a simple, user-friendly, self-contained diagnostic device, with a readout similar to an at-home pregnancy test, could reduce the need for highly trained specialists.

Integrated molecular diagnostics to enable sample-to-answer nucleic acid amplification testing (NAAT) have previously required sophisticated instrumentation to provide pressure driven fluid handling, cyclic thermal control, and optical assay detection. These requirements result in expensive equipment and costly disposables unsuitable for use in limited resource settings. Immunoassay-based rapid diagnostic tests (RDTs) offer a faster, lower-cost solution for resource-limited settings, but they suffer from low test sensitivities and specificities, commonly resulting in false negative and/or false positive detection. Thus, strategies that combine the high sensitivity and specificity of molecular diagnostics based on nucleic acid amplification with the rapid, portable, and low-cost nature of RDTs are needed to facilitate clinical care, infection control, and epidemiological investigations in these settings.

SUMMARY OF INVENTION

To address this need for easy-to-use, economical diagnostic tools, we have developed a "paperfluidic chip," i.e., a device made of inexpensive materials (e.g., paper and adhesive film) that serves as a platform combining nucleic acid extraction, amplification (e.g., isothermal loop-mediated amplification), and/or detection (e.g., lateral flow detection) via, e.g., immunochromatographic strips that enable immediate visual readout. This low-cost, portable, and disposable device provides a simple, rapid molecular diagnostic platform for point-of-care detection of nucleic acids, of any source. We developed a fully integrated, on-chip, sample-to-answer assay platform for the detection of various biomarkers directly from patient specimens in under an hour. This novel diagnostic platform could overcome many barriers associated with a variety of settings. For example, the device provides increased access to screening for diseases and early detection for patients in limited-resource settings, improving quality of life and reducing mortality from late detection. The device can be used in low-resource settings to reach patients who may otherwise go undiagnosed or be incorrectly diagnosed due to insufficient resources and personnel. In addition, the device offers an efficient alternative to conventional diagnostic procedures in the context of, e.g., over-the-counter home testing, pharmacy based testing, medical offices, field testing, or emergency rooms.

In one aspect, the invention features a detection device including a capture region for binding a target in a sample and a waste region that is connected to the capture region and that can absorb a non-target fraction of the sample. The device can further include a detection region separated from the capture region by a removable barrier (e.g., tab) that, when present, prevents transfer of liquid between the capture region and the detection region. The device can also include a non-absorbent housing that prevents moisture transfer (e.g., evaporation, leakage, or transfer between other device components (e.g., between the detection region and the capture region). The capture region typically includes a porous membrane (e.g., polyethersulfone (PES), glass fiber, cellulose paper, polycarbonate membrane, or other polymer or natural material-based porous membrane).

In some embodiments, the housing of the device can include a film (e.g., an adhesive film). In some embodiments, the film can include the removable tab separating the detection region from the capture region. In some embodiments, the film is perforated for tearing or folding. In some embodiments, the waste region can be disconnected from the capture region by tearing (e.g., along one or more of the perforations). In some embodiments, the removable tab can similarly be disconnected from the device by tearing, e.g., as part of the removal of the waste region or by folding at the perforation to disrupt contact between the capture region and the waste region. In some embodiments, the device also includes a protective flap (e.g., as part of the film) that can be folded onto the capture region to prevent moisture loss (e.g., by evaporation or leakage). In some embodiments, the film is cut from a single planar sheet. In some embodiments, the detection region and capture region are housed in separate plastic casings that can be moved in and out of contact with each other by turning, sliding, or "clicking" the plastic housings into place.

In some embodiments, the waste region is made of a material (e.g., an absorbent material, e.g., an absorbent pad including cellulose).

In some embodiments, the detection region includes a lateral flow detection strip and/or one or more detection probes. The detection region can also include one or more visible particles (e.g., nanoparticles, e.g., gold nanoparticles) or detection antibodies. The detection region can also include fluorescent or luminescent tags that could be read using known methods (e.g., fluorescence or luminescence readers). Additionally or alternatively, the detection region includes magnetic tags (e.g., magnetic tags that can be read electronically). The detection region can also include electrochemically active tags.

In some embodiments, a portion of the housing in contact with the capture region includes cyclo olefin polymer (COP). In some embodiments, the portion of the housing in contact with the capture region is made of acrylic. In some embodiments, the portion of the housing in contact with the capture region is made of polystyrene film. In some embodiments, a transfer layer, e.g., blotting paper, is sandwiched between the capture region and the waste region, the transfer layer configured to wick fluid from the capture region into the waste region.

The device may also include a heating element (e.g., a heat block, a battery-powered heater, a thin-film heater, a Peltier device, a disposable exothermic heat pack, or a pack of phase change material (e.g., phase change material that may be activated by water or another liquid reagent) and/or a cooling element (e.g., a disposable endothermic cold pack or a Peltier device).

In another aspect, the invention provides a device including a polyethersulfone (PES) membrane and a detection region connectable to the membrane.

In a related aspect, the invention includes a method for detecting the presence or absence of at least one target in a sample using a device described herein. In some embodiments, the method includes providing a device described herein and applying a sample to the capture region (e.g., a capture region made from PES). The sample can include the target and a non-target fraction (e.g., carrier liquid). Upon application of the sample to the capture region, the target binds to the capture region and the non-target fraction passes into the waste region, e.g., by wicking. In some embodiments, the target is eluted from the capture region to the detection region (e.g., by one or more applications of an elution buffer), and the presence or absence of the target is detected in a detection region. In some embodiments, the target is a nucleic acid.

In some embodiments, a removable tab is disconnected to allow liquid to flow from the capture region to the detection region during elution.

In some embodiments, the method includes isothermal nucleic acid amplification (e.g., loop-mediated isothermal amplification (LAMP), helicase dependent amplification (HDA), rolling circle amplification (RCA), multiple displacement amplification (MDA), recombinase polymerase amplification (RPA), or nucleic acid sequence base amplification (NASBA). In some embodiments, the capture region is impregnated with one or more nucleic acid amplification reagents, e.g., for isothermal amplification. Alternatively, nucleic acid amplification reagents, e.g., for isothermal amplification, are added after sample capture. In some embodiments, the method includes heating the capture region (e.g., to a temperature between about 30° C. and 80° C., e.g., about 30° C., 35° C., 40° C., 45° C., 50° C., 55° C., 60° C., 65° C., 70° C., 75° C., or 80° C.). In some embodiments, the method includes a heating element (e.g., a heat block, a battery-powered heater, a thin-film heater, or a disposable exothermic heat pack).

In another aspect, the invention features a method of constructing the device described herein. In some embodiments, the method includes providing a capture region, a waste region, and a detection region, and folding a thin sheet to cover more than 50% (e.g., about 60%, 70%, 80%, 90%, or 100%) of the surface area of the detection region to produce the housing.

In another aspect, the invention features a detection device comprising a planar reaction chamber having a front face and a back face; and a PES membrane held within the reaction chamber. The PES membrane can be accessible from the front face and the back face of the reaction chamber. In some embodiments, the reaction chamber is made wholly or partially of COP.

Definitions

As used herein, "about" means±10% of the recited quantity.

As used herein, a "detection probe" refers to any agent (e.g., covalently bound to or non-covalently associated with the detection region) that indicates the presence or absence of the target. For example, a detection probe can preferentially bind to the target, e.g., as the target enters the detection region. Binding can be direct or indirect (e.g., through intermediate binding molecules). For example, a streptavidin-coated gold-nanoparticle within the detection region that can bind a biotin-labeled target (e.g., a target bound to a biotin-labeled primer) is a detection probe. An additional detection probe can be an antibody associated with a position along the length of the detection region that binds the nanoparticle to form a visible antibody-nanoparticle-target complex. A detection probe can also be an agent that changes color or fluoresces or luminesces in response to the presence of the target. A detection probe can also be an agent that responds electrochemically to the presence of the target.

As used herein, "nucleic acid" refers to a single nucleic acid molecule (e.g., DNA, RNA, or mixture thereof), whether single stranded or double stranded. A nucleic acid can be synthetic, natural, endogenous to a subject, or exogenous (e.g., associated with an infectious agent, e.g., a virus, or cancerous cell). Nucleic acids may be further chemical modified, e.g., by moieties bound to primers used in amplification.

As used herein, "sample" refers to a liquid solution, dispersion, or combination thereof including biological material. A sample can include, e.g., exogenous buffering agents, lytic agents, proteases, nucleases, bacteria, viruses, prions, or small molecule metabolites. A sample can be derived from a dried specimen, pellet, or precipitate (e.g., by reconstitution to a liquid phase) or thawed from a frozen specimen. A sample can be biological fluid (e.g., blood, plasma, serum, urine, mucous, or sap) or a derivative thereof, a tissue sample (e.g., plant or animal), or an environmental or industrial sample.

As used herein, a "subject" refers to an organism, e.g., a plant or an animal, e.g., a mammal, e.g., a human.

As used herein, a "tab" refers to a substantially planar structure that can be physically manipulated by a user. A "removable tab" refers to a tab that can be removed from an initial position within a device. For example, a removable tab can be wholly removed from the device (e.g., cut or torn from the device) or can be removed from contact with a portion of the device (e.g., by removal from contact with one or more elements of the device). In some instances, removal of a tab is necessary and/or sufficient, e.g., to bring a capture region into contact with a detection region.

As used herein, a "target" refers to a nucleic acid, protein, or other molecule of interest that may be present in a sample. A target can be associated with a disease or disorder (e.g., genetic disease, cancer, or infectious disease, e.g., human papilloma virus (HPV), *Trypanosoma cruzi*, diphtheria toxin, *Plasmodium falciparum*, *Haemophilus ducreyi*, and other pathogens), a contaminant (e.g., of food, water, or plants), or any biomarker. In particular, any amplifiable nucleic acid detectable can be a target of the invention.

As used herein, "planar" refers to an object with a maximum length along one dimension measuring less than 20% of its length at its other two dimensions, wherein the three dimensions are orthogonal.

BRIEF DESCRIPTION OF THE DRAWINGS

FIGS. 9a-9b: Paper-based Extraction of Influenza A (H1N1) RNA. (a) Schematic of the paper RNA extraction method. Nasopharyngeal swab samples are lysed in a Glycoblue-containing lysis buffer and filtered through a paper extraction set up (scale bar=10 mm). Co-precipitated RNA and Glycoblue result in a visible blue film (inset, scale bar=1 mm). (b) Paper extractions of H1N1 RNA standards and centrifuge control extraction yields quantified via qRT-PCR. Error bars: standard deviation, n=3. Percentage values indicate paper extraction yields compared to centrifuge control yields.

DETAILED DESCRIPTION OF THE INVENTION

Figure 1:
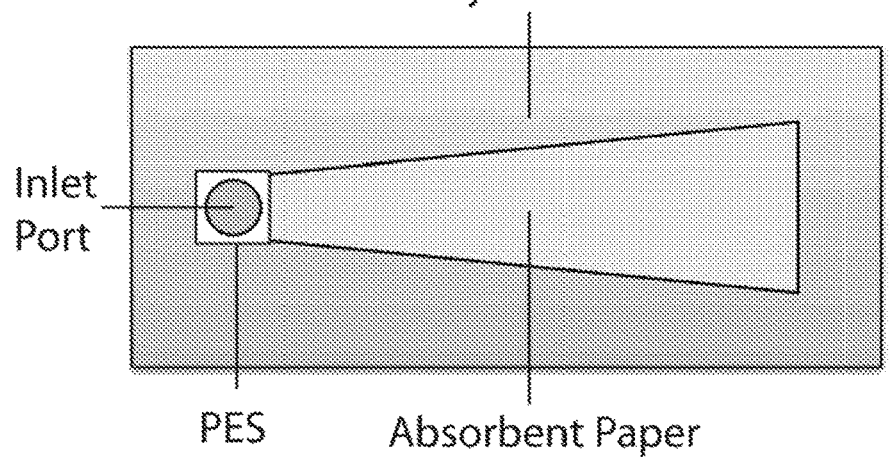
FIG. 1: Acrylic and paper extraction setup.
Figure 1:
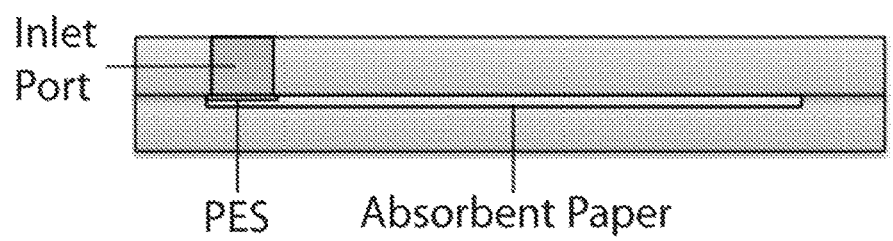
Figure 1:
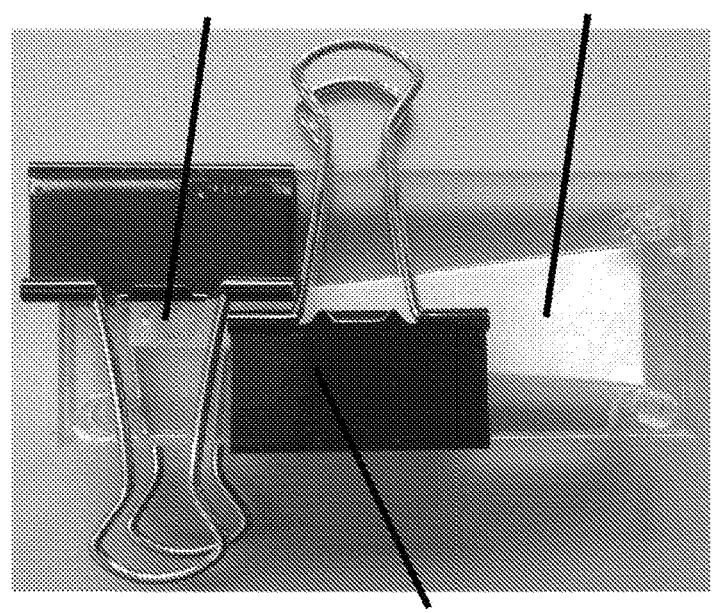

The invention provides a fully-integrated rapid molecular diagnostic device that is low-cost, easy to manufacture, and simple to use. The device addresses the limitations of current molecular diagnostic techniques by allowing for rapid (e.g., in less than 120 minutes, 90 minutes, 60 minutes, 50 minutes, 40 minutes, 30 minutes, 20 minutes, or 10 minutes), point-of-care detection (e.g., without the need for transportation to/from a laboratory). Additionally, the device can serve as a molecular diagnostic platform for any disease, requiring little or no preparation or customization (e.g., it may only require changing the primer sequences and corresponding optimization of assay conditions, e.g., isothermal nucleic acid amplification such as LAMP or HDA). The device can be made from simple materials (e.g., paper and adhesive film), making it inexpensive, portable, and disposable. The invention also provides methods of using the device for detection of one or more targets in a sample.

Device

The invention features a device (i.e., a chip) having a capture region, a waste region, a detection region, and a housing. The capture region, which can bind a target in a sample, is connected to a waste region, which can absorb a non-target fraction of the sample (e.g., a liquid phase, e.g., patient serum, buffer, etc.). The capture region is separated from a detection region by a removable tab that prevents liquid transfer from the capture region to the detection region. Removal of this tab by a user can initiate liquid transfer from the capture region to the detection region (e.g., to actuate the detection process). The device further includes a non-absorbent housing that prevents moisture transfer or loss.

The invention also features a device including a polyethersulfone (PES) membrane and a detection region connectable to the membrane. Specifically, PES (e.g., cationic PES) membranes having suitable porosity and hydrophilicity, as described in Example 2, are effective substrates for nucleic acid amplification. This property is due to the ability of PES to efficiently adsorb nucleic acid, immobilizing it within its matrix structure while enabling diffusion of necessary amplification compounds. Therefore, a PES capture region can efficiently retain a target nucleic acid as the non-target fraction of the sample is wicked into the waste region. Such devices may also include a waste region and non-absorbent housing as described. Connections between the PES membrane and detection (and optional waste region) may be as described herein. For this device, any waste region may also be disconnected from the PES membrane by other than folding or tearing.

A device can be configured specifically for a single assay by, e.g., containing detection probes that are specific to a target of interest. Additionally or alternatively, the material of the capture region can be made of materials having optimal properties to bind a specific target (e.g., optimal surface chemistry to promote adsorption of a given target or to reduce adsorption of a known non-target component). In a device containing nucleic acid amplification reagents within the capture region, these reagents can be customized to the intended target.

Alternatively, the device can be configured to test for a panel of multiple targets, e.g., by including a plurality of different detection probes that manifest as distinguishable signals (e.g., visibly different colors, different fluorescence emissions, or different binding locations on a detection region). It will be understood that various properties of the device can be adapted to enable detection and/or amplification of various targets. An exemplary multi-target device and exemplary method of use is provided, e.g., in Example 8.

Capture Region

The devices of the invention features a capture region that acts as a substrate to bind a target (e.g., a nucleic acid) in a sample. The capture region can be an absorbent (e.g., hydrophilic) material, such as a biocompatible or bioinert paper, PES, polycarbonate, cellulose, nitrocellulose, glass fiber, or glass fiber fusion papers), to facilitate holding a sufficient volume of sample. In particular, absorbent materials that can effectively bind nucleic acid (e.g., PES and cellulose-based papers) are useful as part of a device for analyzing a sample for the presence or absence of a particular nucleic acid molecule. In particular, PES has suitable porosity, fluidic absorbancy, and hydrophilicity to facilitate adsorption and amplification of nucleic acids.

The capture region can be impregnated with additional agents to enhance the sensitivity, specificity, or efficiency of detection. For example, the additional agents can include reagents involved in nucleic acid amplification (e.g., polymerase chain reaction or isothermal nucleic acid amplification, e.g., LAMP, reverse-transcription LAMP (RT-LAMP), helicase dependent amplification (HDA), rolling circle amplification (RCA), multiple displacement amplification (MDA), recombinase polymerase amplification (RPA), or nucleic acid sequence based amplification (NASBA)). Nucleic acids (e.g., primers), polymerases, or a combination thereof can all be impregnated into the capture region according to methods known in the art.

Other agents that can be impregnated into the capture region are enzyme inhibitors (e.g., nuclease inhibitors, e.g., DNAse or RNAse), buffer salts, labels (e.g., that covalently or non-covalently bind to a target), and lytic agents. Lytic agents can lyse cells and viruses that may be present in a sample, which can dramatically increase assay sensitivity by exposing intracellular molecules (e.g., nucleic acids) for detection by the device. Whatman FTA® paper, which contains a proprietary blend of lytic reagents, is suitable for this purpose.

A capture region impregnated with such reagents can facilitate immediate amplification of a target (e.g., a nucleic acid target) within its matrix at the time the sample is applied and the reagents are dispersed or solubilized in a liquid phase.

The capture region can be impregnated with agents by coating (e.g., non-covalently) on the outside of the fibers or encapsulation within the fiber structure (e.g., to provide sustained release of the agents into the pores of the capture region, e.g., covalently or non-covalently attached to the fiber material). Techniques for impregnating substrates with such agents are known in the art and include, e.g., pre-soaking the substrate in a solution containing the agent with or without one or more additional reactants at an appropriate temperature and pH for a suitable period of time. Subsequently, the capture region can be dried prior to device assembly.

The capture region can be of a suitable size and shape to capture or amplify a sufficient number of target molecules for detection. For example, it may have a dimension (e.g., measured as length or diameter) from about 0.1 to 2 inches (e.g., about 0.1, 0.2, 0.3, 0.4, 0.5, 0.6, 0.7, 0.8, 0.9, 1.0, 1.2, 1.4, 1.6, 1.8, or 2.0 inches). The thickness of the capture region can be sufficient to allow diffusion of sample components within its three-dimensional intra-fiber network and can be from about 0.001 to 0.2 inches (e.g., about 0.001, 0.002, 0.004, 0.006, 0.008, 0.01, 0.02, 0.04, 0.06, 0.08, 0.1, or 0.2 inches). The capture region can have a pore size suitable for diffusion of the sample components and can be from about 0.01 to 100 µm (e.g., about 0.01, 0.05, 0.1, 0.2, 0.3, 0.4, 0.5, 1.0, 5.0, 10, 50, or 100 µm).

In some cases, the capture region is sized to fit within a reaction chamber, such as described in Example 4. Accordingly, the capture region (e.g., a PES sheet) can be cut in one or more dimensions to be larger than an opening of a reaction chamber (e.g., a COP reaction chamber), for example, such that the capture region can be sandwiched between two or more layers of a reaction chamber housing, thereby forming a suspended or exposed capture region within the reaction chamber. The reaction chamber may also include a well, e.g., formed from a monolithic slab of material or by stacking or folding a thin sheet to set the depth. The capture region may be placed at or near the bottom or in the middle of such a well to form a space for liquid.

In certain embodiments, the device only include a housing having a reaction chamber having a capture region as defined herein.

Waste Region

The devices of the invention features a waste region, connected to the capture region, that can absorb a non-target fraction of the sample (e.g., a liquid phase, e.g., patient serum, buffer, etc.). The waste region can be an absorbent material (e.g., a hydrophilic paper, an absorbent pad, or cellulose blotting paper) that can absorb a higher volume of liquid than the capture region. It can be the same material or a different material than the capture region, and it can have a larger volume than the capture region.

The waste region can physically contact the capture region (e.g., it can underlie all or part of the capture region, such that all or part of one side of the capture region contacts the waste region). This contact enables any unbound (e.g., liquid) component of a sample to immediately wick through the capture region into the waste region. Alternatively, the waste region can be physically separated from the capture region (e.g., by a removable tab) such that a user can remove the tab to actuate the wicking of the waste from the capture region to the waste region. In some cases, the waste region is operatively connected to capture region by a transfer region, such as a blotting paper, which can facilitate transfer, e.g., by wicking of a liquid from a capture region to the waste region.

Dynamics of transfer from the capture region to the waste region can be controlled, for example, by including openings in a housing (e.g., an adhesive film) between the waste region and the capture region.

In some instances, an opening exists in the film encasing the waste region at a point configured to contact the detection region (e.g., as a result of removing a tab or folding the capture region relative to the waste region or vice-versa). Such an opening may be covered by a transfer layer to mediate fluid transport, such as a blotting paper.

Figure 30:
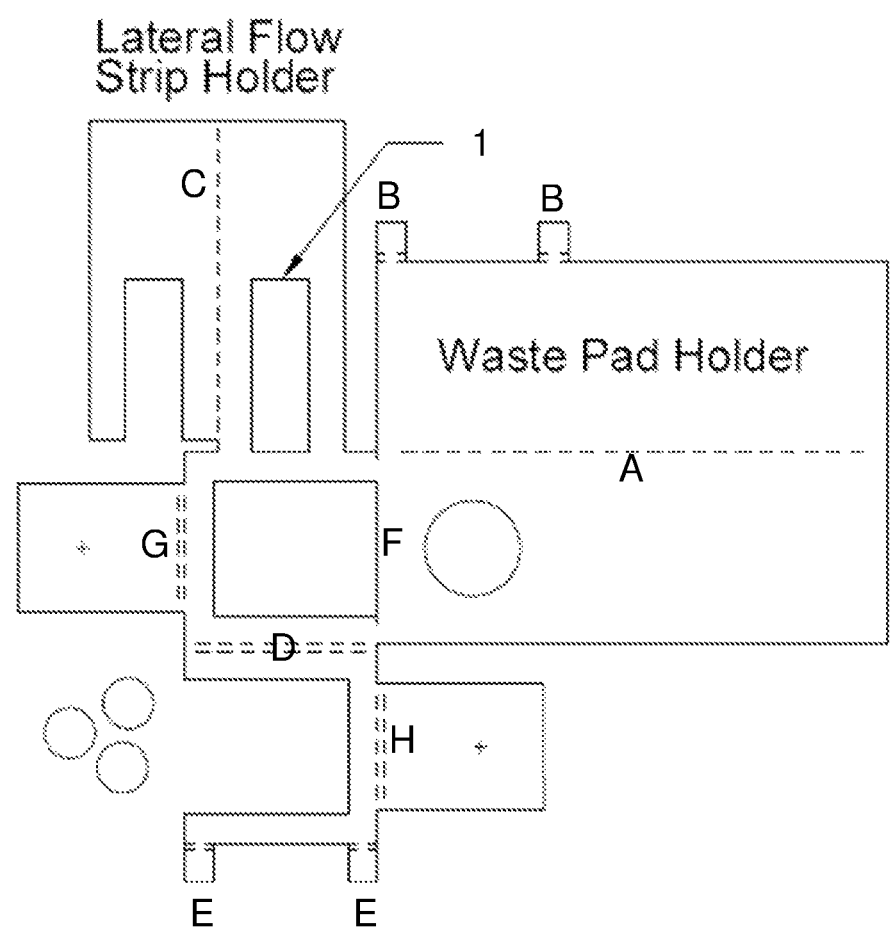
FIG. 30: Scheme for a cutout of a further embodiment of an adhesive film housing including an integrated waste pad holder, including enlarged openings to the waste pad and to the LFD. (1) Edge of the LFS waste pad sits here. (A-H) Points of folding according to the method set forth in Example 7.

The transfer from the capture region to the waste region may also be effected by including cut-outs in the housing (e.g., film), for example, around a portion of the waste region. An exemplary housing configuration is shown in FIG. 30. Such cut-outs can ensure that liquid flows within the waste region (e.g., through a waste pad), rather than around the waste pad (e.g., through a space along the outside of the waste pad, between the layers of the adhesive film). Additionally or alternatively, a housing can be designed to have hydrophilic and hydrophobic regions arranged to facilitate efficient liquid transfer.

Additionally or alternatively, the geometry of the waste region can be designed to maximize wicking of waste away from the capture region. For example, the width of a waste region can increase along its length as it progresses radially outward from the capture region to facilitate efficient wicking from the capture region. The angle given by the change in width can be selected to achieve an optimal flow rate from capture region to waste region (e.g., to maintain a constant flow rate).

Detection Region

The device of the invention also features a detection region that can indicate the presence or absence of a target in the sample. The detection region can be separated from the capture region by a removable tab. When present, the tab prevents transfer of liquid from the capture region to the detection region. Thus, the detection region can remain isolated from the sample (e.g., a crude sample and/or an amplified sample, e.g., amplified nucleic acid) until the non-target fraction (e.g., the waste) is wicked away from the target and capture region. A user can actuate the detection process by removing the tab (e.g., by folding the tab away from the interface between the capture region and the detection region, or by tearing the tab from the chip), allowing access of the target to the detection region.

The detection region can be a lateral flow detection (LFD) strip or a similar device. Various LFD strips are known in the art and are commercially available (e.g., from Ustar Biotechnologies). An LFD strip can include one or more detection probes encapsulated within the length of the strip at distinct segments to indicate the presence or absence of a bound target. For example, LFD strips can include particles (e.g., gold nanoparticles) coated with binding agents, e.g., streptavidin, oligonucleotides, or antibodies. Streptavidin-coated gold nanoparticles can bind biotin-labeled primers that have been incorporated into amplified target nucleic acid, e.g., in the capture region during amplification. The resulting nanoparticle-primer-target can then aggregate at a test line on the LFD strip (e.g., by antibody immobilized on the detection strip), generating a visible signal (i.e., a line visible by the naked eye). It is also possible for LFD strips to be read using associated instrumentation for semi-quantitative results. As a positive control, a line of biotin can bind excess streptavidin-coated nanoparticles, creating a visible signal indicating that the flow strip worked properly.

The detection region of the invention is not limited to LFD-based detection. Various alternative methods to detect or quantify a target in a detection region are known in the art. A detection region can include various substrate materials (e.g., paper, PES, polycarbonate, cellulose, nitrocellulose, glass fiber, or glass fiber fusion papers) and various detection probes. A detection probe can be any agent that indicates the presence of a target upon exposure to the target (e.g., by changing color, acquiring or changing fluorescent or luminescent properties, or otherwise visually indicating the presence of the target). Examples include antibodies (e.g., fluorescent antibodies, primary/secondary antibody systems), enzyme-substrate systems, and nucleic acid hybridization systems.

Detection regions configured for nucleic acid detection and/or amplification can also feature fluorescent detection probes, such as conventionally used real-time amplification techniques (e.g., SybrGreen or ethidium bromide intercalation). Colorimetric probes (e.g., hydroxynaphthol blue) are also suitable for, e.g., devices featuring LAMP.

Detection may also be electrochemical. For example, the detection region may include electrodes for detection of redox active targets or targets labeled with a redox active probe.

In certain embodiments, the detection region is arranged to contact the opposite face of the capture region compared to the water region. The detection region may be separated from the capture region by a lid or tab or folded out of the way until needed.

Housing

The device of the invention also features a non-absorbent housing that prevents moisture loss (e.g., by evaporation or leakage from the device or a component thereof. The housing can be a film (i.e., a thin, pliable, sheet-like material). The film can be adhesive to create a tight barrier along the surface of inner device components (e.g., the capture region, waste region, or detection region) or to promote structural integrity relative to adjacent housing components. The film can be cut from a single, planar sheet and constructed (e.g., by folding) to enclose the all or portions of the internal components (e.g., the capture region, detection region, and/or the waste region), e.g., using adhesives, fusing, or clamping.

In some cases, the housing includes two types of material (e.g., two types of film). For instance, one type of film may be used to encase the capture region (e.g., as a reaction chamber). Such a film can be a suitable material for a chemical and/or biological reaction to occur (e.g., a LAMP or HDA reaction). Suitable materials compatible with isothermal reactions include, e.g., COP. Thus, in some embodiments, a housing includes COP, e.g., as a reaction chamber in which a LAMP or HDA reaction can occur. A reaction chamber can be made from a film, such as a COP film, e.g., by a series of folds or stacking. For example, a series of accordion folds can generate a stack of film layers (e.g., a stack of square film layers with an internal void, or any other suitable shape), creating a reaction chamber having a desired depth (e.g., a depth suitable to substantially match the depth of the capture region and/or the volume of reagent within the capture region). Methods of manufacturing a reaction chamber (e.g., a COP reaction chamber) are described in Examples 4 and 5.

All or part of the housing can additionally or alternatively include a second film. In some embodiments, the housing includes an adhesive film (e.g., a one-sided adhesive film, such as Fellowes adhesive (e.g., Fellowes Self-adhesive sheets 3 mil cat. CRC52215)). The second film (e.g., adhesive film) can be configured to hold one or more components of the chip (e.g., one or more of the reaction chamber, capture region (e.g., PES), detection region (e.g., LFD strip), and/or waste region) in alignment. Reaction chamber lids can be made from the second film. In some embodiments, portions of the second film (e.g., the adhesive film) that may need to be reopened after initial adhesion (e.g., reaction chamber lids) are only adhered to portions of the first film (e.g., the reaction chamber), and not to the second film. This configuration helps to maintain the integrity of the adhesive film when the reaction chamber lids are opened and closed.

Additional elements of the housing, such as reaction chamber lid covers (see, e.g., element 2 of FIG. 26) can be made from adhesive film. Reaction chamber lid covers can be configured to reduce evaporation of liquid sample and/or reagent during the reaction (e.g., during one or more heating steps). Lids may also be used to ensure contact between regions during liquid transfer.

The removable tab can be part of the housing (e.g., the film), and it can be made to be removable by certain features of the film. For example, the film can be constructed to have one or more features (e.g., creases, perforations, crimps, embossments, or the like) to enable folding or tearing of desired areas, such as at the interface between the removable tab and another portion of the chip. Such features in the film can thus enable removal of the tab (e.g., for actuation of the detection process). Additionally or alternatively, perforations in the film housing can enable tearing and disconnection of the waste region from the capture region (e.g., after the waste is wicked away from the target).

In some cases, features that enable folding (e.g., creases, perforations, crimps, or embossments) are arranged to provide a defined three-dimensional shape to the chip when folded. For example, parallel creases or perforations in a film that are offset by a short distance, when each folded 90 degrees in the same direction, will form parallel films separated by a distance of about the offset distance between the creases (plus or minus approximately the thickness of the film itself). Thus, in some embodiments, one or more of the lines at which the housing (e.g., an adhesive film) is configured to be folded includes parallel creases or perforations offset by a distance suitable for the thickness of a resulting region of the chip (e.g., the capture region (e.g., the housing surrounding a reaction chamber), the waste region, or the detection region). The offset distance may be the same or different at any one or more lines of the device. In some cases, the offset distance is between 0.1 and 10 mm (e.g., between 0.5 and 2 mm or between 0.1 and 1.2 mm, e.g., 1.0 mm, 1.1 mm, 1.15 mm, 1.2 mm, 1.25 mm, 1.3 mm, or greater).

Additional or alternative features are provided by the film. For example, the film can feature one or more protective flaps to prevent moisture loss (e.g., by evaporation or leakage) from the capture region (e.g., during target binding or amplification). The protective flap can be folded onto an exposed region of the capture region (e.g., by folding along a perforation). Additionally, the protective flap can be integrated with the removable tab, such that the removal of the tab can be performed by first opening the flap to expose the capture region, followed by pulling the flap away from the device to remove the tab (e.g., by folding or by tearing along a perforation).

Figure 28:
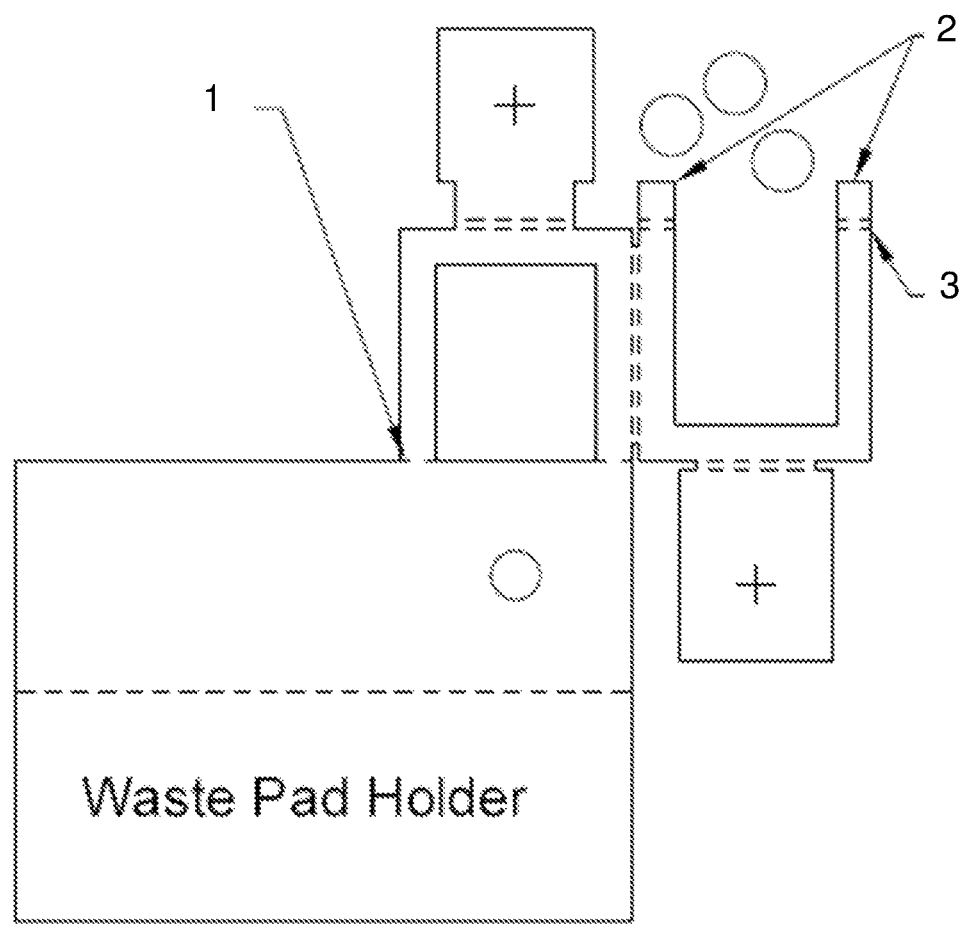
FIG. 28: Scheme for a cutout of another embodiment of an adhesive film housing including an integrated waste pad holder, including perforations for easy removal. (1) Perforations along this line allow easy removal of the waste pad from the rest of the adhesive components. (2) Adhesive flaps that secure the waste pad in the appropriate position. When COP-PES is positioned, the adhesive on these flaps faces upward and can be folded over onto the waste pad. (3) Paired perforations enable adhesive flaps to (a) fold over the COP-PES component easily and (b) be torn off easily during waste pad removal.
Figure 29:
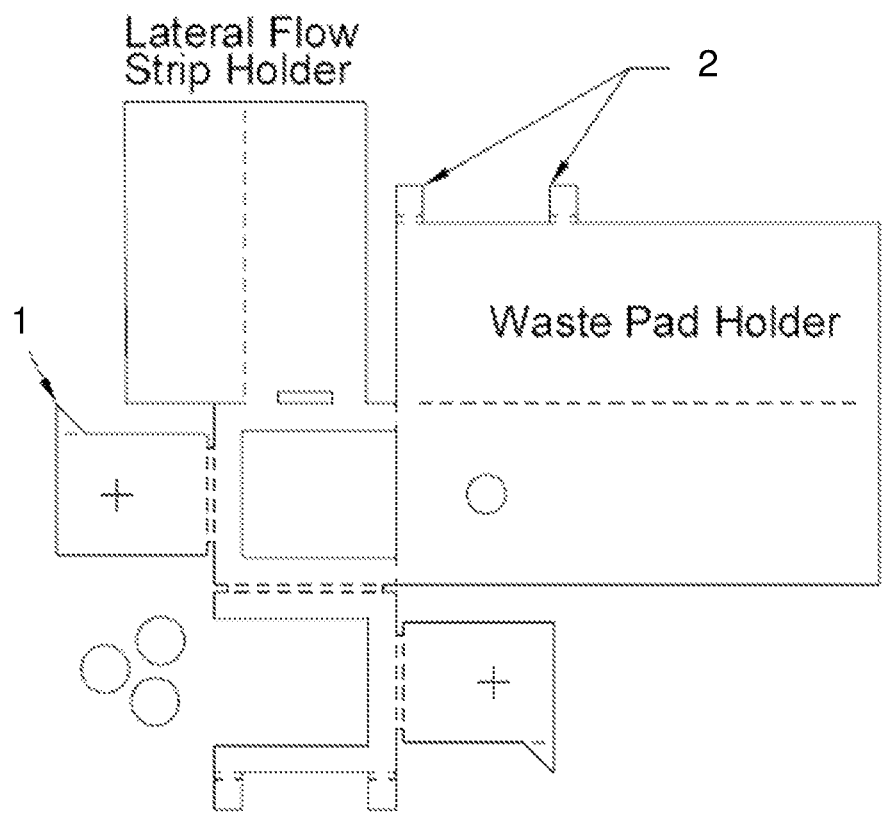
FIG. 29: Scheme for a cutout of another embodiment of an adhesive film housing including an integrated waste pad holder, including two additional flaps to secure the waste region in the correct position and additional pull-tabs on the lids. (1) This triangular flap can fold down onto the corner of the reaction chamber lid to create a pull tab such that the user can easily remove the lids following a reaction, e.g., HDA reaction. (2) Two additional flaps to secure the waste pad in the correct position

Additional features of the film include, e.g., additional adhesive flaps for stabilizing the chip in its folded position (e.g., as shown as element 2 in FIG. 28 or 29). Such flaps may bend around a folded element of the housing, for example, to prevent unfolding. In some cases, the housing includes 2 or more stabilizing adhesive flaps (e.g., 2, 3, 4, 5, 6, 7, 8, or more).

The housing can cover the internal device components in part or in whole (e.g., it can cover the waste region in whole, the detection region in whole, and the majority of the capture region except for an inlet port, where the sample can be applied). The housing can be transparent or translucent in whole or in part, such that internal components can be inspected visually (e.g., so that the detection region can be monitored).

In some embodiments of the invention, such as those shown in FIGS. 23, 24A-C, and 26-30, the housing (e.g., a film, e.g., an adhesive film) can include more than one protective flap (e.g., reaction chamber lids, e.g., 2, 3, 4, or more reaction chamber lids). In embodiments having multiple reaction chamber lids, it may be advantageous that the chip holds the detection region and the waste region in a perpendicular alignment, for example, as shown in the cutouts of FIGS. 29 and 30.

Methods

The invention features methods of using and constructing the device described above for use in diagnosing a variety of conditions (e.g., any condition characterized by the presence of abnormal biomarker for which there is a known ligand, e.g., a known nucleic acid sequence). The device can be used to detect the presence or absence of one or more targets in a sample of a subject. In particular, the invention is useful for detection of pathogens (e.g., those associated with preventable or treatable conditions. Such pathogens that can be detected using NAATs include human papillomavirus (HPV), *N. gonorrhoeae, Trypanosoma cruzi*, diphtheria toxin, *Plasmodium falciparum*, and *Haemophilus ducreyi*. Other conditions having suitable targets for the present invention are known in the art.

Using a device of the invention, a user can apply a volume of sample (e.g., from about 5 μl to about 500 μl, e.g., about 10 μl to about 100 μl, or about 25 μl to about 50 μl) to the capture region (e.g., by pipetting, dropping, or otherwise dispensing). The housing may be configured to expose a region of the capture region, forming an inlet port, indicating where the sample is to be applied. The sample may or may not include whole cells or viruses. It may be lysed prior to use in the device, or it may be lysed or partly lysed in the capture region itself (e.g., by impregnated lysis reagents as described above). Upon application of the sample to the capture region, the non-target fraction (e.g., the fluid waste) can be wicked out of the capture region into the waste region (e.g., via direction contact of the capture region to the waste region or by a transfer layer, such as a blotting paper), leaving a fraction of the sample bound within the capture region matrix. The waste may be wicked away immediately or the wicking can be actuated by removal of tab (e.g., by tearing along a perforation or by folding a tab away from the interface of the capture region with the waste region). The fraction bound within the capture region, containing the target, can be washed one or more times by applying a volume of a suitable buffer to the capture region. The wash volume can be greater than or equal to sample volume (e.g., about 1×, 2×, 4×, 6×, 8×, 10×, 20×, 50×, 100×, 500×, or 1000× the sample volume), and multiple washes can occur sequentially. The wash buffer can include ethanol (e.g., 70% or 100% ethanol). It can be removed by subsequent water washes or complete drying to prevent interference with, e.g., a LAMP reaction.

Following waste removal, the waste region may be in direct contact with the capture region and stabilized by surface tension of a layer of liquid (e.g., sample waste or wash buffer). The waste region can be disconnected from the capture region by, e.g., tearing along a perforation of the housing (e.g., the film) and pulling laterally (i.e., along the length of the capture region) to delaminate the waste region from the capture region. At this point, the waste region can be discarded or further processed. Additionally or alternatively, the waste region can be folded along a perforation of the housing to seal or remove the waste region from the capture region (e.g., to prevent fluid flow or diffusion between the capture region and the waste region). By removing or otherwise disconnecting the waste region from the capture region, a user can prevent the target from diverting from wicking into the waste region as opposed to the detection region upon elution from the capture region.

Methods of the invention include nucleic acid amplification (e.g., loop-mediated isothermal amplification (LAMP), helicase dependent amplification (HDA), rolling circle amplification (RCA), multiple displacement amplification (MDA), recombinase polymerase amplification (RPA), or nucleic acid sequence based amplification (NASBA)). Isothermal nucleic acid amplification (e.g., loop-mediated isothermal amplification) presents a convenient approach to nucleic acid amplification because it eliminates the need for thermal cycling. As such, methods including isothermal nucleic acid amplification can include heating to a constant temperature by common heating elements (e.g., heat-block, battery-powered heater, thin-film heater, or disposable exothermic heat pack, e.g., hand or toe warmer). Reaction conditions for isothermal nucleic acid amplification are known in the art. For example, the device can be heated to a temperature of between about 30° C. and 80° C. (e.g., about 30° C., 35° C., 40° C., 45° C., 50° C., 55° C., 60° C., 65° C., 70° C., 75° C., or 80° C.) for between about 1 and 60 minutes (e.g., about 1, 2, 3, 4, 5, 8, 10, 15, 20, 30, 45, or 60 minutes).

Nucleic acid amplification can occur within the capture region by, e.g., first applying the sample to the capture region, followed by applying nucleic acid amplification reagents to the capture region; first applying the nucleic acid amplification reagents to the capture region, followed by applying the sample to the capture region; applying the nucleic acid amplification reagents to the capture region at the same time as the sample; or applying the sample to a capture region that has been impregnated with all or some necessary nucleic acid amplification reagents, as described above. Alternatively, all or part of the nucleic acid amplification process can occur prior to applying the sample to the capture region.

The film housing can include one or more protective flaps (e.g., one or more adhesive film flaps) that can be folded over the capture region (e.g., over the inlet port) to prevent evaporation, e.g., during a nucleic acid amplification process.

Methods of the invention include eluting the target from the capture region to the detection region. This can be actuated by removing the tab separating the capture region from the detection region, e.g., by pulling a handle on the tab to tear at a perforation on the film. In some cases, the protective flap can double as the handle for the removable tab, such that lifting the protective flap from the capture region and pulling away from the device removes the tab and exposes the target to the detection region.

Once the tab is removed, the capture region is exposed to the detection region (e.g., an end of an LFD strip). An elution buffer can be applied to the capture region to elute the target from the capture region to the detection region. An elution buffer can be water or can be a solution including agents suitable to facilitate separation of the target from the capture region matrix. Such agents are known in the art and depend on both the target and the composition of the capture region.

Methods of the invention also include constructing the device of the invention. In general, the device features easy construction that can be performed ahead of time or on-site, immediately prior to use. The waste region, capture region, and detection region can be arranged along the surface of a planar housing (e.g., a film). The film can be cut in a shape enabling assembly by folding along indicated lines (e.g., perforations, embossments, or otherwise indicated). Folding the film around the device can result in the capture region, waste region, and detection region each being at least partially covered by the film (e.g., at least about 50%, 60%, 70%, 80%, 90%, or 100% surface covered by the film). The film housing can be secured by adhesion (e.g., an adhesive material on a surface of the film, or by the addition of an adhesive, e.g., cyanoacrylate) or by clamping in place.

EXAMPLES

The following examples are put forth so as to provide those of ordinary skill in the art with a description of how the compositions and methods claimed herein can be performed, made, and evaluated, and are intended to be purely exemplary of the invention and are not intended to limit the scope of what the inventor regards as the invention.

Example 1

Point of Care Nucleic Acid Amplification Testing

Nucleic acid amplification testing (NAAT) involves three main steps: (i) sample preparation, which involves sample lysis and nucleic acid extraction and purification, (ii) amplification of the extracted nucleic acids of interest to detectable copy numbers, and (iii) detection of the amplified products.

A. Sample Preparation

Sample preparation entails cell lysis and nucleic acid extraction steps, and has traditionally been a challenge in nucleic acid testing especially for POC applications because it involves lengthy, manual processes that often require expensive instrumentation, including centrifugation, extraction, and concentration of target nucleic acids to reach suitably low limits of detection. Single-step lysis, alcohol precipitation, and solid phase extraction processes known in the art utilize glycogen carrier particles to increase the effective hydrodynamic radius of precipitated nucleic acid aggregates.

Samples are mixed with a chaotropic lysis buffer containing guanidine thiocyanate to lyse cells and virions and denature and solubilize proteins. As nucleic acids (NA) are released into solution, they bind with the glycogen carrier particles to form glycogen-NA complexes. The addition of an alcohol precipitation buffer precipitates the glycogen-NA complexes while leaving denatured proteins and other impurities solubilized. The solution is then passed through a solid phase extraction column, glycogen-NA complexes get caught in the porous column, and waste flows through. Ethanol washes remove residual salts and contaminants. An air-drying step is performed to dehydrate the glycogen-NA complexes in place, stabilizing the sample for optional transport and storage, and elution of the samples from the column with nuclease-free water dissociates the complexes yielding a PCR compatible sample without the need for further purification. Sample preparation at the point of care is achieved using polymer micro-solid phase extraction columns, and DNA purification is performed using these columns in low resource settings by pressurizing extractions with, for example, a bicycle pump.

B. Amplification and Detection of Target Nucleic Acids

Amplification of nucleic acids at the point of care is a challenge because of the need for expensive equipment and electricity to achieve the thermal cycling required to melt, anneal, and extend the DNA. To overcome this barrier, successful isothermal amplification techniques are available that eliminate the need to melt DNA by taking advantage of enzymes that can either unwind the DNA strands or simply displace the strands during extension (Craw et al., *Lab Chip*, 2012; 12(14):2469). These enzymes allow the entire amplification process to occur at a single temperature, allowing for simpler heating mechanisms like battery-powered resistance heaters or a portable heating system, e.g., a system including a Styrofoam cup and an iron oxide exothermic reaction provided by inexpensive, commercially available toe-warmers, as described in Huang et al (*PLoS ONE,* 2013; 8(3):e60059).

Many of these isothermal amplification methods also allow for the use of intercalating fluorescent dyes or the incorporation of a probe into the amplified product that can then be detected downstream. For detection of amplified products at the point of care, ultraviolet light sources can be used in conjunction with a camera phone or rely on commercial lateral flow visual detection systems for probe detection.

C. NAAT Steps in Paper Matrices

Translating NAAT to a paper matrix format is the first step in developing a paperfluidic molecular diagnostic platform and a number of advances have been made in each of these individual steps.

Dried-blood spot (DBS) testing can be used to store HIV DNA on Whatman FTA filter paper for downstream HIV testing in remote settings. DNA extraction and purification via filtration through a paper matrix can also be used, according to known methods (Jangam et al., *J Clin Microbiol,* 2009; 47(8):2363-8). Methods for DNA extraction from paper extraction matrices made of compressed chromatography paper can also be used, such as those describe in Linnes et al. (*RSC Adv,* 2014; 4(80):42245-51). Further, "microfluidic origami" systems for cell lysis and DNA extraction are available (Govindarajan et al., *Lab Chip,* 2011; 12(1):174).

These extraction modules can be integrated with downstream amplification and detection steps for a 'sample-to-answer' total analysis system. The typical bind-wash-elute strategy used in DBS and paper-based extraction systems requires off-chip elution and also means that the extracted nucleic acid will be diluted prior to analysis, which may be undesirable in situations where low concentrations result in suboptimal detection sensitivities. The examples below describe methods and devices for molecular amplification of nucleic acids in a paper-based format.

Example 2

Material Characterization and Optimization

Example 2 provides a systematic comparison of various capture region materials of the invention, including physical characterizations, nucleic acid amplification efficiencies, and implications thereof.

A. Materials and Methods

Paper membranes were chosen for analysis based on their use in either cell filtration, nucleic acid capture, or current point-of-care diagnostics. Paper samples used in this study were 3MM Chr cellulose (CHR), 0.22 µm polyethersulfone (PES), 0.2 µm track etched polycarbonate (PC), 1.6 µm binder-free glass microfiber (GF), and 0.45 µm nitrocellulose (NC). CHR, GF, and NC were purchased from GE Healthcare (Pittsburgh, Pa.), catalog numbers 3MM CHR (3030861), GF/F (1825-090), and Protran BA85 (10402506), respectively. PES and PC were purchased from Millipore EMD (Billerica, Mass.), catalog numbers GPWP04700 and GTTP14250, respectively.

SEM

Scanning electron microscopy (SEM) was performed using a Zeiss Supra 55VP field emission SEM (Oberkochen, Germany) to visualize the surface morphologies of the materials. Each of the paper matrices were punched using a 2 mm biopsy punch and were gold coated in a Cressington 108 manual sputter coater (Watford, England) prior to imaging in order to prevent charging of the surface. Samples were imaged at both 1000× and 5000× magnification.

Porosity

Porosity analysis of 5000× magnification SEM images was performed via image J (NIH, Bethesda, Mass.) using the Particle Analysis feature. Briefly, the image threshold was set by eye to exclude only features on the front-most surfaces of the material while including pores and background features in the samples. The Particle Analysis was adjusted to include all pores with pixel area equal or greater than 2 pixels$^2$ (15.5 nm diameter) and circularity from 0 to 1.0 as well as including all edge boundaries. The porosity was determined as the area of the image that was included in the threshold divided by the total image area. The total number of pores per 100 µm$^2$, their size, and diameter were also included in the analysis although CHR and GF were not included in pore diameter analysis as these are made of matted fibers rather than pores.

Water Absorbency

The water absorbency of each of the five different materials (CHR, PES, PC, GF, and NC) was measured by calculating the difference in weight before and after submerging a 1 cm by 1 cm square of the material in deionized water. The materials were submerged until fully wetted and then gently blotted onto a polystyrene weight dish to remove excess liquid before weighing. Measurements were taken using five replicate samples for each paper. The average and standard deviation of the water absorbency were determined from the replicate samples. This average measurement was used to calculate the amount of liquid adsorbed into the papers during amplification of DNA from 6 cm diameter coupons, as well as calculating the area of paper material needed to absorb a full 25 µL of liquid.

DNA/RNA

Quantified genomic DNA from *Bordetella pertussis* (*B. pertussis*) strain Tahoma I was purchased from American Type Cell Culture (ATCC, Manassas, Va.). Quantified genomic DNA from *Chlamydia trachomatis* (*C. trachomatis*) strain 434 LGV II was purchased from Advanced Biotechnologies, Inc. (Eldersburg, Md.). Frozen stocks of each DNA type were aliquotted to 1.5 ng/µl and stored at −20° C. until use.

*Neisseria gonorrhoeae* strain NCTC 8375 was kindly provided by BioHelix, Inc. (Beverly, Mass.). *N. gonorrhoeae* was cultured on BD Chocolate Agar (Heidelberg, Germany) at 37° C. with 5% $CO_2$ for 48 hours. Genomic DNA was then purified from *N. gonorrhoeae* plate cultures using a QIAamp DNA Mini Kit (QIAgen Inc., Valencia, Calif.) according to the manufacturer's instructions with the following modification: DNA was eluted into nuclease-free water instead of the provided EB buffer. The concentration of the purified DNA was determined by measuring the $OD_{260}$ with a NanoDrop ND-2000c (Thermo Scientific, Waltham, Mass.). The quantity of DNA was calculated, and 100 µl aliquots of 1.8 ng/µl were made and stored at −20° C.

Influenza A (H1N1) in vitro RNA standards containing both target regions of the HA gene for the RT-LAMP and RT-PCR assays were generated by cloning the viral genomic RNA from a de-identified patient sample that tested positive for H1N1. Briefly, RNA from the patient sample was extracted via a Qiagen Viral Mini Kit and reverse-transcribed with a Superscript III cDNA synthesis kit (Life Technologies, Grand Island, N.Y.) with a gene-specific reverse primer. The target region of the HA gene from position HA_351 to HA_1735 was amplified by PCR with a Phusion High-Fidelity PCR kit (New England BioLabs, Ispwitch, Mass.), purified via a QIAgen gel extraction kit, and cloned into a pGEM-T Easy vector (Promega, Madison, Wis.). Plasmids were purified with a QIAgen Midi Prep Kit, blunt-cut linearized, and served as in vitro transcription DNA templates using a ProMega Ribomax Transcription kit. The RNA transcripts were then purified via acid phenol-chloroform extraction and ethanol precipitation. The concentration of the purified RNA was determined by measuring the $OD_{260}$ with the NanoDrop ND-2000c apparatus (Thermo Scientific, Waltham, Mass.). The target RNA copy number was calculated, and 50 µl aliquots were made and stored at −70° C.

Nucleic Acid Amplification

All amplification experiments were carried out in individual 0.2 ml reaction tubes containing CHR, PES, PC, GF, or NC. An additional positive control reaction containing DNA without paper and a negative control reaction containing master mix and nuclease-free water only were included in every experiment.

For experiments testing amplification in the presence of a paper matrix, 6 mm diameter hole punches of each paper material were used. None of the 6 mm coupons held a full 25 µl of reaction liquid. Therefore, for experiments testing amplification completely within a paper matrix, materials were cut to the appropriate size needed to absorb the 25 µL reaction based on their measured water absorbency. The sizes used for amplification within paper without excess liquid were 0.6 $cm^2$, 0.6 $cm^2$, 1.8 $cm^2$, 0.3 $cm^2$, 0.9 $cm^2$ for CHR, PES, PC, GF, and NC, respectively. Preliminary experiments were performed to adjust the primer ratios, salt, and amplification stabilization reagent concentrations as necessary to ensure the maximum amplification efficiency of each reaction in the liquid phase prior to testing amplification in the presence of the paper membranes.

Cut or hole-punched paper materials were placed into PCR strip-tubes. Five microliters of the RNA or DNA templates were pipetted directly onto each of the paper membranes. Twenty microliters of the appropriate amplification master mix were then added directly onto each of the paper surfaces. The tubes were incubated as described for each isothermal or PCR condition. Following amplification, a hole was made at the bottom of each tube using a sterile 18-gauge syringe needle. The tubes were stacked onto a clean 96-well plate and centrifuged at 2500 rpm for 1 minute to elute any liquid absorbed by the papers and collect it into the plate wells for downstream detection by gel electrophoresis and lateral flow strip as described in the Detection section. All experiments were repeated three separate times for every reaction condition.

Loop-Mediated Isothermal Amplification (LAMP)

B. pertussis was amplified using LAMP at 65° C. for 20 minutes. The reaction was carried out in a final volume of 25 µl with 5 µl of 150 pg/µl genomic DNA, 8 U large fragment Bst polymerase, 1× ThermoPol Reaction Buffer (New England Biolabs, Ipswich, Mass.), 0.8 M Betaine, 2 mM $MgSO_4$, 1 mM each dNTP, 7.5 µmol each of forward and reverse outer primers, 30 µmol each of forward and reverse loop primers, 75 µmol each of forward and reverse inner primers, and EvaGreen and ROX reference dyes for real-time quantitative analysis of positive and negative controls. Forward and reverse loop primers were tagged with 6-carboxyfluorescein (FAM) and biotin, respectively, to enable immediate downstream detection of the amplified products on lateral flow detection (LFD) strips. Primer sequences used were previously developed by Kamachi et al. (2006).

Influenza A (H1N1) virus RNA was amplified via reverse-transcription LAMP (RT-LAMP) at 65° C. for 15 minutes. The reaction was carried out in a final volume of 25 µl with 5 µl of $10^6$ copies/µL cloned H1N1 RNA, 8 U large fragment Bst 2.0 DNA polymerase and 1× Isothermal Amplification Buffer (New England Biolabs, Ipswich, Mass.), 2 U Thermoscript Reverse Transcriptase (Life Technologies, Grand Island, N.Y.), 0.8 M Betaine, 8 mM $MgSO_4$, 1 mM each dNTP, 5 µmol each of forward and reverse outer primers, 20 pmol each of forward and reverse loop primers, 40 µmol each of forward and reverse inner primers, and SybrGreen and ROX reference dyes for real-time quantitative analysis of positive and negative controls. As with B. pertussis, forward and reverse loop primers were tagged with FAM and biotin, respectively, to enable downstream detection of the amplified products on LFD strips. Primer sequences previously described by Kubo et al (J Clin Microbiol, 2010; 48(3):728-35) were used.

HDA tHDA of N. gonorrhoeae genomic DNA was performed according to the manufacturer's instructions (Quidel, San Diego, Calif.). A 20 µl master mix for tHDA was made using 90 nM forward primer tagged with a 3' biotin, 30 nM reverse primer, and 30 nM FAM labeled probe, in with 10% ficoll 400, 1 U MboI restriction enzyme, final concentration. Mastermix was added to 5 µl of N. gonorrhoeae DNA at a concentration of 180 pg/µl and overlaid with 50 µl of mineral oil. The reactions were amplified at 65° C. for 30 minutes. Biotin and FAM labelled amplicons were detected via LFD strips.

tHDA of C. trachomatis was performed at 65° C. for 30 minutes according the manufacturer's instructions (Quidel, San Diego, Calif.). The 20 µl master mix included 10% ficoll 400, 1 U Hpy188II restriction enzyme, 40 nM forward primer, 90 nM 3'-biotinylated reverse primer, 30 nM FAM labelled probe. Previously published primer and probe sequences are described in Linnes et al, RSC Adv, 2014; 4(80):42245-51. Master mix was added to 5 µl of 150 pg/µl C. trachomatis DNA. The reagents were overlaid with 50 µl of mineral oil prior to amplification. Downstream detection in LFD utilized amplicons labeled with biotin and FAM.

PCR

Real-time PCR on N. gonorrhoeae, C. trachomatis, and B. pertussis were performed using Taq DNA polymerase (New England Biosciences, Ipswich, Mass.) according to the manufacturer's protocol. PCR primers targeting C. trachomatis cryptic plasmid ORF3 gene and N. gonorrhoeae porA pseudogene were designed using PrimerQuest (IDT, Coralville, Iowa) and purchased from Integrated DNA Technologies (Coralville, Iowa). TaqMan PCR targeted B. pertussis insertion sequence IS481 as described by Reischl et al. (2001). Magnesium chloride concentrations were optimized to 3 mM final reaction concentrations for C. trachomatis and N. gonorrhoeae PCR reactions and 1 mM for B. pertussis amplification. Five microliters of appropriate DNA at 150 pg/µL were used as the template in each reaction and pipetted directly onto the paper substrates. Twenty microliters of the amplification reaction mix were then added onto to DNA. Amplification was performed on an Applied Biosystems 7500 thermal cycler (Grand Island, N.Y.). Following initial denaturation at 95° C. for 10 minutes, amplification proceeded for 35 cycles of 95° C. for 15 seconds, and 45 seconds of annealing and extension at 60° C. A final extension was performed at 72° C. for 10 minutes.

TaqMan real-time reverse-transcription-PCR was performed as described in the CDC protocol for real-time RT-PCR detection of influenza A (H1N1) virus for 35 cycles on an Applied Biosystems 7500 thermal cycler (Grand Island, N.Y.) (Influenza 2009). Briefly, five microliters of RNA at $10^6$ copies/μL was used as the template in each reaction combined with a mastermix from Invitrogen's Superscript III Platinum One-Step quantitative kit (Grand Island, N.Y.). Twenty microliters of the amplification reaction mix were then added directly to the reaction mixture.

Detection

LAMP amplification results were analyzed by 2% agarose gel electrophoresis and LFD strips (Ustar Biotechnologies, Hangzhou, China). LFD strips consist of a sample pad where the 10 μl sample is loaded, a conjugate pad that contains streptavidin-conjugated gold nanoparticles, a detection strip where the control and test lines are striped, and an absorbent pad to direct wicking. During amplification, loop primers tagged with FAM and biotin are incorporated into the amplicons, the biotin probe binds to the streptavidin conjugated beads, which can then aggregate at the test line (anti-fluorescein), forming a visible line to indicate a positive LAMP reaction. The control line (biotin) binds excess streptavidin beads, creating a visible positive control to show whether the flow strip worked properly.

tHDA amplicons were analyzed using 10% acrylamide gel electrophoresis and LFD strips. tHDA amplicons contain a biotinylated primer and FAM-labeled probe that bind to the LFD strips as described above. The PCR and RT-PCR amplification results were analyzed via 10% polyacrylamide gel electrophoresis. These did not include LFD strip analysis because biotin and FAM were not included in the primer designs.

Image Analysis and Quantification

LFD strips were imaged using either a Nikon D60 camera with F16 aperture at ⅓ second shutter speed or with an iPhone 5 camera on automatic setting. Because each strip contained an internal control line, both methods resulted in acceptable image quality and no post-processing was required for line intensity analysis. LFD test and control strip intensities were analyzed using the Gel Analysis feature in ImageJ (NIH, Bethesda, Mass.). The intensity of the control line was divided by the intensity of the test line for each LFD strip to obtain the percentage of control intensity for each sample. Unpaired, two-tailed Student's T-tests were used to determine the significance of each sample compared to the experimental negative control sample.

B. Physical Properties

SEM reveals the highly variable surface characteristics of the paper materials chosen in the study, as shown in FIGS. 3a-3j. CHR and GF have long fibrous features that are intertwined, while PES and NC include tortuous pores, and PC has short through-hole pores due to track etching. The 0.2 μm pores in the PC membrane and the regenerated NC pores are visible only at the high (5000×) magnification (FIGS. 3, h and j).

Characterization of the porous nature of the materials revealed significant differences in the materials' overall porosity and number of pores, as well as the area and diameter of these pores. As seen in Table 1, the porosity measurements of the materials indicated that the PC has substantially lower porosity than the other materials with 89% of the surface area being solid. CHR had the largest number of "pores" due to the space between individual fibrils that made up the larger fibers.

TABLE 1

Porosity of materials. Average (±standard deviation) reported for the pore area and diameter of pores in analyzed.

| | Porosity (%) | Pores per 100 μm$^2$ | Pore area (μm$^2$) | Pore diameter (μm$^2$) |
|---|---|---|---|---|
| CHR | 39 | 613 | 0.06 ± 0.86 | — |
| PES | 45 | 215 | 0.21 ± 2.16 | 0.51 ± 1.66 |
| PC | 11 | 266 | 0.04 ± 0.03 | 0.23 ± 0.20 |
| GF | 53 | 509 | 0.10 ± 0.41 | — |
| NC | 41 | 259 | 0.16 ± 0.35 | 0.45 ± 0.66 |

The fluidic absorbency of each of the five different paper materials was measured by calculating the difference in weight before and after submerging a 1 cm by 1 cm square of the material in water. The materials were submerged until fully wetted and then gently blotted onto a polystyrene weight dish to remove excess liquid before weighing. Measurements were taken using five replicate samples for each paper. The average and standard deviation of the water absorbency were calculated from the replicate samples.

All amplification experiments were carried out in individual 0.2 ml reaction tubes containing CHR, PES, PC, GF, or NC. An additional positive control reaction containing DNA without paper and a negative reaction control containing master mix and nuclease free water only were included in every experiment. For experiments testing amplification in the presence of a paper matrix, 6 mm diameter hole punches of each paper material were used. None of the 6 mm hole punches held a full 25 μl of reaction liquid. Therefore, for experiments testing amplification completely within a paper matrix, materials were cut to the appropriate size needed to absorb the 25 μL reaction based on their measured fluidic absorbency. The sizes used for amplification within paper without excess liquid were 0.6 cm$^2$, 0.6 cm$^2$, 1.8 cm$^2$, 0.3 cm$^2$, 0.9 cm$^2$ for CHR, PES, PC, GF, and NC, respectively.

Cut or hole-punched paper materials were placed into PCR strip-tubes. Five microliters of the RNA or DNA templates were pipetted directly onto each of the paper membranes. Twenty microliters of the appropriate amplification master mix were then added directly onto each of the paper surfaces. The tubes were incubated at 65° C. for the 20-min LAMP reaction. Following amplification, a hole was made at the bottom of each tube using a sterile 18-gauge syringe needle. The tubes were stacked onto a clean 96-well plate and centrifuged at 2500 rpm for 1 minute to elute any liquid absorbed by the papers and collect it into the plate wells. All experiments were repeated three separate times for every reaction condition.

Paper Extraction Setup

Figure 2:
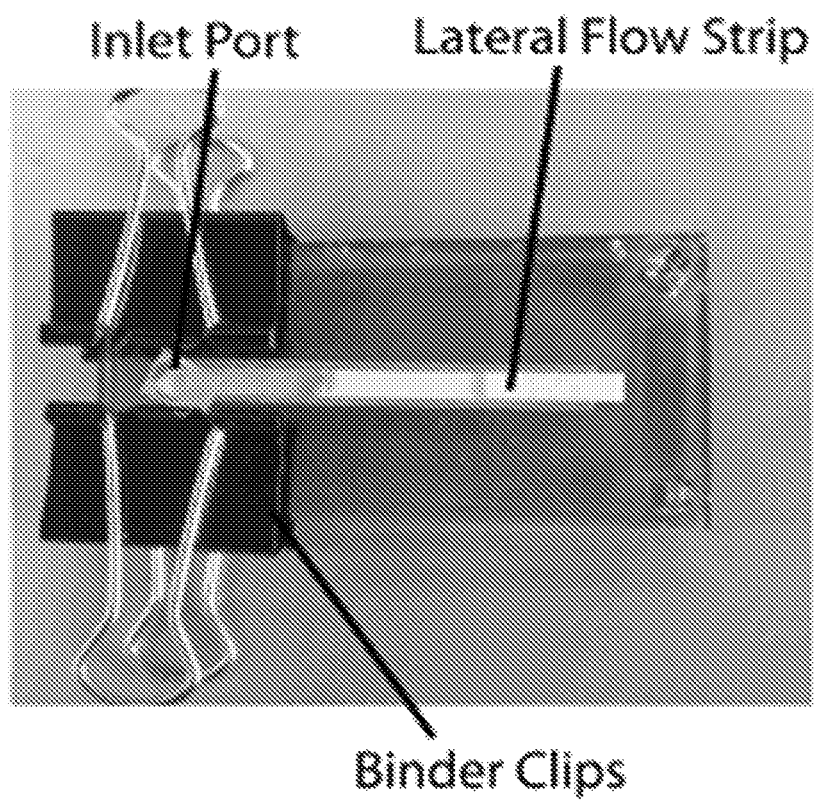
FIG. 2: Acrylic lateral flow detection elution setup.
Figures 3A, 3B, 3C, 3D, 3E, 3F, 3G, 3H, 3I, 3J:
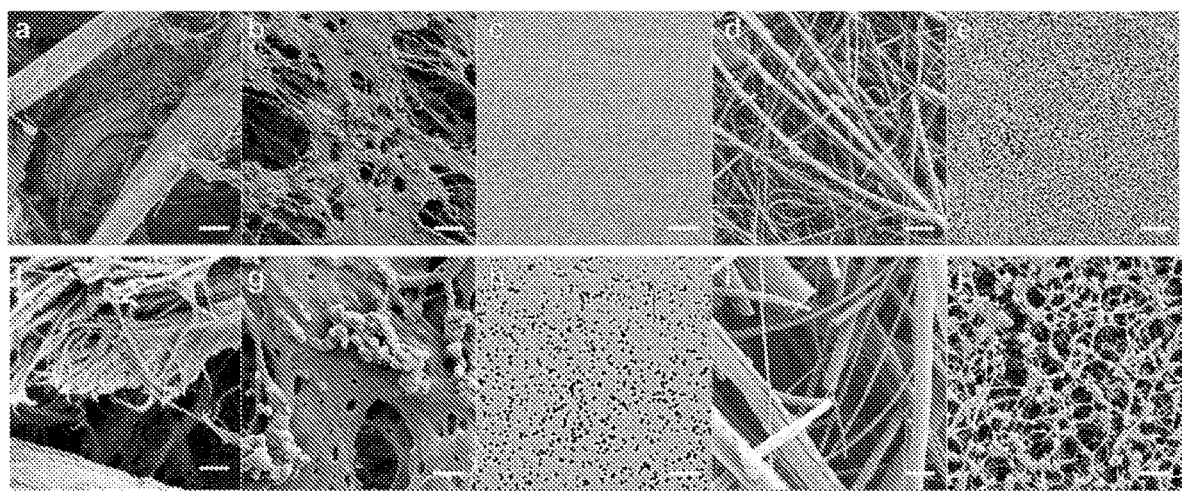
FIGS. 3a-3j: Scanning electron micrograph of Chr cellulose (CHR) (a, f), polyethersulfone (PES) (b, g), polycarbonate (PC) (c, h), glass microfiber (GF) (d, i), and nitrocellulose (NC) (e, j) at 1000× (a-e) and 5000× (f-j) magnification. Scale bars represent 10 μm (a-e) and 2 μm (f-j).

A 0.8×0.8 cm (0.64 cm$^2$) piece of polyethersulfone (PES) filter paper with a 0.2 μm pore size (Millipore, cat #GPWP04700) was placed on top of a cellulose (Whatman GB003 blotting paper, cat #10426972) absorbent pad cut to absorb approximately 400 μl of liquid waste. The absorbent pad was shaped as a 6 cm long sector that extended radially from 0.5 cm at the base of the top sheet inlet port to an ultimate width of 2 cm. This sector angle was configured to achieve the appropriate flow rate as the volume of liquid absorbed by the pad per unit time has been previously determined to be linearly related to the angle of the sector shape. The PES and absorbent pad were placed into a custom-designed 0.635×3.5×7.5 cm acrylic fixture and aligned with the inlet port in the top acrylic sheet (FIGS. 1 and 2). The fixture was designed in SolidWorks and was cut out of acrylic sheets using a 30 W Epilog Zing laser cutter (speed=5, power=100, frequency=5000). The bottom sheet was rastered (speed=100, power=60) with the same dimensions as the absorbent pad to ensure its secure placement. The extraction setup was held together using 32 mm binder clips (FIG. 2).

Paper Extraction Procedure

Based on a single-step lysis, RNA extraction, and alcohol precipitation recipe developed by Cao et al. (*PLoS ONE*, 2012; 7(3):e33176), 25 µl of the NPS specimen was mixed with 75 µl lysis buffer (2 M GuSCN, 66.7% 2-propanol, 1× RNASecure (Ambion)) and 3 µl of 15 mg/mL Glycoblue coprecipitant (Life Technologies). This mixture was pipetted onto the PES membrane through the extraction setup inlet port. The prevailing capillary forces generated by the absorbent pad quickly wick the liquid phase away from the membrane surface, thus leaving the solid phase behind. As a result, the RNA-Glycoblue precipitate remains on the PES membrane producing a visible blue film. The PES membrane was then rinsed sequentially with 200 µl of 70% ethanol and 100 µl of 100% ethanol, which were also wicked away from the inlet port by the absorbent pad. The PES membrane was physically removed from the extraction setup with forceps and placed into a 0.2 mL tube. Tubes were left open for 2 minutes to allow the PES membrane to dry.

For extraction quantification experiments, the PES membrane was placed into a 0.2 mL tube with 100 µl of nuclease-free water and vortexed to dissolve the RNAGlycoblue complexes and release the RNA into solution. The tube was inverted and a small hole was pierced through the bottom of the tube using a sterile needle (BD Ultra-Fine™ 30 Gauge Lancets, cat #325773). The tube was then stacked inside a larger 1.5 mL Eppendorf tube, and centrifuged at 2500 RPM for 1 minute to elute the extracted RNA completely out of the PES and into the Eppendorf tube for downstream qRT-PCR analysis.

Paper extractions were compared to traditional centrifugation extraction methods, where instead of capturing the RNA in paper, it was precipitated by centrifugation, and the pellet was washed and resuspended. Briefly, 25 µl RNA solutions mixed with 75 µl lysis buffer were centrifuged at 13,000 RPM for 15 minutes at room temperature until a blue pellet was visible at the bottom of the tube. The supernatant was removed, and 100 µl of 70% ethanol was added to the tube and centrifuged at 13,000 RPM for 5 minutes at room temperature. The supernatant was removed and 100 µl of 100% ethanol was added to the tube and centrifuged a final time at 13,000 RPM for 5 minutes. All centrifugation steps were performed in an Eppendorf centrifuge model 5424R. The supernatant was removed and tubes were left open for pellets to dry at room temperature on the bench top for 10 minutes. The pellets were resuspended in 100 µl nuclease-free water and RNA was quantified using qRT-PCR.

Paper Extraction and In Situ RT-LAMP Assay

For in situ RT-LAMP experiments, the sample was extracted in the paper extraction set-up as described above, and the extracted RNA precipitated onto the PES was amplified directly within the PES matrix. The 25 µl RT-LAMP reaction mix was pipetted directly onto the RNA-Glycoblue-containing 0.64 cm$^2$ PES membrane and was fully absorbed by the PES. This size of PES required to completely absorb 25 µl of liquid had been calculated using the previously determined water absorbency of PES of 38.82 µl/cm$^2$. The soaked PES was left in the 0.2 mL tube with the lid closed to prevent evaporation and incubated in a 65° C. heat block for 23 minutes. Following amplification, the soaked PES containing the entire RT-LAMP reaction volume was placed directly onto the sample pad of the LFD strip using forceps, and the LFD strip and PES were placed between two acrylic sheets aligned with the inlet port (FIG. 3) and the setup was held together with 32 mm binder clips. 50 µl of nuclease free water was then pipetted into the inlet port, filtered through the PES, and wicked onto the LFD strip for immediate detection of amplified products.

Clinical Nasopharyngeal Specimens

Nasopharyngeal swab (NPS) samples were collected during the 2009 influenza A (H1N1) pandemic period from patients at Beth Israel Deaconess Medical Center (BIDMC) during a previously described study that had been reviewed and approved by BIDMC's institutional review board. Briefly, discarded NPS specimens that had been taken during routine clinical care for testing ordered by the patient's clinician were collected and frozen. The NPS specimens were taken using two Copan flocked swabs (COPAN). The first swab was inserted flat and pushed forward with gentle downward pressure on the lower nasal floor to the posterior wall of the nasopharynx, where it was rotated for a few seconds to collect cellular material. The swab was withdrawn and placed into sterile 1× PBS. The collection procedure was repeated using the second flocked swab in the other nostril; the second swab was placed into M4RT (Remel) media for viral culture. The two swabs were then submitted on ice to the BIDMC microbiology laboratory. After routine testing, specimens (approximately 1.0 mL) were stored at −80° C. The frozen NPS specimens were later deidentified and sent to the Klapperich Laboratory, where they were aliquotted and stored at −80° C.

For gold standard extraction experiments, RNA was extracted from 140 µl of each specimen using the QIAamp Viral RNA Mini Kit (Qiagen).

H1N1 RT-LAMP Assay in Solution

Figure 4A:
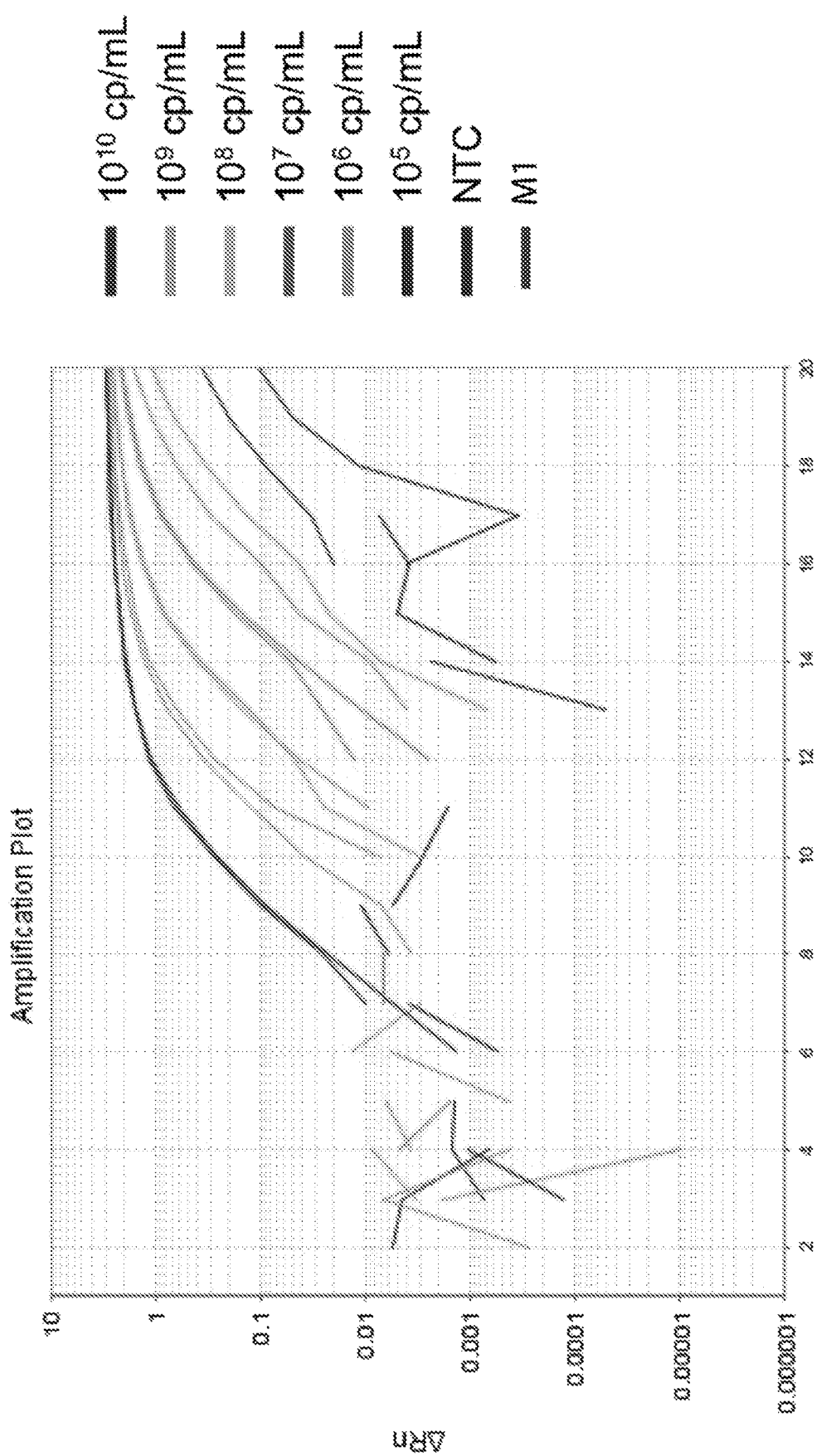
FIGS. 4a-4d: Influenza A (H1N1) RT-LAMP Assay in solution. (a) Real-time RT-LAMP amplification of in-vitro transcribed H1N1 RNA standards from $10^{10}$ cp/mL down to $10^5$ cp/mL. NTC=no template control. (b) 2% Agarose gel electrophoresis of RT-LAMP products. L=100 bp DNA ladder, $10=10^{10}$ cp/mL, $9=10^9$ cp/mL, etc. NTC=no template control. M1=M1 gene in vitro transcribed standards, $10^{10}$ cp/mL. (c) HindIII digestion of RT-LAMP products. (d) Representative lateral flow strips from three independent experiments show detection of RT-LAMP products. Top line is the flow strip control line, bottom line is test line. Test line intensity as percentage of control line intensity for three experiments is plotted ($*$ $p<0.05$, $$ $p<0.01$, $*$ $p<0.001$, ns=not significant).

Before developing the in situ amplification assay, we first optimized a protocol for RT-LAMP amplification of H1N1 RNA in solution. The H1N1 RT-LAMP assay was optimized using our in vitro transcribed H1N1 RNA standards. We set a target lower limit of detection of $10^5$ cp/mL, since the mean pre-treatment H1N1 viral load in nasal specimens has been reported to be ~$10^8$ cp/mL with typical viral loads between $10^6$ and $10^{10}$ cp/mL, and patients below $10^5$ cp/mL generally had not yet begun to exhibit symptoms. The RT-LAMP reaction incubation time at 65° C. required to reach our target lower limit of detection of $10^5$ cp/mL was determined by amplifying 10-fold serial dilutions of in vitro transcribed target RNA (from $10^{10}$ to $10^5$ cp/mL) using EvaGreen and ROX reference dyes for real-time quantification of amplification. With our final optimized assay conditions, we were able to amplify $10^5$ cp/mL (a net 500 copies per sample) to detectable levels within 20 minutes (FIG. 4a). To ensure specificity of the primers for the HA gene of the H1N1 strain, in vitro transcribed RNA from a different gene of the influenza A viral genome, the matrix protein-encoding M1 gene, was also tested at a high concentration of $10^{10}$ cp/mL. There was no amplification of the negative (NTC) control or of the M1 gene, demonstrating H1N1 strain specificity. Amplification results were confirmed by 2% agarose gel electrophoresis (FIG. 4b) and lateral flow detection (FIG. 4d).

LFD strips produced visible test lines for positive reactions, enabling immediate detection of amplified products with the naked eye. Test line intensities were quantified as a percentage of control line intensities and results from three independent experiments are plotted in FIG. 4d. Although lower in intensity, our LFD strips still exhibit a clear, visible test line down to $10^5$ cp/mL that is statistically different from the negative control.

Figures 4B, 4C:
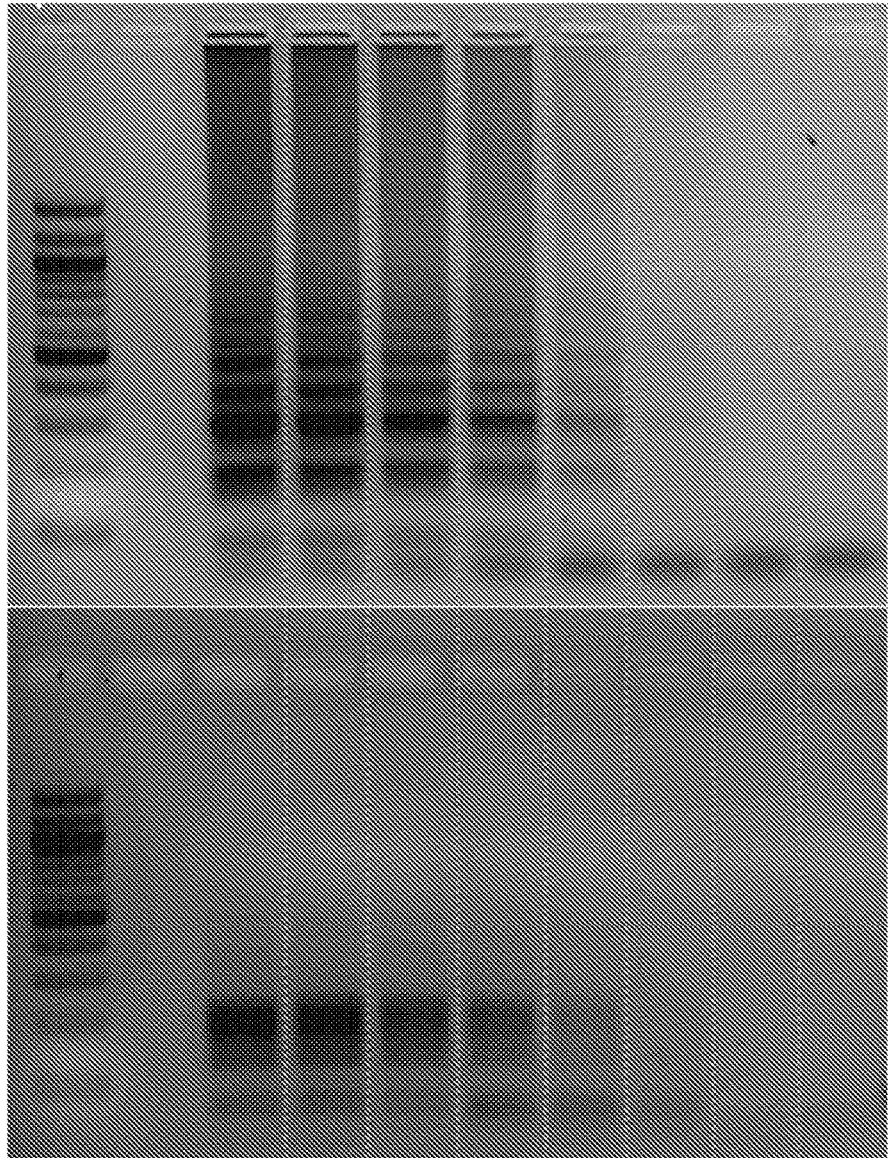
Figure 4D:
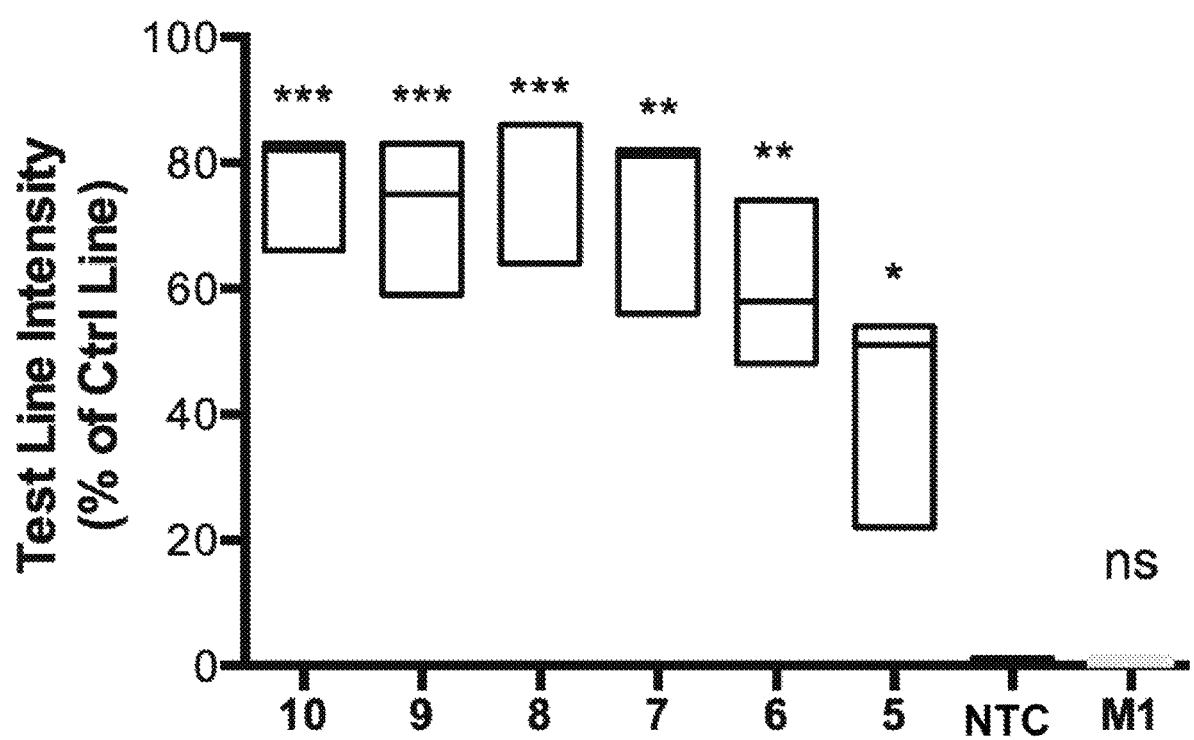
Figure 5:
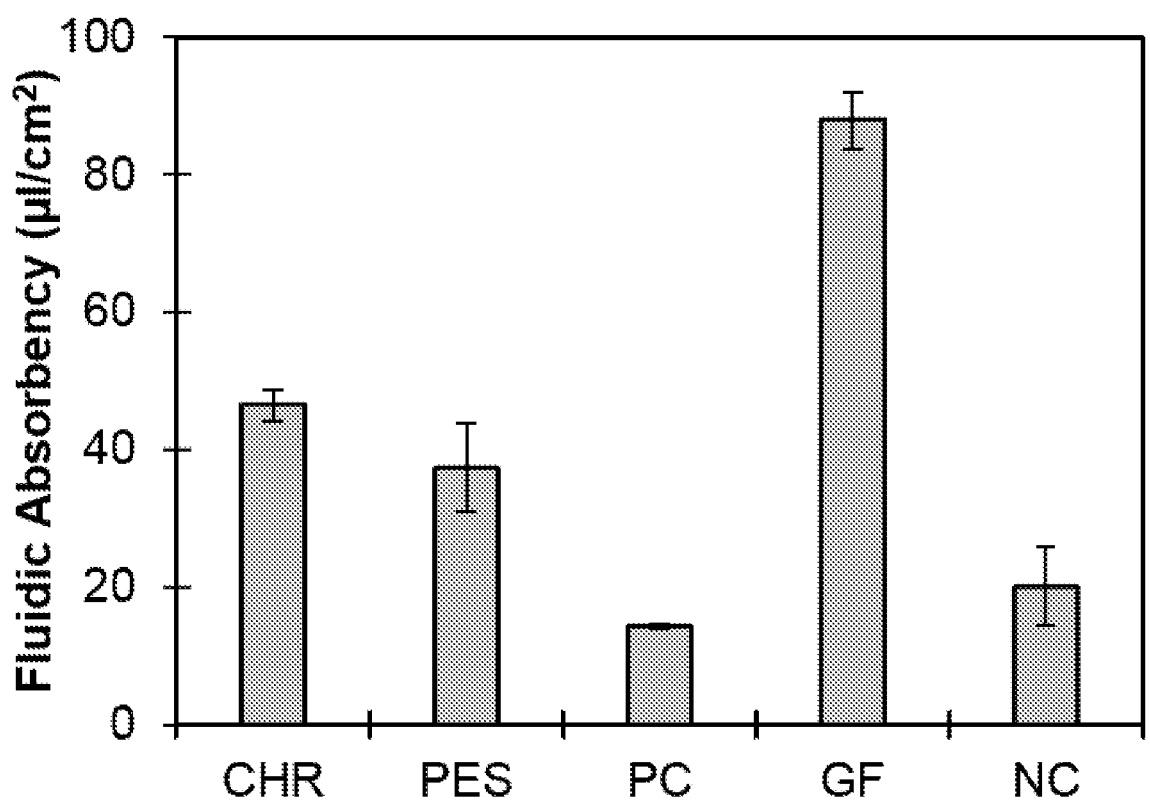
FIG. 5: Fluidic absorbency of 1 cm$^2$ materials. Average absorbency+/−standard deviations are shown (n=5 for each sample type).
Figures 6A, 6B, 6C:
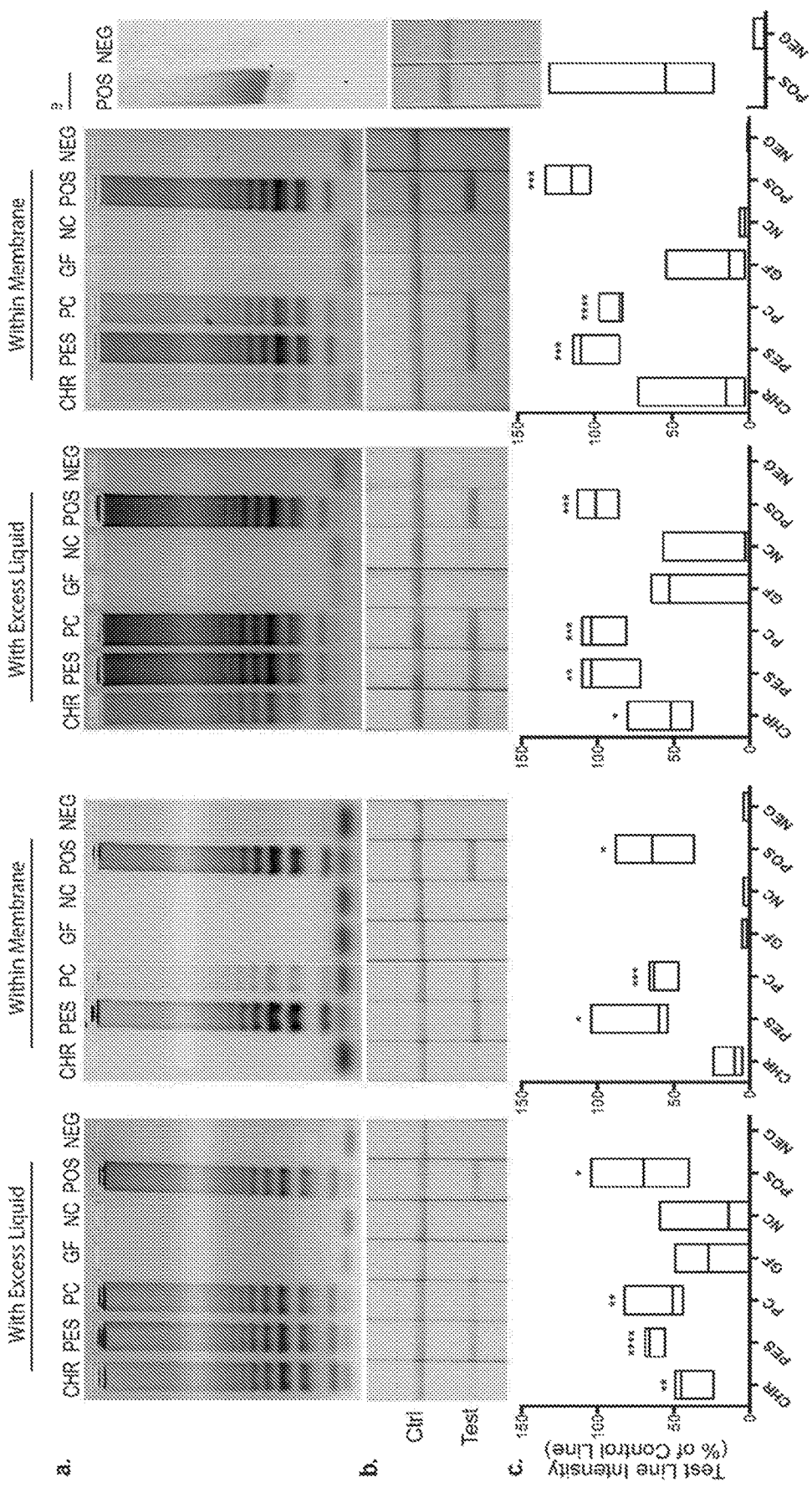
FIGS. 6a-6c: Results of LAMP performed on *B. pertussis* (Left) and Influenza A (H1N1) (Right). Detection by agarose gel electrophoresis (a) and LFD strips (b). Intensity of the LFD test line as a percentage of the control line in the strips is shown in (c) for each ($*$ $p<0.05$, $$ $p<0.01$, $*$ $p<0.001$, $****$ $p<0.0001$).
Figures 7A, 7B, 7C:
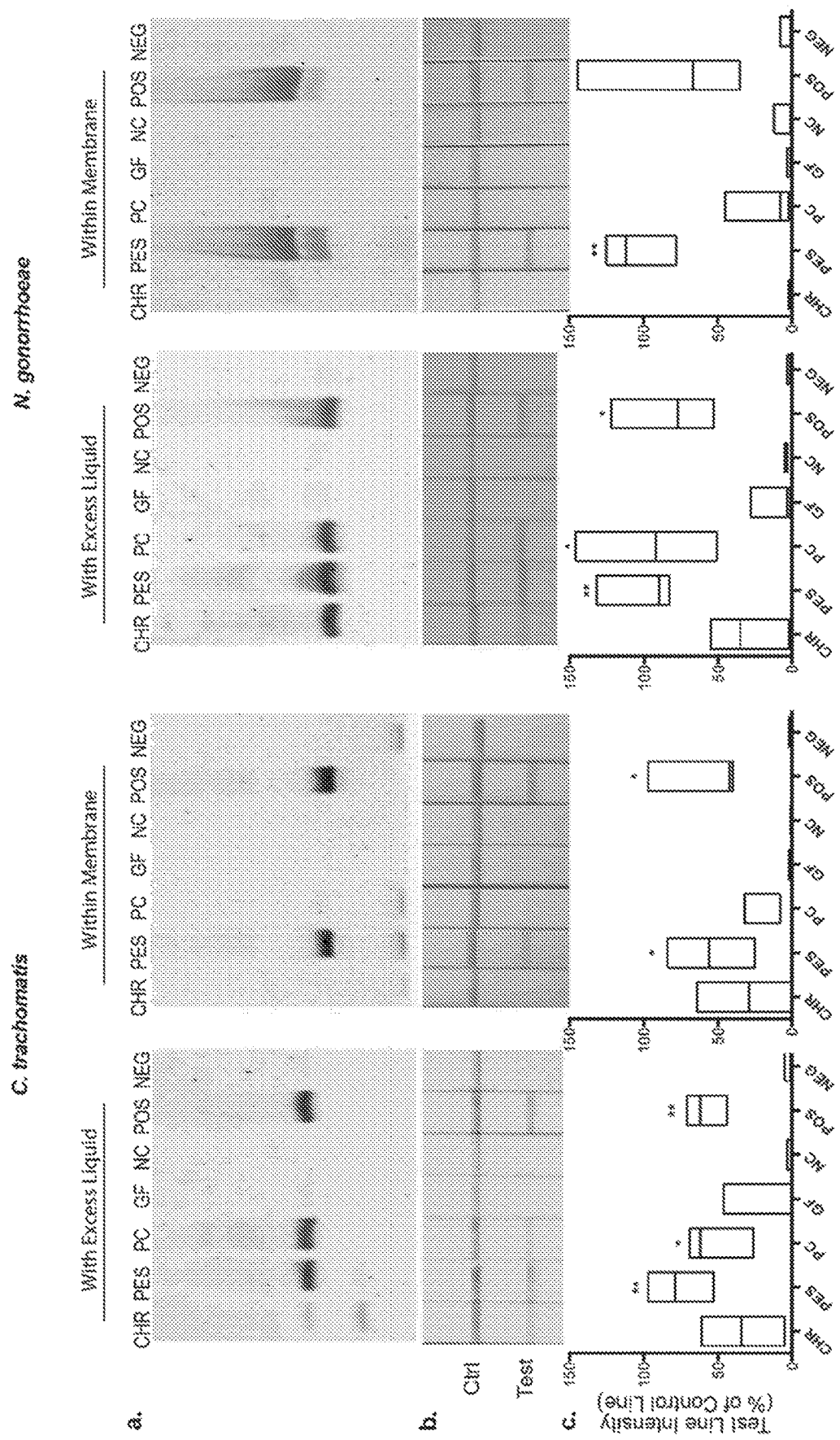
FIGS. 7a-7c: Results of helicase-dependent amplification (HDA) performed on *C. trachomatis* (Left) and *N. gonorrhoeae* (Right). Detection by agarose gel electrophoresis (a) and LFD strips (b). Intensity of the test line as a percentage of the control line in the strips is shown in (c) for each ($*$ $p<0.05$, $**$ $p<0.01$).
Figure 8:
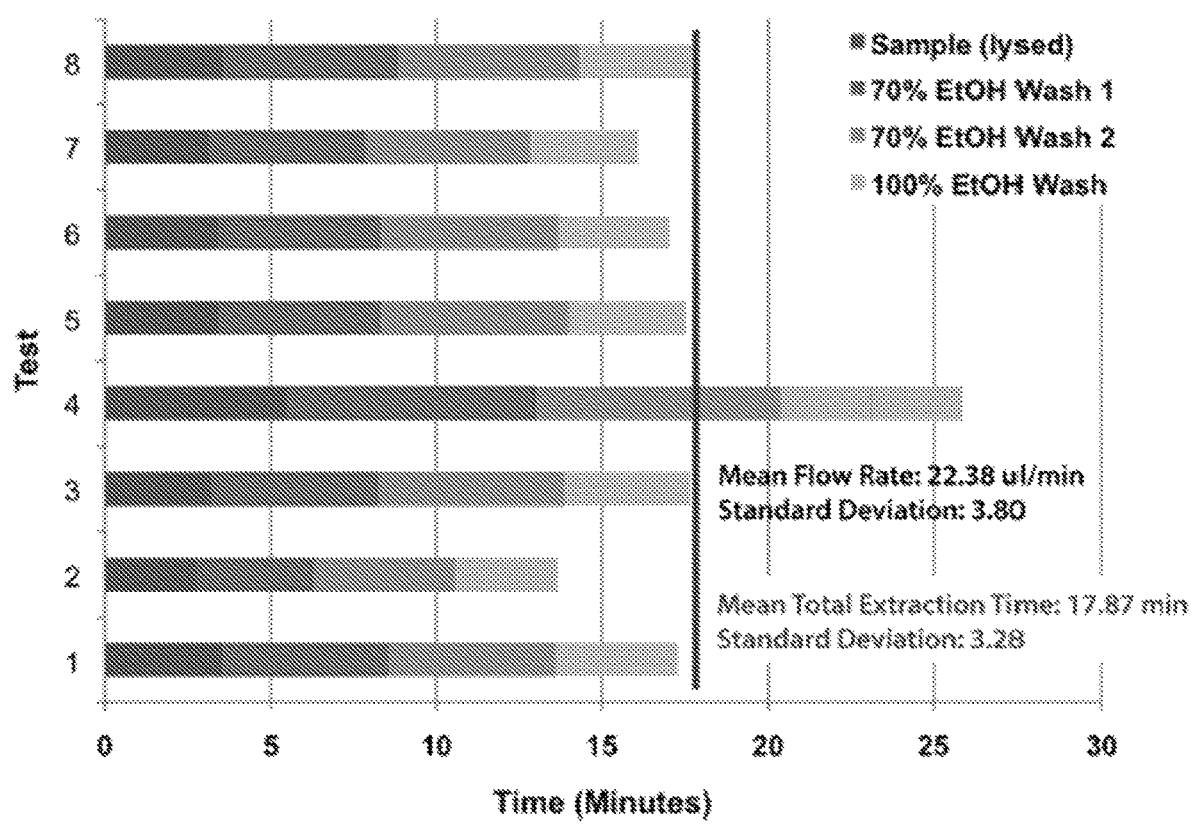
FIG. 8: Flow rates and times for extraction. Mean flow rate=22.38 μl/min, SD=3.8. Mean total extraction time=17.87 min, SD=3.28 (n=8).

Additionally, to confirm that RT-LAMP products specifically correspond to the correct H1N1 target sequence, the amplified products were digested with the HindIII restriction endonuclease and analyzed by agarose gel electrophoresis (FIG. 4*c*). The Influenza A (H1N1) HA gene sequence contains a single HindIII cutting site between the FIP and BIP regions, and digested products were in agreement with the expected sizes previously determined by Kubo et al. (*J Clin Microbiol,* 2010; 48(3):728-35), confirming the specificity of our product.

Screening Paper Materials for In Situ Amplification

The water absorbency measurements for each paper material are shown in FIG. 5. GF absorbed the most water, an average of 88 μl/$cm^2$ (±4.2 μl/$cm^2$). Despite their differing surface features, CHR and PES absorbed similar volumes of liquid and were not statistically significantly different from one another ($p>0.05$), with averages of 46 and 37 μl/$cm^2$ (±2.3 and 6.4 μl/$cm^2$, respectively). As might be expected from the minimal tortuosity and lower surface area, PC absorbed the least liquid of the sampled matrices at 14 μl/$cm^2$ (±0.4 μl/$cm^2$). However, NC, while highly porous, did not absorb significantly more liquid than the PC ($p>0.05$) at an average of 20 μl/$cm^2$ (±5.8 μl/$cm^2$).

Using these water absorbency values, the size of each paper material that was required to absorb the full volume of an amplification reaction mix (25 μl) was calculated. The CHR, PES, PC, GF, and NC were cut into the corresponding size: 0.6, 0.6, 1.8, 0.3, and 0.9 $cm^2$, respectively, in order to perform nucleic acid amplification entirely within the paper matrices without excess reaction liquid.

C. LAMP in the Presence of Membranes, With Excess Liquid

Isothermal amplification of both *B. pertussis* DNA and Influenza A (H1N1) RNA via LAMP and RT-LAMP, respectively, occurred in the presence of the 6 cm diameter hole-punched pieces of CHR, PES, and PC. Along with the positive control, amplification in these membranes was statistically significantly greater than the negative controls ($p<0.02$ for each). Amplification was inhibited by the presence of GF and NC, as determined by agarose gel electrophoresis and LFD strips, shown in FIGS. 6*a*-6*c*. In some cases, amplification of RNA or DNA was able to occur in the presence of the GF and NC, but results were inconsistent and greatly inhibited compared to other matrices.

D. LAMP Within Membranes

LAMP and RT-LAMP resulted in successful amplification of *B. pertussis* DNA and Influenza A (H1N1) RNA, respectively, when performed completely within the PES and PC matrices. PES, PC, and the positive control all resulted in statistically significant amplification compared to the negative control for both *B. pertussis* ($p<0.05$ for each) and Influenza A (H1N1) ($p<0.001$ respectively). However, the amplification was inhibited when performed within CHR, GF and NC matrices, as determined by altered band patterns in agarose gel electrophoresis and fainter test lines in the LFD strips, shown in FIGS. 6*a*-6*c*. While not statistically significantly different from the negative control, amplification did occur in experimental replicates in the presence of CHR for both *B. pertussis* DNA and Influenza A (H1N1) RNA. Additionally, faintly detectable RNA amplification occurred within the GF matrix as well, however, these were not statistically significant versus the negative control.

E. tHDA in the Presence of Membranes, With Excess Liquid tHDA amplification in the presence of PES and PC papers, as well as the positive control, resulted in statistically significantly greater amplification than the negative control ($p<0.02$ and $p<0.05$ for each membrane amplifying *C. trachomatis* and *N. gonorrhoeae*, respectively). tHDA amplification of *C. trachomatis* and *N. gonorrhoeae* DNA was inhibited by CHR, GF, and NC membranes. While CHR material allowed for DNA amplification by tHDA in all experimental trials, the amplification product was highly variable and was not significantly different from the negative controls.

F. tHDA Within Membranes tHDA within paper matrices only resulted in consistent amplification of *C. trachomatis* and *N. gonorrhoeae* DNA using the PES matrices and the positive, paper-free, controls (FIGS. 7*a*-7*c*). These two conditions were significantly different compared to the negative control when detected by LFD strips ($p<0.05$). CHR and PC membranes resulted in amplification of *C. trachomatis* DNA in some, but not all, experiments and were not statistically significant. From *N. gonorrhoeae*, PC samples also allowed for some amplification within the membrane, but this was never greater than 50% of the control intensity and was not statistically significant. While the positive controls using in the *N. gonorrhoeae* DNA consistently amplified, high variability of the detection lines (35-144% of the control lines) yielded results that were not statistically significantly different from the negative controls ($p=0.08$). PES was the only sample to result in consistent, statistically significant *N. gonorrhoeae* amplification compared to the negative control in LFD strips ($p<0.005$).

G. PCR

PCR and RT-PCR were inhibited for all DNA and RNA samples in the presence of the 6 mm hole punch papers. Only the positive, paper-free, nucleic acid controls amplified for any of the four pathogen nucleic acids tested (*B. pertussis*, Influenza A (H1N1), *C. trachomatis, N. gonorrhoeae*). PCR was also inhibited when performed within the paper matrices with no excess liquid. No DNA amplified from *B. pertussis, C. trachomatis*, or *N. gonorrhoeae* in any sample except for the positive, paper-free, controls. However, RNA from Influenza A (H1N1) did amplify when RT-PCR was performed within PES membranes without excess liquid, but not within any of the other matrices.

Paper-Based Extraction

For initial paper extraction experiments, solutions of influenza A (H1N1) RNA spiked into PBS were prepared at concentrations ranging from $10^{10}$ copies of RNA per mL (cp/mL) down to $10^5$ cp/mL, and a negative control containing no RNA. RNA solutions were mixed with the Glycoblue-containing lysis buffer, pipetted into the inlet port of the extraction set-up (FIG. 2), and filtered and washed through the paper membrane producing a visible blue film. The complete extraction procedure with PES took approximately 18 minutes. The flow rates and times for all steps are shown in FIG. 8. The extraction procedure with Polycarbonate resulted in significantly slower flow rates, and the experiment was discontinued after one hour (extraction still wasn't complete by that point), since this amount of time would be unacceptable for point-of-care applications.

The RNA precipitate was eluted from the PES matrix and recovery yields were quantified using qRT-PCR (FIG. 9). Results from triplicate paper extraction experiments show good correlation between input and recovered RNA over 5-log of concentrations ($r^2=0.9989$) with yields between 60% and 94%. Quantity values for RNA extracted through PES or via traditional centrifugation methods were compared (FIG. 9). RNA recovery yields through the PES membranes ranged from 66% to 109% of the centrifugation control yields. These results demonstrate that our paper extraction method, which is equipment-free and faster than traditional centrifugation extraction methods (~20 min versus ~35 min including drying times), results in comparable extraction yields over 5-log of RNA concentrations.

Paper Extraction and In Situ RT-LAMP Assay

Figure 10A:
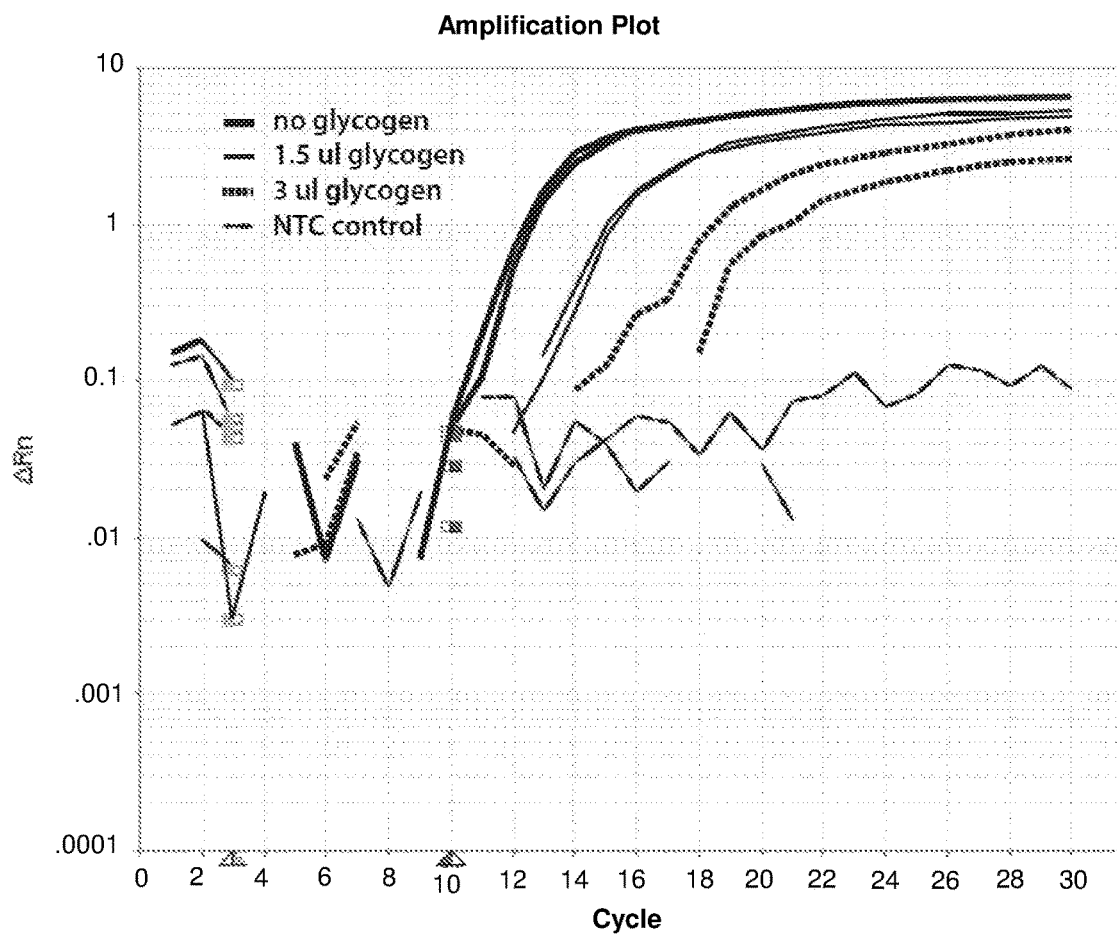
FIGS. 10a-10b: Effects of glycogen on RT-LAMP reaction. (a) Real-time RT-LAMP amplification with increasing amounts of Glycoblue causing greater delays in amplification. (b) Agarose gel electrophoresis of paper extracted RNA+RT-LAMP in situ products for 23 min at 65° C. L=100 bp DNA ladder, $10=10^{10}$ cp/mL, $9=10^9$ cp/mL, etc. NTC=no template control.
Figure 10B:
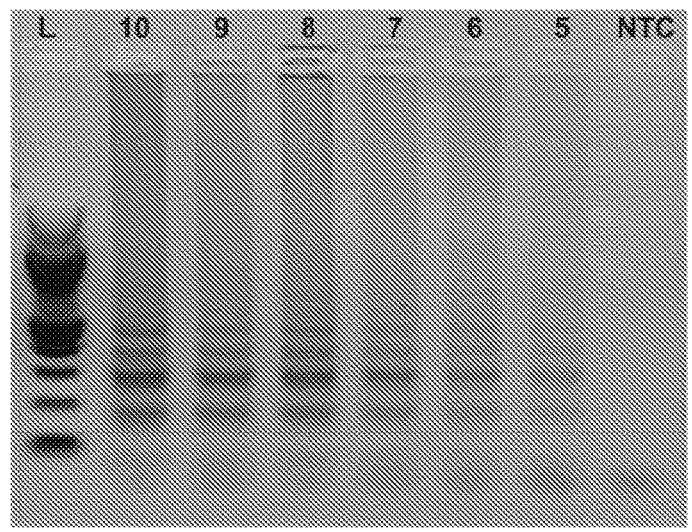
Figure 11A:
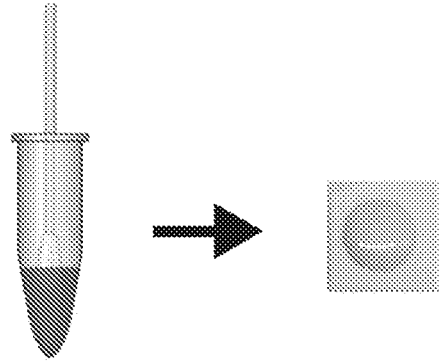
FIGS. 11a-11c: RT-LAMP in situ with in-vitro transcribed H1N1 RNA standards. (a) Method scheme of paper RNA extraction followed by in situ RT-LAMP and immediate downstream lateral flow detection. (b) Representative lateral flow detection strips. $10=10^{10}$ cp/mL, etc. NTC=no template control. (c) Lateral flow detection strip test line intensities from three independent experiments are plotted as a percentage of control line intensities ($*$ $p<0.05$, $$ $p<0.01$, $*$ $p<0.001$, ns=not significant).
Figure 11A:
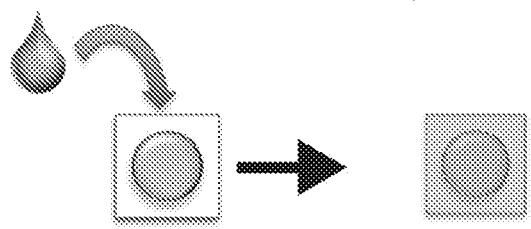
Figure 11A:
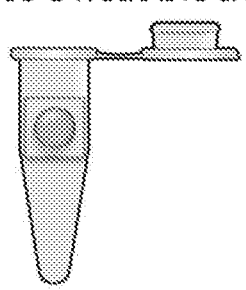
Figure 11A:
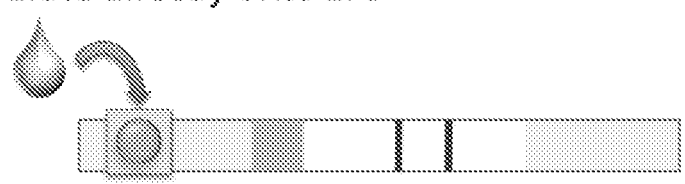

Having previously demonstrated that LAMP reactions are not inhibited in the presence of PES, and can even take place completely within a PES matrix, we next asked whether in situ amplification of the freshly-extracted RNA was possible within the same PES matrix. An optimized protocol for amplification in solution (FIG. 4) served as a starting point for optimizing the paper-based RT-LAMP assay. Optimization experiments revealed that a higher $MgSO_4$ concentration of 11 mM improved RT-LAMP performance in situ. All other assay reagent concentrations remained the same as the in solution reaction mix. As shown in FIG. 11a, once the RNA was extracted onto the PES membrane, the 25 µl RT-LAMP reaction mix was added directly onto the RNA containing PES, and the full reaction volume was completely absorbed by the membrane. The soaked PES was then placed inside a 0.2 mL tube to prevent evaporation, and incubated in a 65° C. heat block for 23 minutes. During preliminary RT-LAMP in situ experiments, we found that the Glycoblue that co-precipitates with the RNA onto the PES caused a slight inhibition of the amplification (FIG. 10a), and after careful optimization we determined that 23 minutes was the ideal reaction time for RT-LAMP in situ (FIG. 10b). After the 65° C. incubation, the soaked PES was then placed directly onto a lateral flow strip and 50 µl water was slowly dropped onto the PES to elute the amplified product onto the detection strip. In order to ensure that the water filtered through the PES before reaching the lateral flow strip, the PES and strip were placed between two acrylic sheets aligned with an inlet port, similar to the extraction set-up, except the lateral flow strip replaces the absorbent pad (FIG. 2). The complete process from sample to answer took approximately 45 min, including an 18-min average for the paper extraction, followed by 2 min drying, 23-min RT-LAMP reaction, and 2 min for detection on the lateral flow strips.

Figure 11B:
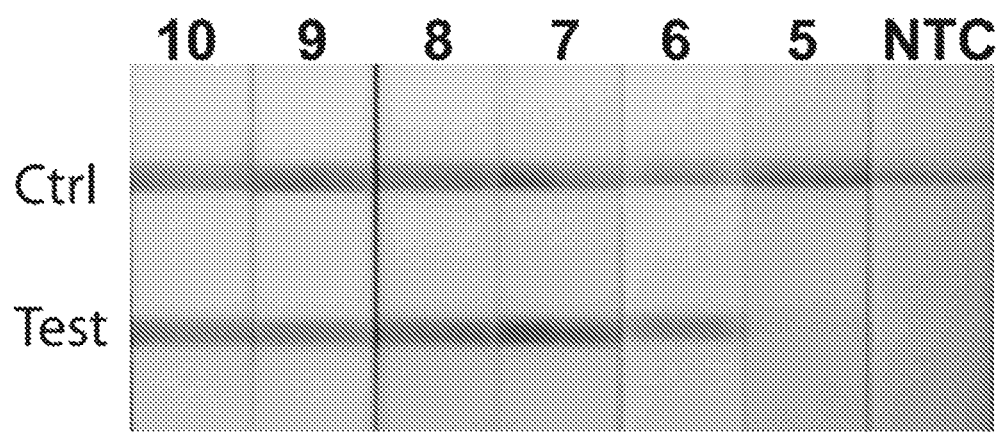
Figure 11C:
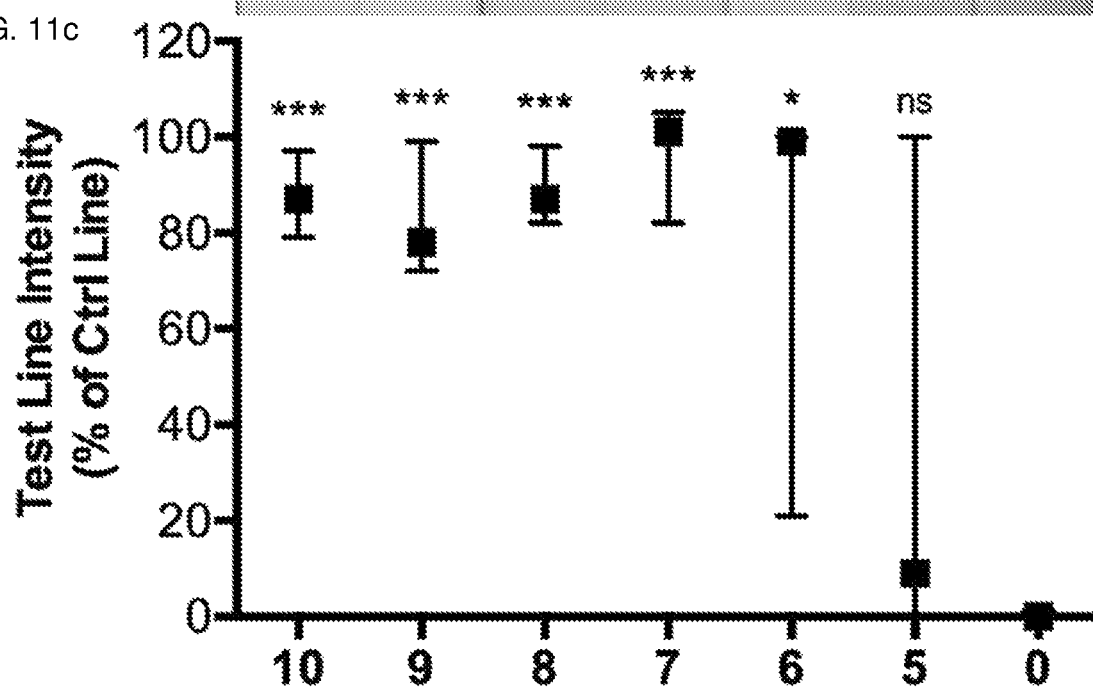

Solutions of influenza A (H1N1) RNA spiked into PBS at concentrations ranging from $10^{10}$ down to $10^5$ cp/mL and a negative control containing no RNA were extracted through the PES membrane just as in FIGS. 9a and 9b and amplified directly within the PES membrane via RT-LAMP in situ. The amplified products were eluted directly onto the lateral flow strips and representative lateral flow strips from three individual experiments are shown in FIG. 11b, and test line intensities from all three sets of strips were quantified and normalized to control line intensity (FIG. 11c). Statistical analysis from the three experiments determined that detection of all but the lowest concentration ($10^5$ cp/mL) were statistically significant when compared to the negative control. As shown in FIG. 11c, $10^5$ cp/mL was amplified to detectable levels in two of the three experiments, albeit lightly in one of them. From these results, we can conclude that our lower limit of detection for RT-LAMP in situ is an order of magnitude higher ($10^6$ cp/mL) than RT-LAMP in solution, however this would still theoretically cover over 90% of cases given the nasopharyngeal swab sample viral loads previously measured in a large group of patients.

Figure 13:
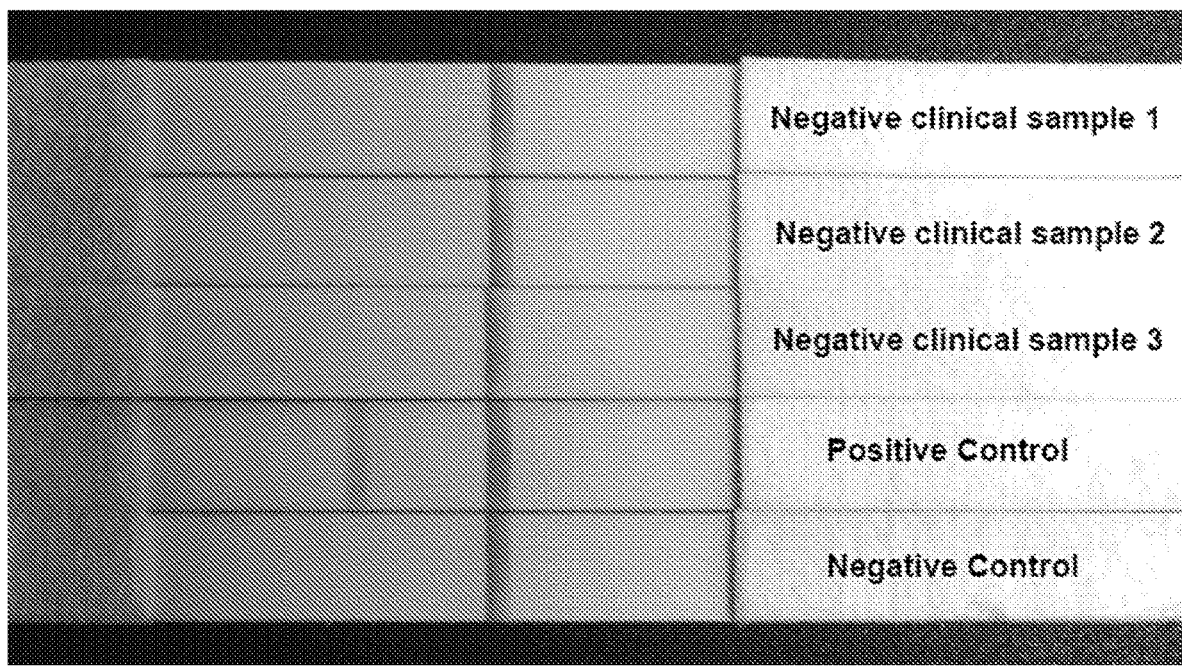
FIG. 13: Lateral flow detection strips from negative clinical samples that were PES-extracted and in situ RT-LAMP amplified. Three known H1N1-negative clinical samples from patients exhibiting symptoms of respiratory illness at the time of specimen collection were chosen at random. Prior laboratory testing indicated that sample 1 was Influenza B-positive, and samples 2 and 3 were Respiratory Syncytial Virus (RSV)-positive. None were detected by our assay, demonstrating our H1N1 strain-specificity. $10^9$ cp/mL H1N1 RNA and no RNA samples were run alongside the samples as positive and negative

Paper Extraction, In Situ RT-LAMP, and Lateral Flow Detection of H1N1 RNA from Clinical Nasopharyngeal Specimens To ensure compatibility of our paper extraction and in situ RT-LAMP assay with clinical specimens, 12 deidentified nasopharyngeal swab samples collected from patients that tested positive for H1N1 during the 2009 pandemic with a range of viral titers were selected for testing and labeled with letters A-L. Additionally, three H1N1-negative samples from patients exhibiting other respiratory illness at the time of specimen collection were chosen at random and tested by our assay (FIG. 13). Prior laboratory testing indicated that one of the samples was Influenza B-positive, and two samples were Respiratory Syncytial Virus (RSV)-positive.

Figure 12A:
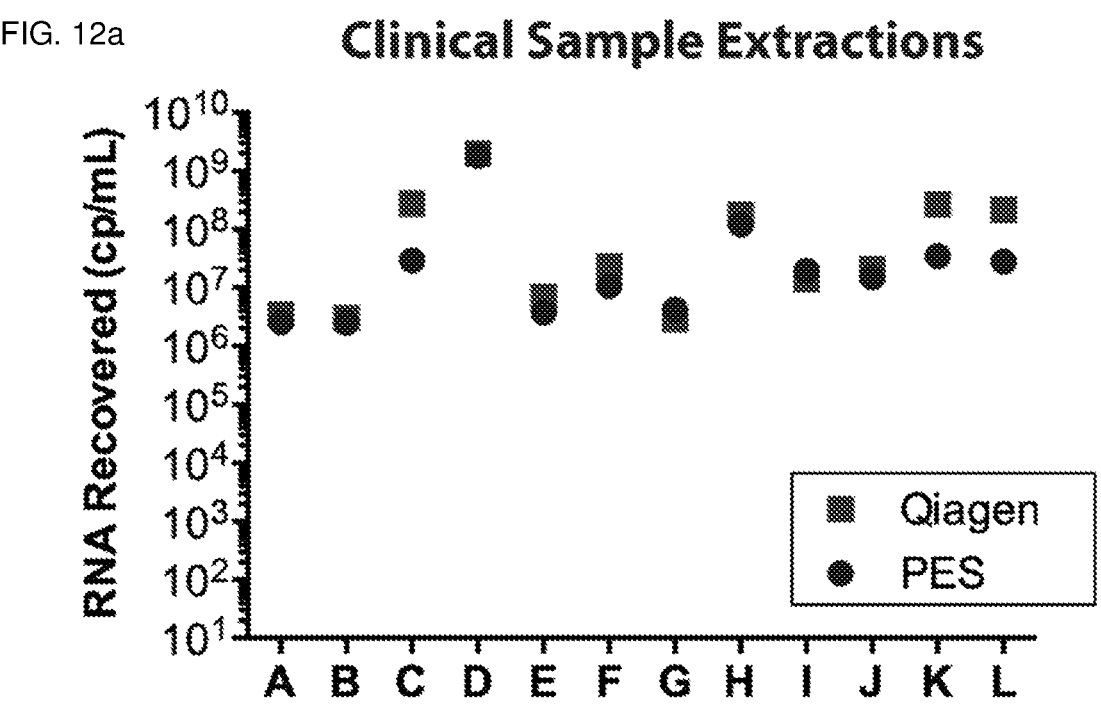
FIGS. 12a-12d: Clinical Nasopharyngeal Specimens. (a) Paper extractions and QIAamp kit extractions of clinical specimens A-L. (b) RT-LAMP assay performed in solution with Qiagen-extracted purified RNA from clinical specimens A-L, gel electrophoresis of products. (c) Lateral flow detection of amplified products; test line intensities plotted as percentage of control line intensities. (d) Paper extraction of clinical specimens A-L followed by in situ RT-LAMP and lateral flow detection. +=positive control ($10^9$ cp/mL RNA standard), −=negative control (no RNA).

Multiple aliquots were made of each clinical specimen and aliquots were stored at −80° C. One aliquot from each positive patient sample was extracted via a QIAamp Viral RNA Mini Kit as a gold standard extraction method. We compared our paper extraction method to the Qiagen kit via qRT-PCR (FIG. 12a). Our paper extraction yields ranged from 10% to 140% of Qiagen yields, exhibiting some variability that we speculate may be due to slight viral load variations across sample aliquots and possible effects of freeze-thaw cycles. Nonetheless, results show good correlation between recovered RNA quantities from each method.

Figure 12B:
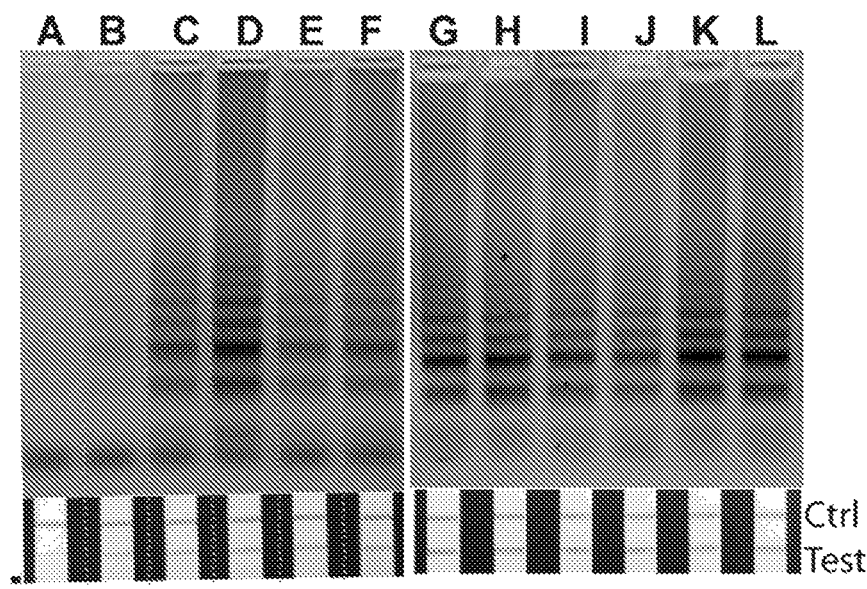
Figure 12C:
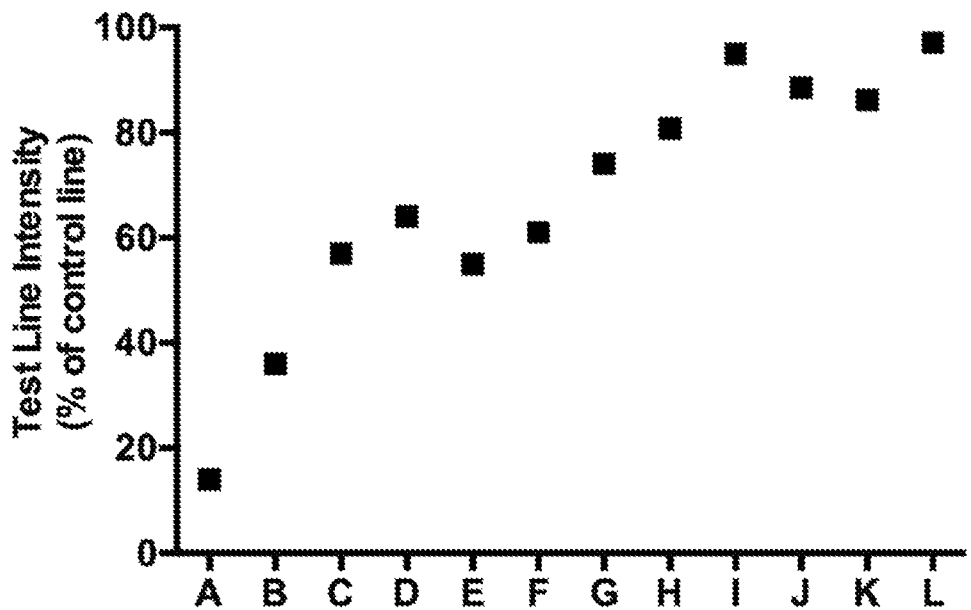
Figure 12D:
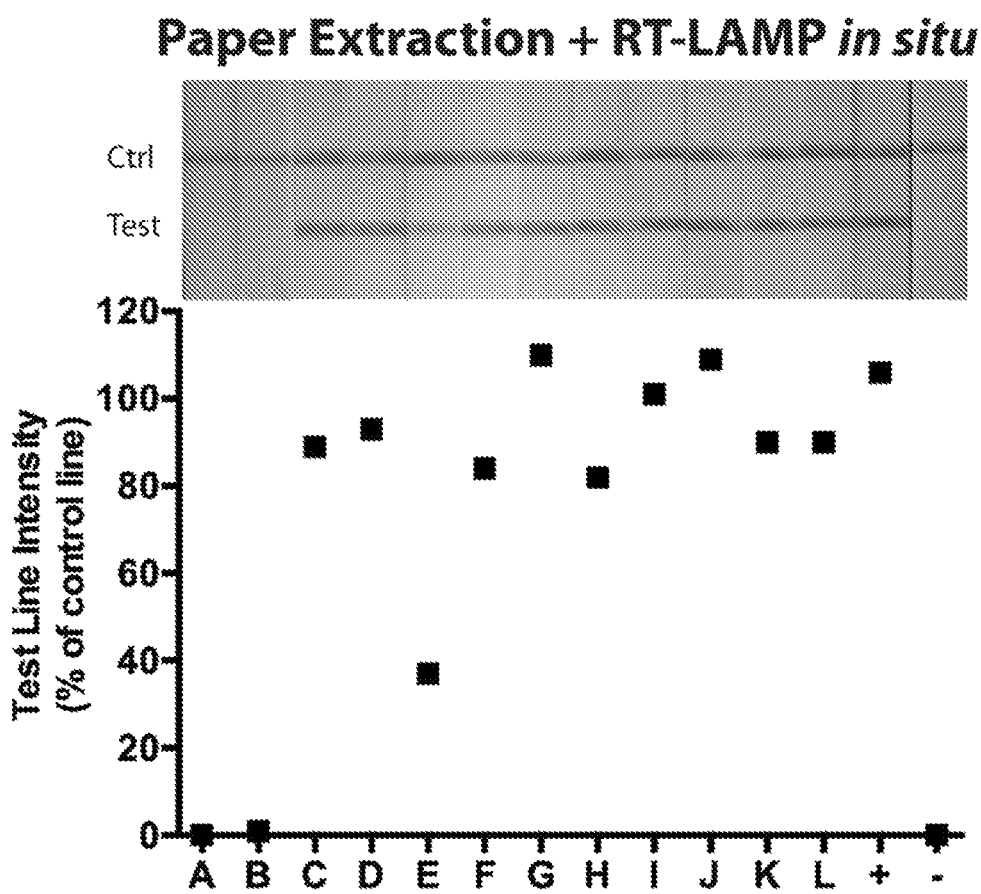

To be certain that our RT-LAMP assay would correctly amplify these H1N1 positive clinical specimens, we first performed RT-LAMP reactions in solution using purified Qiagen-extracted RNA from each positive sample. All positive samples were amplified to detectable levels as shown by agarose gel electrophoresis (FIG. 12b) and lateral flow detection (FIG. 12c). Next, a fresh aliquot of each sample was extracted via our paper extraction method and amplified via our in situ RT-LAMP assay. A positive ($10^9$ cp/mL in vitro transcribed RNA) and negative (no RNA) sample were also extracted and amplified as controls. After a 23-minute incubation at 65° C., the amplified products were eluted from the PES directly onto the lateral flow strips as shown in FIG. 11a, and strip test lines were quantified as a percentage of control lines (FIG. 12d). None of the negative clinical samples tested positive by our assay, as shown in FIG. 13, confirming our H1N1 strain-specificity. Ten of the twelve samples successfully tested positive via our paper extraction, in situ RT-LAMP, and LFD assay. The two samples that were not detected by our assay were the samples with the lowest viral titers (-2×$10^6$ cp/mL) and also resulted in the lowest test line intensities in the Qiagen-extract RTLAMP in solution control assay (FIG. 12c). This loss in sensitivity with clinical specimens as compared to our in vitro transcribed RNA standards tested in FIGS. 11b and 11c could be a result of additional inhibitors in the biological specimens that may have remained in the paper extraction matrix and could potentially have interfered with the LAMP reaction. For example, saline is known to inhibit LAMP amplification in a dose dependent manner, and it is possible that residual salt from the nasopharyngeal specimens were not entirely rinsed from the PES matrix during ethanol washes. Furthermore, incomplete inactivation of RNAses present in the specimens is also possible. Thus, thorough washing and RNAse inactivation should be ensured for best results.

Despite this slight loss in sensitivity with clinical samples, our paper extraction and in situ RT-LAMP assay still offers a significant improvement in detection limit over many commercially available rapid influenza diagnostic tests (RIDTs). Our lower detection limit of ~$10^6$ cp/mL is well within the clinically relevant range, and of the twelve known positive patient samples we tested, ten (83%) were correctly identified as positive by our assay.

Example 3

Device

Example 3 demonstrates the construction and functionality of a device of the invention by implementing an HPV 16 DNA extraction, amplification, and detection assay directly from patient cervical samples. This on-chip HPV 16 assay addresses many of the limitations of conventional cytology by providing highly sensitive molecular level information regarding the presence of high-risk HPV 16 in cervical samples without the need for laboratory infrastructure or highly trained pathologists.

A. Materials and Methods

Human Papillomavirus 16 Cloned DNA Standards

Human Papillomavirus 16 (HPV 16) DNA standards were generated by cloning the E7 gene for HPV 16 into the pGEM-T Easy Vector (Promega, Madison, Wis.). The E7 gene was PCR amplified from HPV-16 transformed cell DNA (Advanced Biotechnologies, Inc, Eldersburg, Md.) with gene-specific forward and reverse cloning primers (Table 2) containing restriction endonuclease sequences SpeI and AatII, respectively, using the standard Taq Polymerase protocol (New England Biolabs, Ipswich, Mass.).

TABLE 2

Primer Sequences

| Primer Name | Sequence | SEQ ID NO.: |
|---|---|---|
| PCR Fwd | AGC TCA GAG GAG GAG GAT GAA | 1 |
| PCR Rev | GGT TAC AAT ATT GTA ATG GGC TC | 2 |
| PCR Probe | /56-FAM/CC AGC TGG ACA AGC AGA ACC GG/3IABkFQ/ | 3 |
| SpeI Fwd* | CCGAACTAGTatgcatggagatacacc tacattgca | 4 |
| AatII Rev* | GATTGACGTCttatggtttctgagaac agatggggc | 5 |
| LAMP F3 | AGACAACTGATCTCTACTGTT | 6 |
| LAMP B3 | CTTCCAAAGTACGAATGTCTAC | 7 |
| LAMP FIP | TTCTGCTTGTCCAGCTGGACGCAATTA AATGACAGCTCAGAG | 8 |
| LAMP BIP | CCGGACAGAGCCCATTACAATGTGTGT GCTTTGTACGCA | 9 |
| LAMP LF | FITC-CATCTATTTCATCCTCCTC | 10 |
| LAMP LB | Biotin-TGCAAGTGTGACTCTACGCT | 11 |

*cloning primers
†Upper case letters indicate restriction enzyme sequence regions, and lower case letters indicate HPV-specific primer sequence regions.

The PCR product was purified via phenol chloroform extraction and ethanol precipitation. The cleaned PCR product was digested overnight with SpeI and AatII restriction endonucleases (New England Biolabs, Ipswich, Mass.). The relevant band was gel extracted and ligated to the pGEM vector and transformed into Top 10 cells from Life Technologies (Grand Island, N.Y.). Plasmid DNA was extracted using a Mini Prep Kit (Qiagen, Valencia, Calif.) and sequenced (GeneWiz, Inc, Cambridge, Mass.) to confirm proper E7 insert. A Midi Prep Kit (Qiagen, Valencia, Calif.) was used to generate large scale plasmid stocks of the correctly sequenced DNA. The plasmid stocks were linearized with ZraI restriction endonuclease (New England Biolabs, Ipswich, Mass.). The correct size fragment was gel extracted using the QIAquick Extraction Kit (Qiagen, Valencia, Calif.), phenol chloroformed, and ethanol precipitated. The concentration of the purified DNA was determined by measuring the OD260 with the NanoDrop ND-2000c apparatus (Thermo Scientific, Waltham, Mass.). The DNA copy number was calculated and 1 mL aliquots were made and stored at −20° C.

Clinical Cervical Specimens

The cervical specimens were accrued from the BIDMC cytology laboratory, on already tested and to be discarded specimens. The IRB approval and patient consent for research use of these de-identified and discarded specimens was waived by the BIDMC Institutional Review Board. The specimens were obtained in PreservCyt® solution. Testing was done on an FDA approved platform (Cervista; hrHPV), which evaluates 14 of the most common high-risk HPV genotypes (16, 18, 31, 33, 35, 39, 45, 51, 52, 56, 58, 59, 66, and 68) using Invader Chemistry. Any patient health identifying information was completely removed, and the specimens were labeled only as HPV positive or negative before they were transferred to the Klapperich Laboratory.

Samples were then transferred to 50 mL conical tubes, labeled with a sample number and centrifuged for 10 min at 4000 RPM. The supernatant was removed and the cell pellet was washed with 3 mL PBS, vortexed and centrifuged for 10 min at 4000 RPM. This was repeated twice, leaving a cell pellet that was resuspended in 3 mL PBS and divided into (3) 1 mL aliquots. Each 1 mL aliquot was centrifuged for 5 min at 13000 RPM. The supernatant was removed and pellets were frozen at −80° C. for long-term storage. Prior to use, pellets were resuspended in 1 mL PBS, subdivided into 200 μl aliquots, centrifuged for 10 min at 13000 RPM, and the supernatant was removed, resulting in single-use pellets for experiments.

For gold standard extraction experiments, DNA was extracted from a single-use pellet of each specimen using the DNeasy Blood & Tissue Kit (QIAGEN) and eluted into a final volume of 200 μl.

Quantitative PCR

To ascertain the DNA extraction yields, 5 μl of extracted DNA was amplified via quantitative PCR (qPCR). Using the Surestart Taq DNA polymerase (Agilent, Santa Clara, Calif.), real-time PCR was performed on an Applied Biosystems 7500 thermocyler under the following conditions: 10 min at 95° C. for polymerase activation, followed by 30 cycles of 30 sec at 95° C., 15 sec at 55° C. for primer annealing, and 90 sec at 60° C. for amplification. The 25 μL reaction mixture contained 1× TaqMan buffer, 3.5 mM MgCl2, 8% DMSO, 200 μM dNTPs, 200 nM primers and TaqMan probes, 0.1× Rox Reference Dye, 0.625U Taq DNA polymerase, and 5 μl of sample or standard DNA. For clinical specimen gold standard extraction experiments, a multiplexed HPV 16 and RNaseP qPCR assay was run following the same reaction conditions where RNaseP served as a DNA control to confirm that each clinical specimen did in fact contain cells and that the Qiagen extractions were performed properly. If a clinical sample was negative for RNaseP (cycle threshold value >30), the sample was deemed invalid and was not used for further experiments.

In each qPCR run, a cycle threshold number versus DNA concentration standard curve was generated from a dilution series of our cloned HPV 16 DNA standards. For each patient sample, the effective viral DNA concentration was quantitated via standard curve interpolations.

Isothermal Loop-Mediated Amplification Assay

An isothermal loop-mediated amplification (LAMP) assay was developed for rapid amplification and detection of the HPV 16 E7 gene using primer sequences previously designed (Luo et al, *J. Clin. Microbiol.*, 2011, 49, 3545-3550). The assay was first optimized in tube, and then translated to a chip format. The assay takes place in situ, in a PES membrane in the sample inlet port, as previously described (Rodriguez et al, *Anal. Chem.*, 2015, 87, 7872-7879). The in-tube reaction was carried out in a final volume of 25 µl with 1 µl of the DNA sample, 1× Isothermal Amplification Buffer (New England Biolabs), 8 U large fragment Bst 2.0 DNA polymerase, 0.8 M Betaine, 1 mM dNTPs, 5 µmol each of forward and reverse outer primers (F3 and B3), 20 µmol each of forward and reverse loop primers (LF and LB), and 40 µmol each of forward and reverse inner primers (FIP and BIP). The on-chip LAMP reaction recipe was identical but was carried out in a final volume of 12.5. Fresh, single-use aliquots of each reagent were used each time. The reaction was run for 30 minutes at 63° C. Forward and reverse loop primers (LF and LB) were tagged with Fluorescein isothiocyanate (FITC) and biotin, respectively, to enable immediate downstream detection of the amplified products on immunochromatographic, lateral flow detection (LFD) test strips (Ustar Biotechnologies, China) consisting of streptavidin-conjugated gold nanoparticles, an anti-FITC test line, and a biotin (anti-streptavidin) flow control line.

For in-tube LAMP assay experiments, the amplified products were analyzed by 2% agarose gel electrophoresis. The specificity of the products was confirmed by restriction enzyme digestion with the PvuII restriction endonuclease (New England Biolabs) with a single cutting site within the FIP region. Following digestion at 37° C. overnight, the digested products were analyzed by 2% agarose gel electrophoresis and by 10% acrylamide gel electrophoresis for higher resolution analysis.

LFD strips were imaged using an iPhone 5 camera (Apple). LFD test line and control line intensities were analyzed using the Gel Analysis feature in ImageJ (National Institutes of Health) by dividing the intensity of the test line by the intensity of the control line to obtain the percentage of control intensity for each sample. Unpaired, two-tailed Student's T-tests were used to determine the significance of each sample readout compared to the experimental negative control sample readout.

Chip Fabrication

Figure 14A:
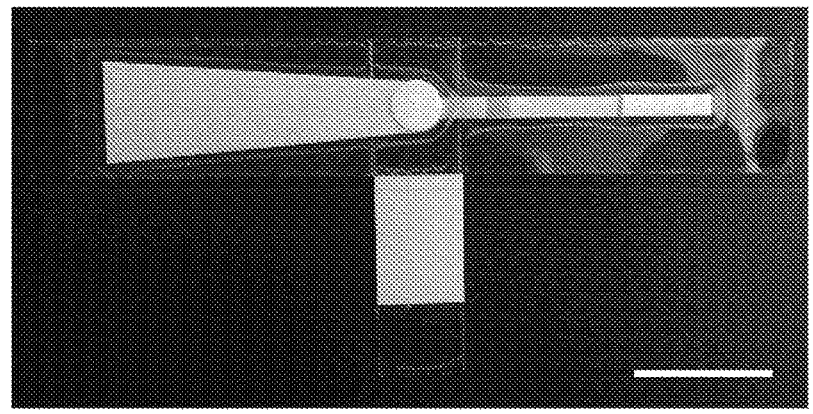
FIGS. 14a-14c: Molecular Diagnostic Chip. (a) Image of a chip. Scale bar=1 inch. (b) Blueprint drawings and dimensions for the housing of the chip. (c) Schematic of chip fabrication steps: i. The cut adhesive sheets are peeled from the protective backing and placed adhesive side-up on the benchtop (the white area is adhesive sheet, the dark grey areas are holes that have been cut out of the adhesive sheet); H. A capture region, e.g., 0.375 inch diameter PES disc, is manually placed directly over a 0.3 inch diameter hole in the adhesive sheet, and the top tab is folded down along the perforation over the PES; iii. The sample port is now created (the light grey color indicates areas where the adhesive sheet has been folded over onto itself, rendering the area non-adhesive); iv. The bottom tab is folded up along the perforation to create a toehold for what will become the sample port cover film to prevent evaporation, e.g., during a heating step; v. The 0.3 inch diameter circle of tape that had been cut out of the adhesive sheet to make the sample port is peeled off the protective backing where it stayed behind and is manually placed adhesive side-down onto the adhesive sheet 2 inches down from the center of the sample port. This will align with the sample port when the cover film is placed and prevent the sample and/or PES membrane from sticking to the adhesive cover film; vi. A waste region, e.g., absorbent pad, (dark grey) is manually aligned and placed over the sample port extending towards the left side of the chip; vii-viii. The lower middle section of the chip is then folded over the centerline perforation over the absorbent pad to create a hydrophobic (tape) barrier between the absorbent pad and a detection region, e.g., a lateral flow detection (LFD) strip; ix. The LFD strip is then manually aligned with the sample port center and placed down extending over the right side of the chip; x-xi. The bottom two remaining sections of the adhesive sheet are folded up over the perforations to seal the chip from the bottom; xii. The fabrication is now complete, and the chip is then flipped over so that the PES membrane sample port is right side-up and ready for use.
Figure 14B:
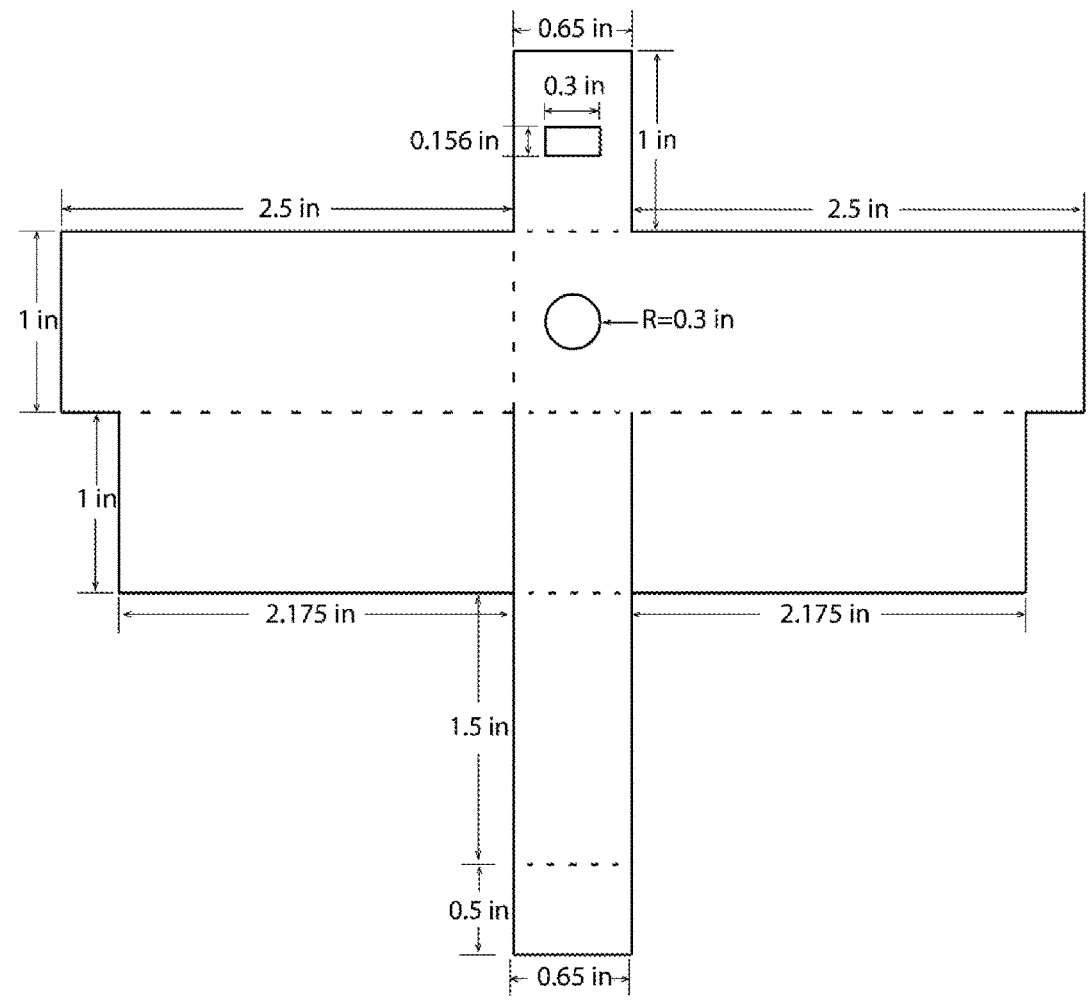
Figure 14C:
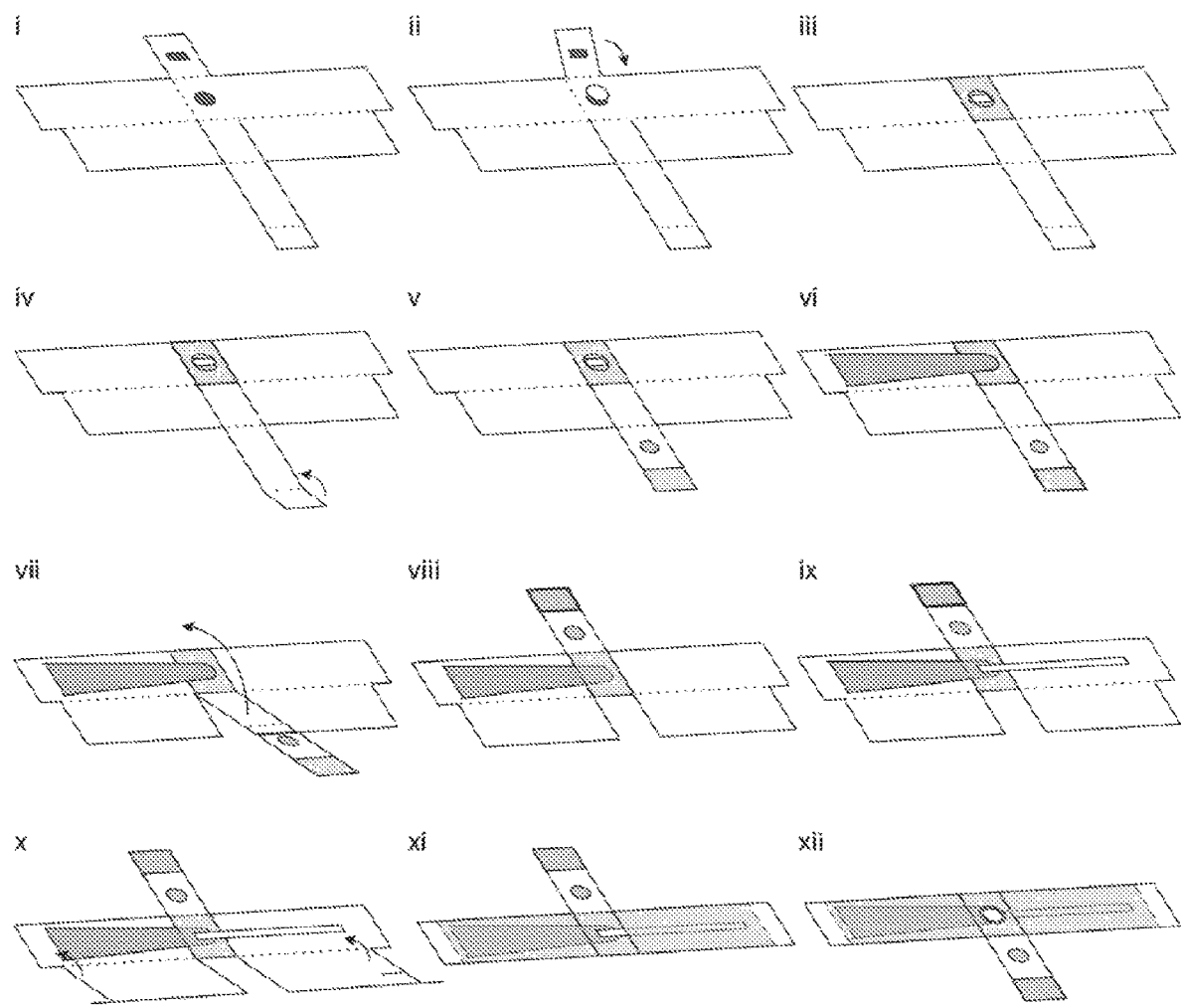

Standard letter size self-adhesive laminating sheets (Fellowes product #5221502) served as the base material for building the chip, providing a hydrophobic (tape) barrier surrounding the paper components that is low-cost and optically transparent to enable our visual readout (FIG. 14*a*). We created blueprint drawings for the adhesive base of the chip (FIG. 14*b*) using computer-aided design software (AutoCAD), and cut the adhesive sheets accordingly using an electronic craft cutting tool (Graphtec Craft Robo Pro S with Graphtec Studio software) using a standard blade (CB09U) and the following settings—cut force: 27, speed: 7 cm/s, acceleration: 1. The cut adhesive sheets are peeled from the protective backing and placed adhesive side-up on the benchtop as shown schematically in FIG. 14*c*, step i. PES filter paper (Millipore, cat #GPWP04700) was cut into 0.375 inch diameter discs using a ⅜" craft hole punch (EK Tools, 54-10061). A single 0.375 inch diameter PES disc is manually placed directly over the 0.3 inch diameter hole in the adhesive sheet, and the top tab is folded down along the perforation over the PES (FIG. 14*c*, step ii) to create the sample port (FIG. 14*c*, step iii). Next, the bottom tab is folded up along the perforation to create a toehold for what will become the sample port cover film to prevent evaporation during the LAMP heat step (FIG. 14*c*, step iv). The 0.3 inch diameter circle of tape that had been cut out of the adhesive sheet to make the sample port is peeled off the protective backing where it stayed behind and is manually placed adhesive side-down onto the adhesive sheet 2 inches down from the center of the sample port (FIG. 14*c*, step v). This will align with the sample port when the cover film is placed during LAMP and prevent the DNA and/or PES membrane from sticking to the adhesive cover film.

Cellulose blotting paper (Whatman GB003, cat #09-301-400) was cut using a 30 W Epilog Zing laser cutter (speed=70%, power=28%, frequency=200) to make absorbent pads shaped as 2.5 inch long sectors that extend radially from 0.375 inch at the base of the sample port to an ultimate width of 0.75 inch (drawn in SolidWorks, company, city, state). The absorbent pad is manually aligned and placed over the sample port extending towards the left side of the chip as shown in FIG. 14*c*, step vi. The lower middle section of the chip is then folded over the centerline perforation over the absorbent pad as shown in FIG. 14*c*, steps vii-viii to create a hydrophobic (tape) barrier between the absorbent pad and the LFD strip. The LFD strip is then manually aligned with the sample port center and placed down extending over the right side of the chip as shown in FIG. 14*c*, step ix. Next, the bottom two remaining sections of the adhesive sheet are folded up over the perforations to seal the chip from the bottom (FIG. 14*c*, steps x-xi). The fabrication is now complete, and the chip is then flipped over so that the PES membrane sample port is right side-up and ready for use (FIG. 14*c*, step xii).

Figure 15A:
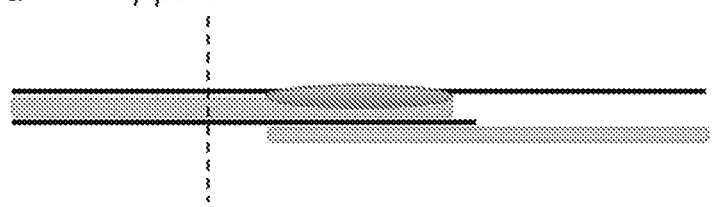
FIGS. 15a-15c: Chip Sideview Schematic. (a) Chip prior to use. The absorbent pad (grey) is in direct contact with the PES sample port (blue); thus, any liquid will wick into the absorbent pad and towards the left. Once extraction and wash steps are complete, the chip is ripped at the perforation in the tape, and the entire left side of the chip is removed. (Note the now wet absorbent pad delaminates from the tape, allowing complete removal). (b) After the absorbent pad has been removed, the PES and LFD strip (LFS, pink) are separated by a hydrophobic tape barrier. (c) After nucleic acid amplification, e.g., LAMP, the tape barrier is removed (by ripping at a perforation) and the PES is left in direct contact with the LFD strip, allowing eluted amplified products to wick directly onto the strip.
Figure 15B:
Figure 15C:
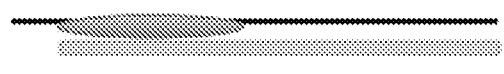

Integrated On-Chip Assay a. DNA Extraction and Purification. A single-step cell lysis and DNA extraction recipe was developed based on chaotropic lysis and alcohol precipitation methods known in the art (Boom et al, *J. Clin. Microbiol.*, 1990, 28, 495-503; Linnes et al, *RSC Adv,* 2014, 4, 42245-42251). A single-use pellet of each clinical cervical specimen (or 6 µl of cloned HPV16 DNA during preliminary experiments) was resuspended in a lysis buffer containing 3M guanidinium thiocyanate, 300 mM sodium chloride, 35% v/v 1-butanol (Sigma Aldrich, St. Louis, Mo.), and 3 µl of 15 mg/mL Glycoblue coprecipitant (Life Technologies, Grand Island, N.Y.) in a total volume of 100 µl. This mixture was pipetted onto the sample port of the paperfluidic chip. The liquid phase wicks through the absorbent pad directly underneath the PES membrane by capillary forces, leaving the precipitated DNA-Glycoblue solid phase. A series of ethanol washes (200 µl of 70% ethanol, followed by 100 µl of 100% ethanol) were then pipetted through the sample port, removing impurities while leaving the purified DNA-glycogen precipitate on the PES membrane. The left side of the chip containing the soiled absorbent pad was then ripped along the perforation and discarded.

b. Isothermal Amplification. A 12.5 µl LAMP reaction mix was pipetted directly onto the sample port and was fully absorbed by the PES, presumably dissociating the DNA-Glycoblue complexes. The bottom tab of the chip is then folded up along the perforation and pressed down to seal over the absorbent pad and serves as a cover film to prevent evaporation during the incubation period for LAMP. The chip is then placed face-down on a 63° C. heat block or hot plate for 30 min.

c. Lateral Flow Detection. Following the LAMP incubation, the cover film was peeled back using the toehold tab to expose the sample port on top, and peeled under the chip to expose the sample port outlet on the bottom, thereby removing the hydrophobic (tape) barrier between the sample port and the LFD strip (see side view schematic in FIGS. 15a-15c). 50 µl of nuclease free water was then pipetted onto the sample port, which filtered through the PES and wicked directly onto the LFD strip for immediate detection of amplified products.

B. Fluidic Demonstration of Chip Operation

Figures 16I, 16X:
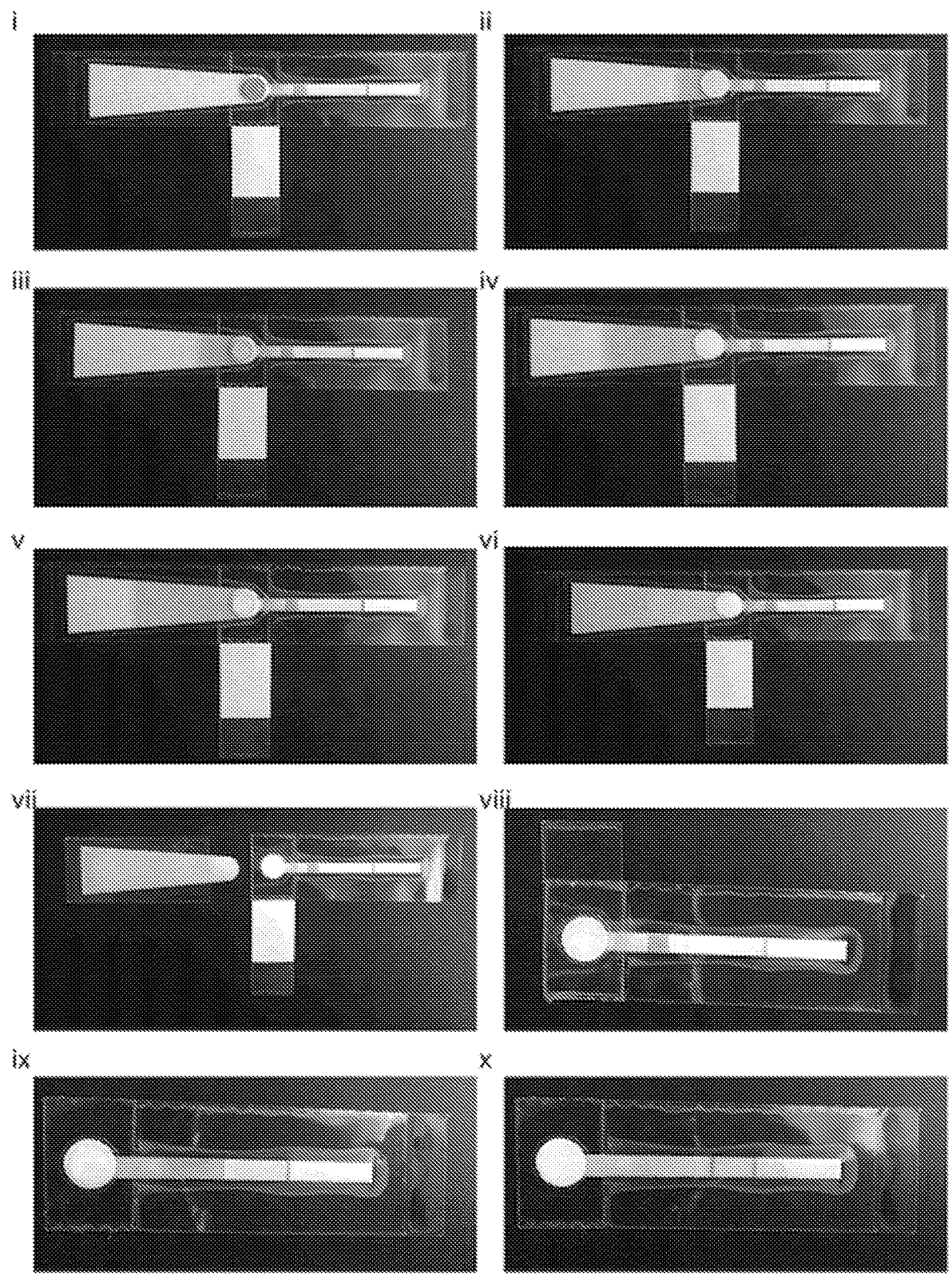
FIGS. 16i-16x: Fluidic Demonstration of Chip Operation. (i) A lysed sample, demonstrated here using 100 µl of blue dye, is placed onto the sample port of the chip using a pipette or dropper. (ii) The prevailing capillary forces generated by the absorbent pad directly underneath the sample port quickly wick the liquid waste through the PES membrane and away from the sample port leaving the solid phase behind. (iii) A first wash of 70% ethanol, demonstrated here using 200 µl of yellow dye, is filtered through the sample port. (iv) The wash buffer will wick through to the absorbent pad, removing impurities and leaving behind the purified precipitated DNA. (v-vi) A final wash of 100% ethanol, demonstrated here using 100 µl water, is filtered through the sample port, leaving just the purified DNA on the PES membrane. (vii) The waste absorbent pad is discarded by ripping off the left side of the chip at the designated perforation. (viii) An isothermal, e.g., LAMP, reaction mix is placed directly onto the sample port where the purified DNA remains, and the bottom tab of the chip is folded up over the designated perforation to act as a cover film for the sample port and prevent evaporation during the heat step. (ix) After the heat incubation for LAMP, the cover film is peeled back using the toehold to expose the sample port on top, and peeled under the chip to expose the sample port outlet on the bottom, thereby removing the hydrophobic (film) barrier between the sample port and the LFD strip. The PES membrane is now in direct contact with the LFD strip and the amplified products are then eluted onto the strip by adding 50 µl water to the sample port. (x) The eluted products wick through the LFD strip towards the right.

A lysed sample, demonstrated here using 100 µl of blue dye, is placed onto the sample port of the chip using a pipette or dropper (FIG. 16i). The prevailing capillary forces generated by the absorbent pad directly underneath the sample port quickly wick the liquid waste through the PES membrane and away from the sample port (FIG. 16ii). A hydrophobic (tape) barrier between the absorbent pad and the LFD strip prevents the liquid waste from wicking through to the LFD strip (see side view schematic in FIG. 15a-15c). Any solid phase within the sample, most importantly the precipitated DNA, will remain on the sample port surface. Next, a first wash of 70% ethanol, demonstrated here using 200 µl of yellow dye, is filtered through the sample port (FIGS. 16iii-iv). The wash buffer will wick through to the absorbent pad, removing most impurities like cell debris, proteins, and salts and leaving behind the purified precipitated DNA. Because ethanol can inhibit the subsequent LAMP reaction, it is important to completely dry the sample port. To that end, a final wash of 100% ethanol, demonstrated here using 100 µl water, is filtered through the sample port (FIG. 16v), leaving just the purified DNA precipitates on the PES membrane (FIG. 16vi).

The waste absorbent pad is no longer needed at this point and can be discarded by ripping off the left side of the chip at the designated perforation (FIG. 16vii). Next, 12.5 µl of the LAMP reaction mix is placed directly onto the sample port where the purified DNA remains, and the bottom tab of the chip is folded up over the designated perforation to act as a cover film for the sample port and prevent evaporation during the heat step (FIG. 16viii). The chip is then placed face-down onto a heat block or hot plate set to 63° C. for 30 min (not shown). After the heat incubation, the cover film is peeled back using the toehold to expose the sample port on top, and peeled under the chip to expose the sample port outlet on the bottom, thereby removing the hydrophobic (tape) barrier between the sample port and the LFD strip. The PES membrane is now in direct contact with the LFD strip and the amplified products are then eluted onto the strip by adding 50 µl water to the sample port (FIG. 16ix). The eluted products wick through the LFD strip towards the absorbent pad on the right. As the liquid wicks through the conjugate pad, the streptavidin-conjugated gold nanoparticles bind the biotin probes on the LB primers within the amplicons. As the liquid continues to wick over the detection zone, amplicons that also contain the FITC probe on the LF primers will aggregate at the anti-FITC test line. Any excess streptavidin-conjugated gold nanoparticles will continue to wick through the LFD strip and bind the biotin control line, which confirms that the strip functioned properly. In this example, water was used as a negative control, thus only the control line appears on the strip (FIG. 16x).

C. HPV 16 E7 LAMP Assay

Figure 17A:
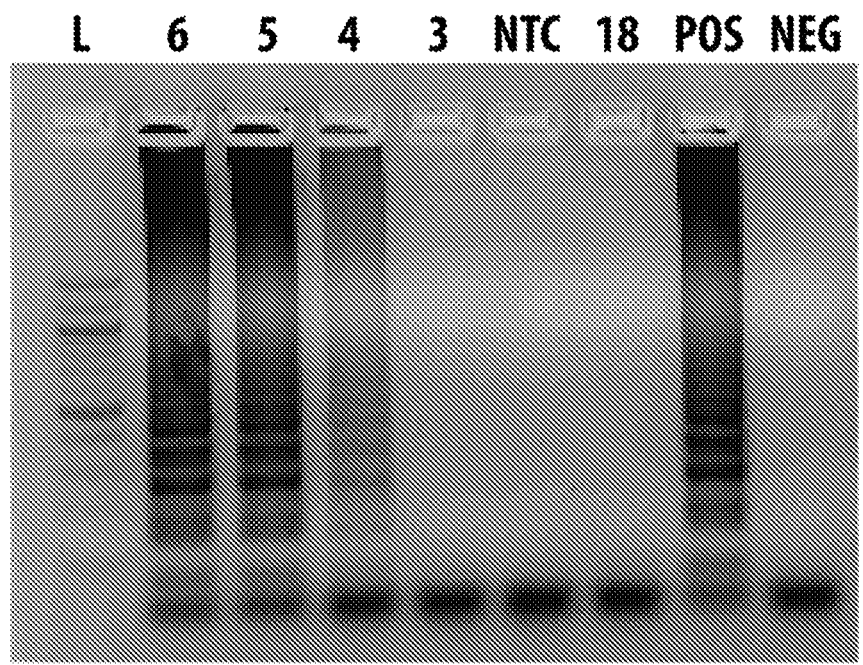
FIGS. 17a-17e: HPV 16 E7 LAMP Assay in solution. (a) 2% Agarose gel electrophoresis of LAMP products. L=100 bp DNA Ladder, $6=10^6$ DNA copies, $5=10^5$ DNA copies, $4=10^4$ DNA copies, $3=10^3$ DNA copies, NTC=no template control, $18=10^6$ copies of HPV 18 DNA, POS=DNA extracted from an HPV16-positive patient sample, NEG=DNA extracted from an HPV16-negative patient sample. (b) Representative lateral flow strips from three independent experiments show detection of LAMP products. Top line is the test line, bottom line is the flow strip control line. (c) Test line intensity as percentage of control line intensity for three experiments is plotted (* p<0.001, ** p<0.0001, ns=not significant). (d) 2% Agarose gel electrophoresis of Pvull-digested LAMP products. L1=100 bp DNA Ladder, L2=PBR322 DNA-Msp1-digest Ladder. (e) 10% Acrylamide gel electrophoresis of Pvu-II digested LAMP products.
Figure 17B:
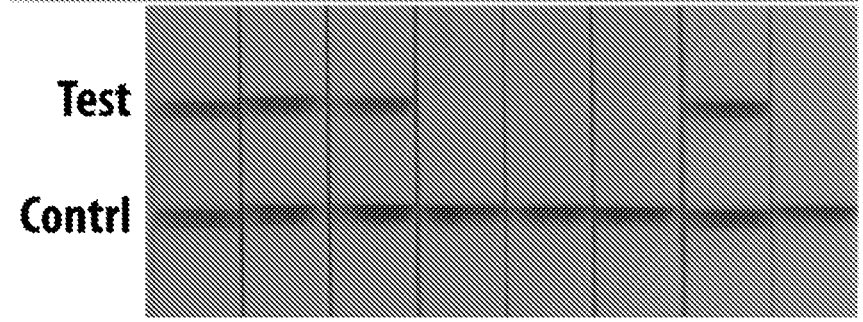
Figure 17C:
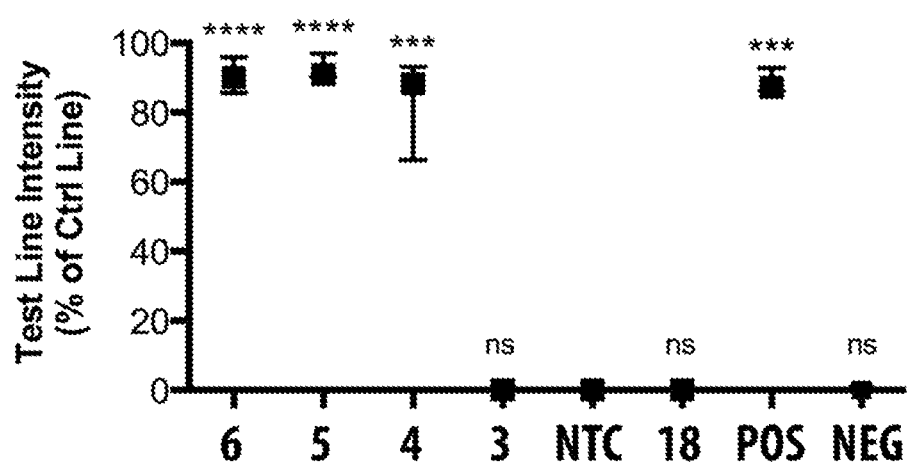

The HPV 16 E7 LAMP assay was first optimized in-tube using our cloned HPV16 DNA standards. We ran the optimized LAMP assay using serial dilutions of our DNA standards and found that our lower limit of detection was $10^4$ total copies as confirmed by agarose gel electrophoresis (FIG. 17a) and LFD strips (FIG. 17b). The LFD strips enable immediate detection of amplified products with the naked eye. Test line intensities were quantified as a percentage of control line intensities and results from three independent experiments are plotted in FIG. 17c. DNA quantities down to $10^4$ total copies show a clear visible test line that is statistically different from the negative control. While $10^3$ DNA copies were not amplified to detectable levels, the HPV literature has shown that a viral load below $10^4$ copies is not indicative of cervical cancer progression (Duin et al, *Int. J. Cancer*, 2002, 98, 590-595).

We included a no template control (NTC), and a nonspecific DNA control ($10^6$ total copies of HPV 18 DNA), both of which were negative on both the gel and LFD strips, demonstrating primer specificity. Additionally, we ran our LAMP assay on Qiagen kit-extracted DNA from a patient sample that tested positive for HPV 16 and from a clinical sample that tested negative for HPV 16. It is important to note that these samples contain large amounts of human DNA and potentially other viral genomes. Our LAMP assay correctly identified these patient samples as positive and negative, respectively, thus further confirming the specificity of our LAMP assay.

Figure 17D:
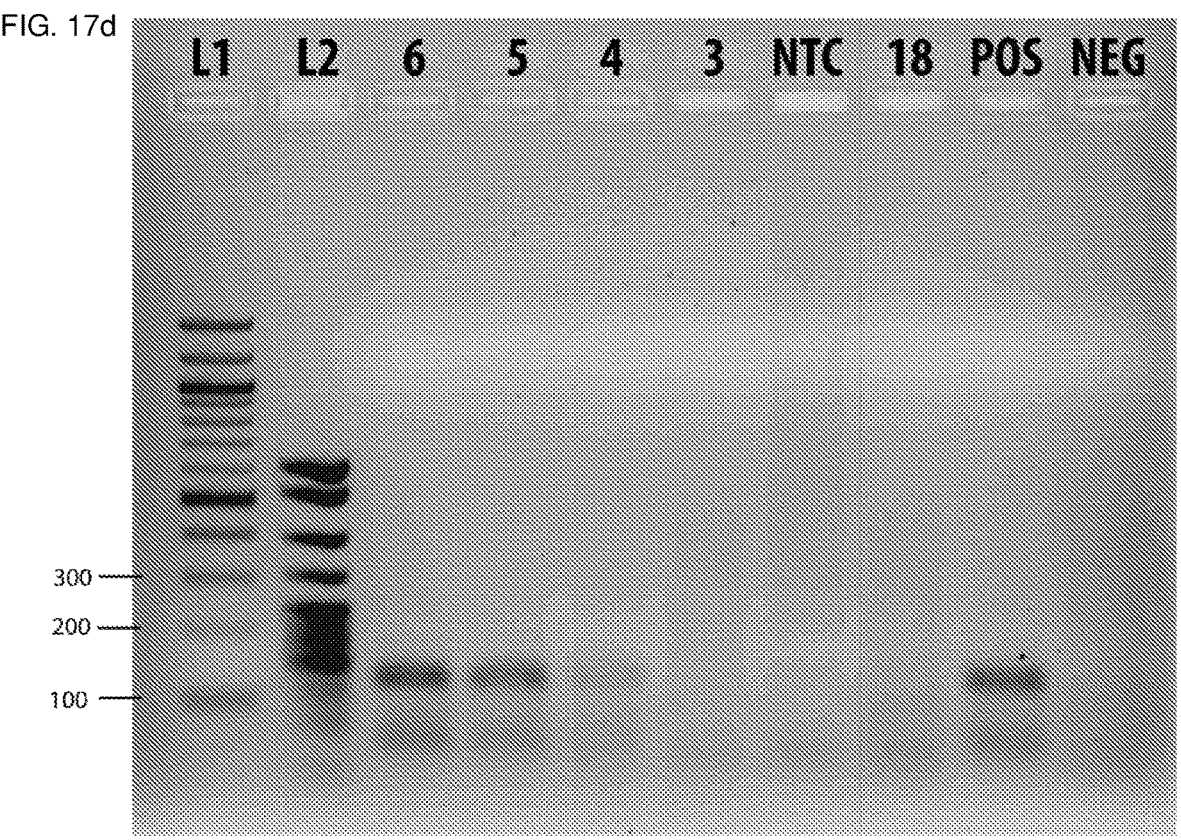
Figure 17E:
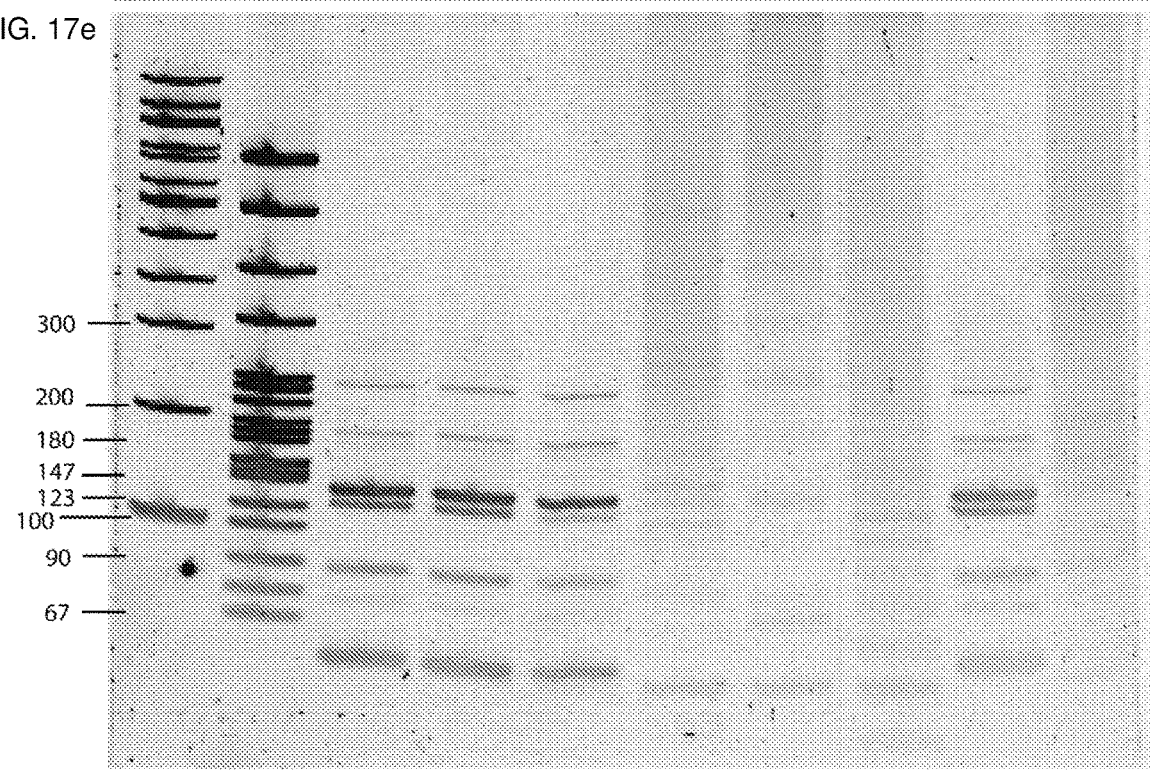

One disadvantage to the LAMP method is the possibility for interaction and self-priming of the oligonucleotides during the reaction. This phenomenon is usually circumvented by optimization of assay conditions and setting an assay cutoff time far before these events are likely to occur. Nonetheless, because our ultimate assay detection method is based on primer-tagged probes, it was important to ensure that a positive result on the LFD strip correlated to a LAMP product specific to our target sequence. To this end, the amplified products were digested with the PvuII restriction endonuclease and analyzed by 2% agarose gel electrophoresis (FIG. 17d) and at higher resolution by 10% acrylamide gel electrophoresis (FIG. 17e). The HPV 16 E7 gene sequence contains a single PvuII cutting site within the FIP region, and positive product digests were in agreement with the expected product band sizes (Notomi et al, *Nucleic Acids Res.*, 2000, 28, E63), while the negative product digests showed nothing on a low-resolution agarose gel (FIG. 17d) and showed irregular band patterns inconsistent with expected product band sizes on a high-resolution acrylamide gel (FIG. 17e).

Figure 18A:
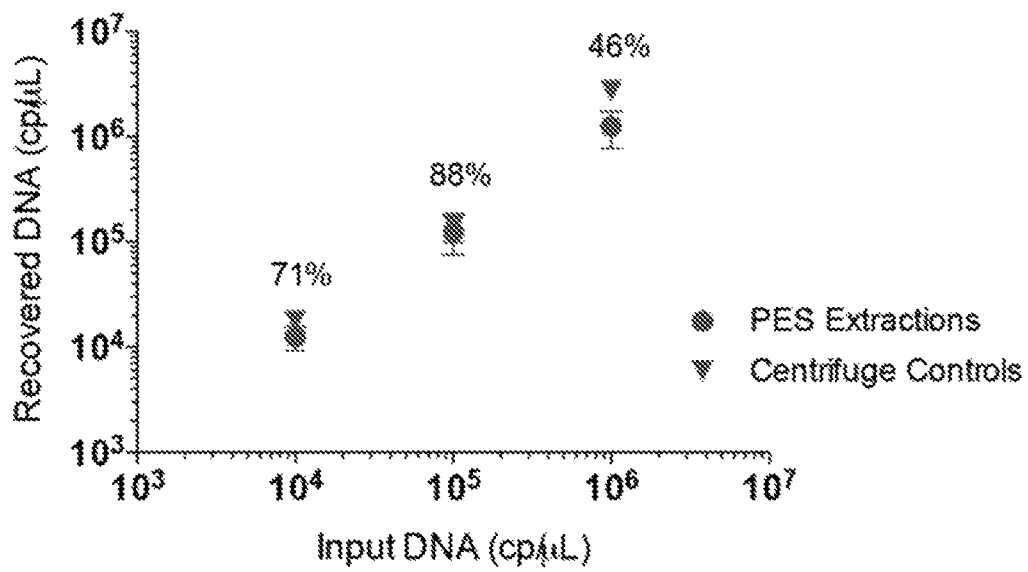
FIGS. 18a-18b: HPV 16 PES Extractions and in situ LAMP. (a) Paper extractions of HPV DNA standards and centrifuge control extraction yields quantified via qPCR. Error bars, SD. Percentage values indicate paper extraction yields compared to centrifuge control yields. (b) In situ LAMP reactions performed directly within a PES matrix. 1 $E5=10^5$ total DNA copies per reaction, 1 $E4=10^4$ total DNA copies per reaction, NTC=no template control.
Figure 18B:
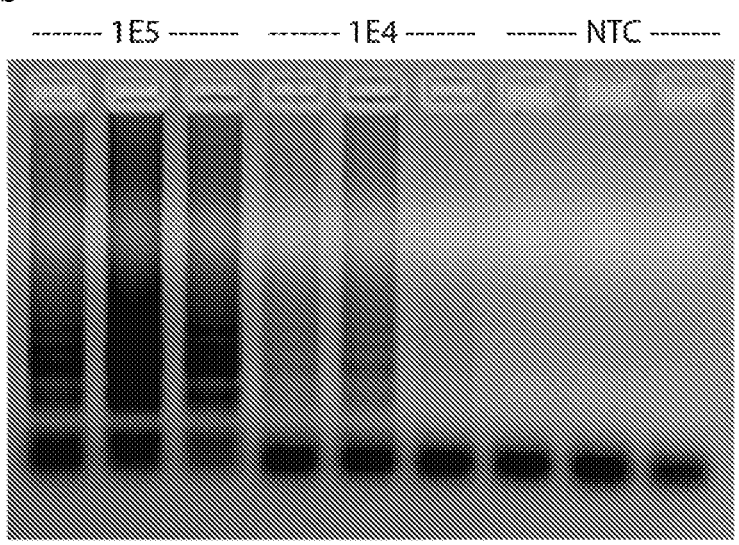

Having confirmed the lower detection limit and specificity of our HPV 16 LAMP assay in-tube, we then tested our LAMP assay in situ, directly within a paper matrix containing freshly extracted HPV 16 DNA. To test our HPV16 LAMP assay in situ, first we extracted solutions of known concentrations of HPV16 DNA mixed with our Glycoblue-containing lysis buffer through a PES membrane using an acrylic extraction setup known in the art (Rodriguez et al, *Anal. Chem.*, 2015, 87, 7872-7879). The extracted DNA was eluted from the PES matrices and quantified via qPCR (FIG. 18a). Recovery yields were between 46% and 88% of centrifugation controls, consistent with what our group had previously reported for RNA. Next, HPV 16 DNA solutions were again extracted through a PES membrane as described above, but this time instead of eluting the extracted DNA from the PES, 12.5 µl of our LAMP reaction mix was pipetted directly onto the PES membrane where it was fully absorbed. The PES disc was placed inside of a tube and incubated at 63° C. for 30 min. The amplified products were eluted via centrifugation from the PES membrane and analyzed via 2% agarose gel electrophoresis. As shown in FIGS. 18*a* and 18*b*, our LAMP assay successfully amplified as low as $10^4$ total copies of HPV 16 DNA in situ.

D. Integrated On-Chip Assay with Cloned HPV 16 DNA Standards

Figure 19A:
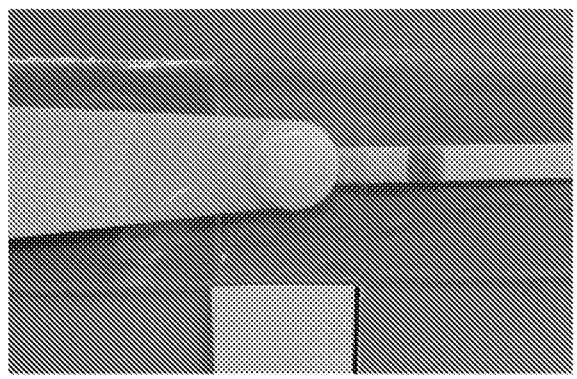
FIGS. 19a-19b: On-chip extraction images demonstrating (a) visible blue DNA-Glycoblue film forming on PES and (b) hardly any blue visible on absorbent pad underneath.
Figure 19B:
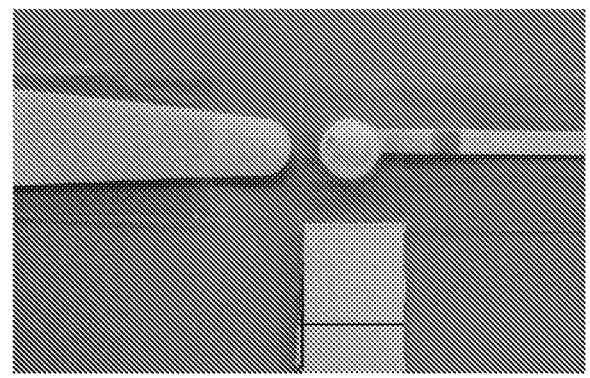

Once we confirmed adequate extraction and amplification of HPV 16 DNA in a PES membrane, we then integrated each assay component onto our chip, following the step-by-step protocol outlined in FIGS. 16*i*-16*x* and using solutions of known concentrations of our cloned HPV 16 DNA standards. On-chip extractions took approximately 10-15 minutes, as flow was significantly slowed after a visible blue DNA-Glycoblue film developed on the PES membrane following the initial sample filtration (images shown in FIGS. 19*a* and 19*b*). We also found that we needed to dispense the 100 µl sample only 50 µl at a time due to the lower surface tension of our lysis buffer containing 35% butanol, otherwise the liquid would spill over the sample port. Likewise, our 70% ethanol wash was dispensed 25 µl at a time, and the 100% ethanol wash was dispensed 10 µl at a time. Following the extraction and ripping off of the waste pad, the visible Glycoblue-containing dry precipitates were observed only on the PES membrane, and not significantly on the absorbent pad underneath, suggesting good recovery (FIG. 19*b*). The LAMP reaction mix was then added directly to the dry sample port and immediate mixing with the Glycoblue-containing precipitates was observed. Following the 30 min heat step, the cover film tab was peeled back and the LAMP reaction liquid was visibly still present on the sample port, suggesting minimal evaporation. Following addition of 50 µl water to the sample port, elution onto the LFD strip began immediately, and test results were visible within 2 min.

Figures 20A, 20B:
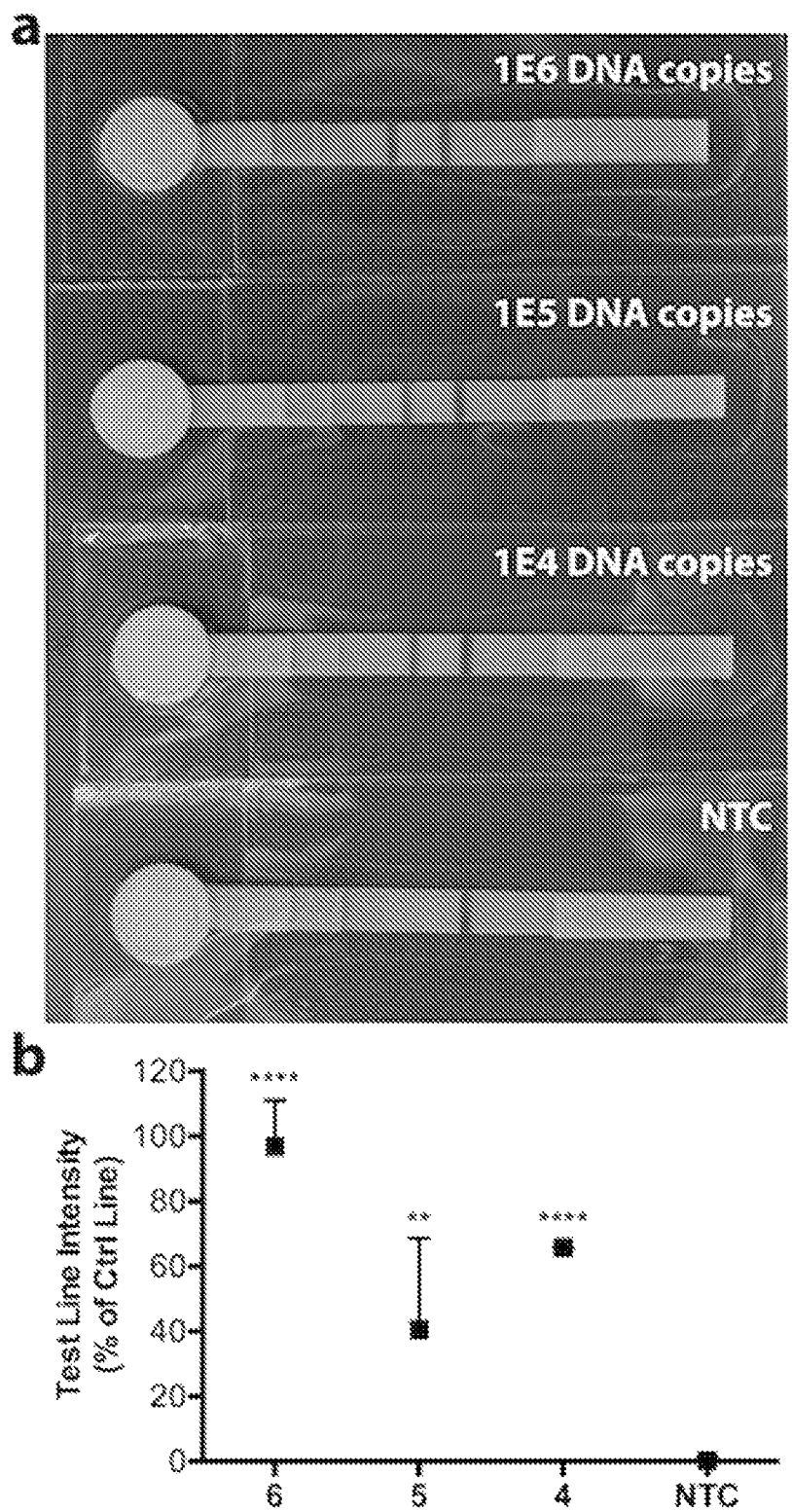
FIGS. 20a-20b: Integrated on-chip assay with cloned HPV 16 DNA standards. (a) Representative lateral flow strips from three independent on-chip experiments show detection of LAMP products from 1 E4 ($10^4$) to 1 E6 ($10^6$) DNA copies, NTC=no template control. Left line is the test line, right line is the flow strip control line. (b) Test line intensity as percentage of control line intensity for three experiments is plotted ( p<0.01, * p<0.001, **** p<0.0001).
Figures 21A, 21B, 21C, 21D, 21E, 21F, 21G, 21H, 21I, 21J:
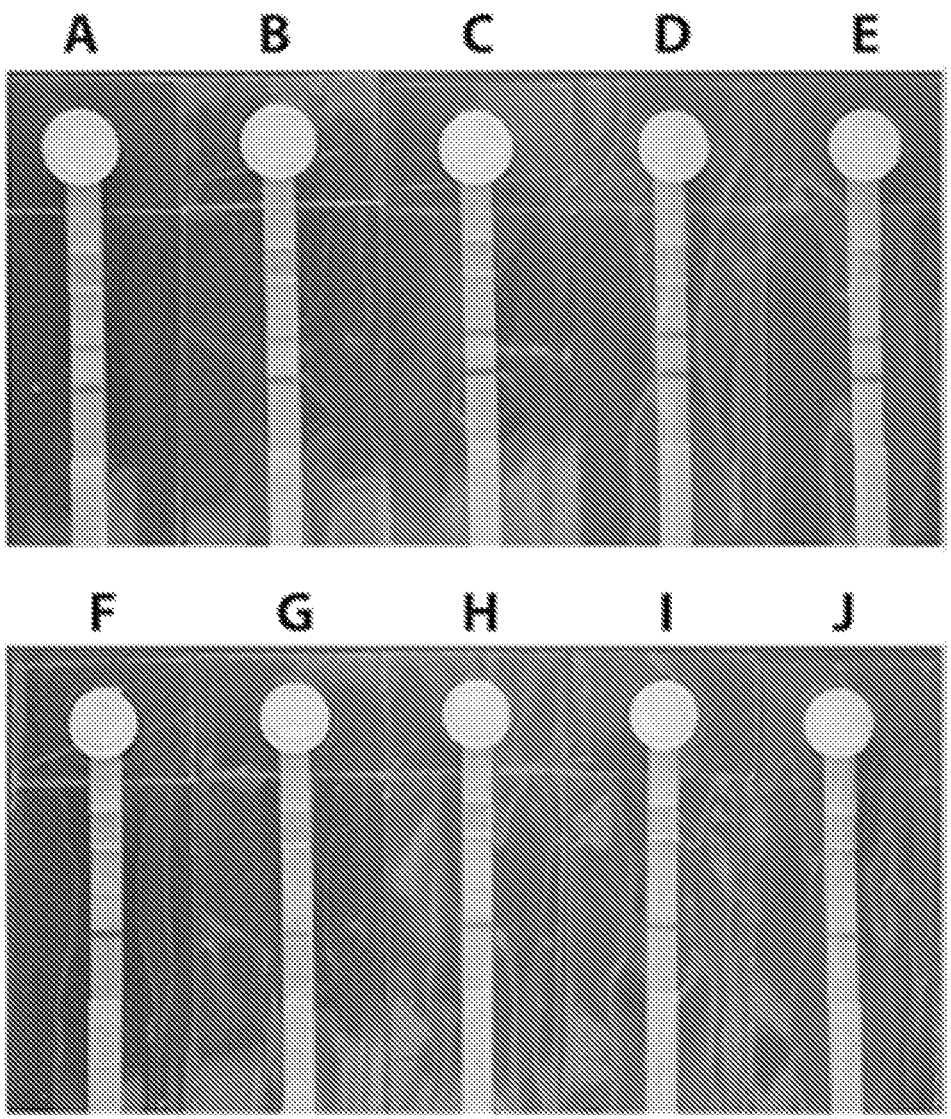
FIGS. 21A-21J: Integrated on-chip assay with clinical cervical specimens. Chip LFD strip images for each of ten patient samples A-J. A-E are HPV positive samples, F-J are HPV negative samples.

As shown in FIGS. 20*a* and 20*b*, our integrated on-chip assay resulted in clear, positive LFD readouts from starting material as low as $10^4$ copies of HPV 16 DNA, and a clear negative readout for the negative control. The statistical analysis from three independent experiments is shown in FIG. 20*b*.

E. Integrated On-Chip Assay with Clinical Cervical Specimens

DNA from cervical tissue sample pellets was extracted via the gold standard Qiagen DNeasy Tissue Kit. Each sample extraction was analyzed by qPCR for HPV16 E7 and RNaseP DNA. RNaseP serves as a human gene internal control to ensure that the cervical swab sample contained cervical cells and that DNA was properly extracted. Any samples that tested negative for RNaseP by qPCR were considered "invalid" and were not used in further experiments. Five HPV 16 positive and five HPV 16 negative samples (Table 3) were selected for on-chip testing to demonstrate proof-of-concept clinical utility of our paperfluidic chip. Results are shown in FIGS. 21A-21J.

TABLE 3

Gold standard (Qiagen-extraction quantified by qPCR) results from clinical cervical specimens for HPV16 and RNaseP control DNA quantities for each of 10 patient samples labeled A-J.

| Sample ID | HPV 16 Quantity Mean (total DNA copies) | RNaseP Quantity Mean (total DNA copies) |
|---|---|---|
| A | 9.00E+06 | 4.54E+04 |
| B | 1.89E+05 | 1.78E+04 |

TABLE 3-continued

Gold standard (Qiagen-extraction quantified by qPCR) results from clinical cervical specimens for HPV16 and RNaseP control DNA quantities for each of 10 patient samples labeled A-J.

| Sample ID | HPV 16 Quantity Mean (total DNA copies) | RNaseP Quantity Mean (total DNA copies) |
|---|---|---|
| C | 6.04E+06 | 6.58E+05 |
| D | 5.08E+07 | 5.48E+05 |
| E | 1.27E+05 | 7.52E+04 |
| F | NEG | 1.39E+05 |
| G | NEG | 2.16E+05 |
| H | NEG | 1.70E+05 |
| I | NEG | 1.30E+05 |
| J | NEG | 1.07E+06 |

NEG = negative result.

A single-use pellet from each sample A-J was resuspended in 100 µl lysis buffer, vortexed thoroughly, and pipetted onto the sample port of the chip. During preliminary experiments, significant accumulation of debris and salts from the lysed samples left a visible grainy film on the PES membrane, which greatly inhibited the subsequent LAMP reaction. This prompted an increase from 100 to 200 µl of our 70% ethanol washes, which did not entirely remove the residue in all cases, but significantly improved LAMP performance nonetheless.

All five positive samples resulted in clear, positive LFD results as seen in FIGS. 21A-21E. Of the five negative samples, three resulted in a negative LFD result (strips G, I, J), and two exhibited faint test lines (F, H), a result that could be mitigated by the use of a sequence specific probe (not primer-tagged), as discussed above.

Herein we have demonstrated the fabrication and use of a fully integrated, sample-to-answer, molecular diagnostic assay on a low-cost, disposable paperfluidic chip platform.

Example 4

Integration of Polyethersulfone (PES) and Cyclo Olefin Polymer (COP)

A. COP Reaction Chamber

Figure 22:
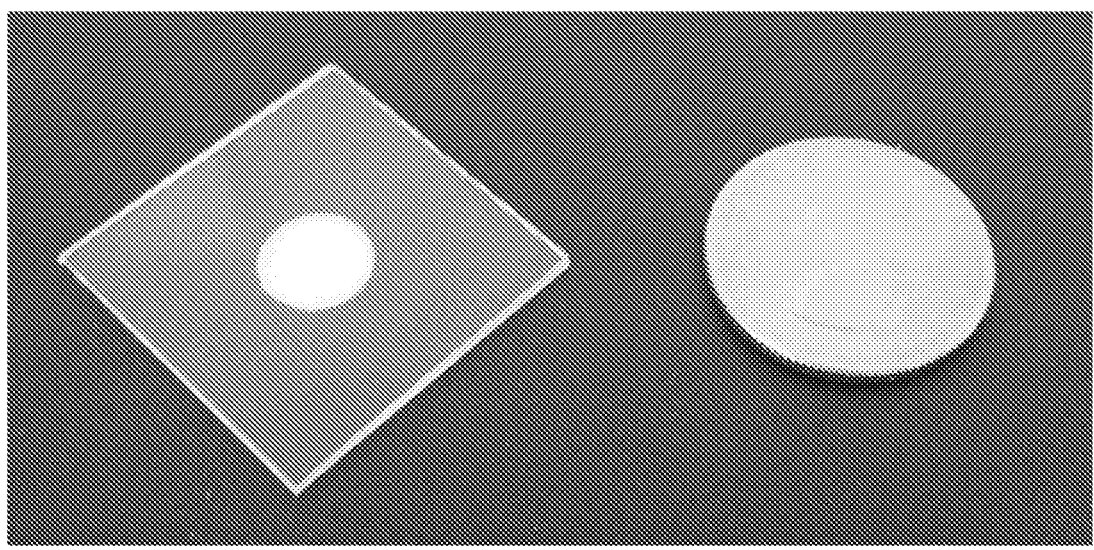
FIG. 22: Photograph of a COP reaction chamber-PES assembly, including a quarter for scale.
Figure 23:
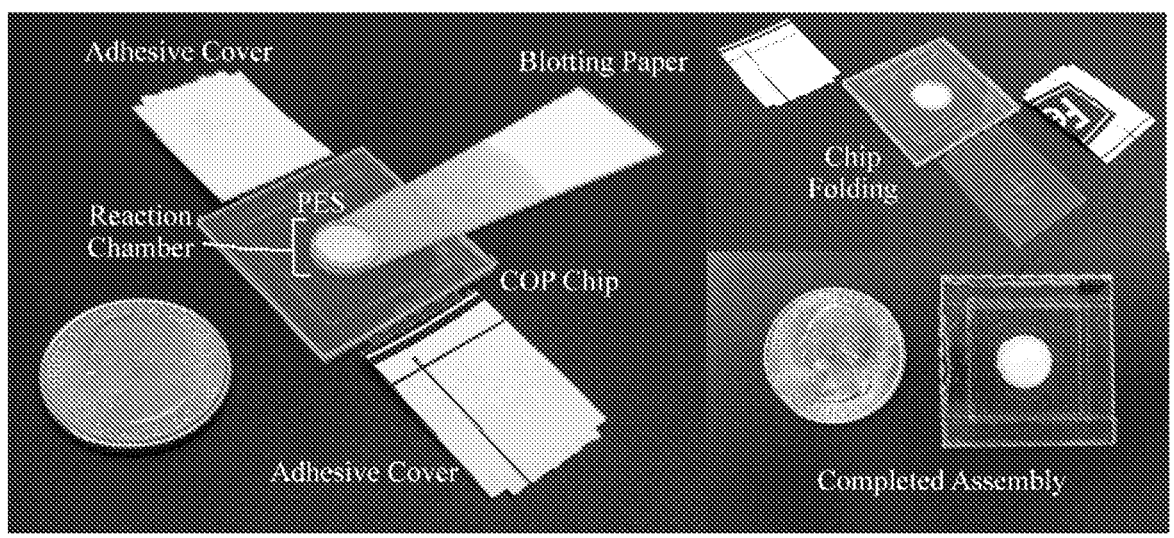
FIG. 23: Photograph of a reaction chamber only chip, including a COP reaction chamber-PES assembly including two adhesive covers and a blotting paper.

Pieces of PES can be inserted between layers of COP and held in place securely after layers of COP are annealed by hot pressing. COP sheets were cut into blanks with a cutting plotter (GraphTec CE6000-40) at the dimensions shown in FIG. 25. Circular cutouts were removed from the COP blanks. COP blanks were accordion folded along perforations. The folded COP blanks were briefly submerged in acetone to remove contaminants and allowed to air dry. The COP blanks were placed on a piece of Mylar and the PES pad was positioned by hand between the bottom two layers of the COP blank. Light pressure was applied to ensure that the PES pad did not become misaligned. The COP-PES constructs were sandwiched between two Mylar sheets and then between two metal plates. The metal plates were positioned appropriately in a heated press (Carver, hydraulic unit model #3912). The assembly was heated to 126° C. for 7 minutes at 240 kPa of pressure (0.2 metric tons applied per chip). The whole assembly was flipped over and heated again for 7 minutes at 126 C and 240 kPa. The assembly was removed from the press and allowed to cool. In the current implementation, a 9.5 mm diameter circular hole punch of PES was positioned concentrically with the 8.5 mm circular openings between the bottom two layers of accordion-folded COP. The resulting COP-PES assembly is shown in FIG. 22.

Precut adhesive film was then applied to the COP-PES assembly to form an HDA reaction chamber and attach additional components. FIGS. 23 and 24A-24C show a reaction chamber only design, i.e., wherein the waste region and detection region are not integrally attached and a design that integrates a lateral flow strip (LFS) and a removable waste pad, respectively. Both designs feature two reaction chamber lids composed of adhesive tape. Wax paper provided with the Fellowes adhesive is used to cover the lids until after sample has been applied to the chip.

Figures 24A, 24B, 24C:
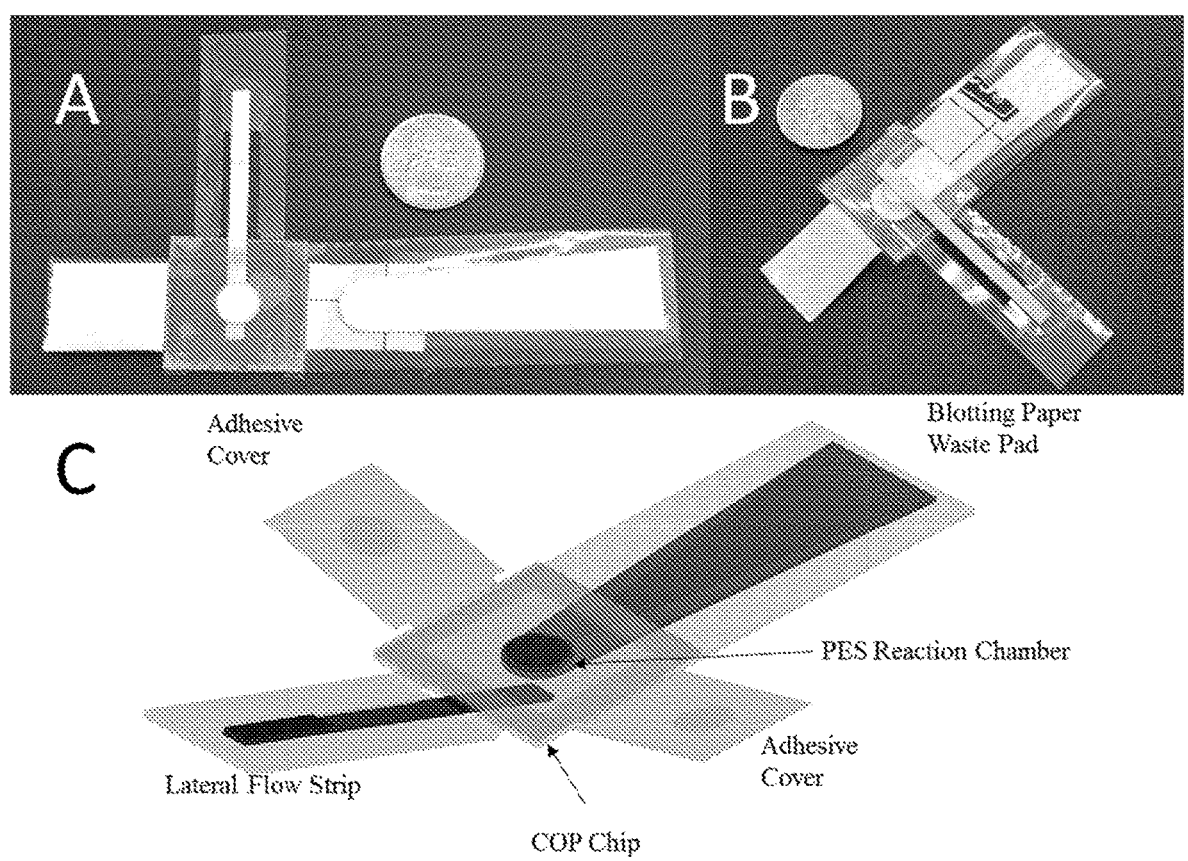
FIGS. 24A-24C. Full chip assembly with two adhesive covers. (a) Photograph of the chip in an unfolded configuration. The waste region is unfolded and out of contact with the capture region. (b) Photograph of the chip after the waste region has been folded across the chip to contact the capture region. The configuration in (b) is upside-down relative to (a). (c) Schematic of a different embodiment of a full chip assembly having two adhesive covers, wherein the waste region and the LFD are in parallel alignment.

In the full chip assembly, a 0.25 inch diameter circular punch out of blotting paper (Whatman GB003) placed between the PES pad and the waste pad has been included in the current design to expedite fluid flow through the PES membrane. This punch out is placed onto the PES pad prior to securing the waste pad to the COP-PES assembly via the four binding flaps (FIG. 24A). The waste pad, enclosed by adhesive tape, is folded such that the exposed waste pad comes into contact with the blotting paper. The four binding flaps are then folded over to secure the waste pad (FIG. 24B).

B. Adhesive Materials

This chip design utilizes a commercially available single-sided adhesive film (Fellowes Self-adhesive Sheets 3 mil cat. CRC52215) which forms both the adhesive lids and reaction chamber covers. The adhesive film additionally secures the COP/PES reaction chamber, the lateral flow strip, and waste pad in the proper alignment.

As an alternative to the Fellowes adhesive, PCR plate sealing film (TempPlate® RT Select Optical Film cat. 2921-7800, USA Scientific) has been examined. Reaction chambers containing only PES (original chip design, with no integrated LFS or waste-pad) were constructed with PCR plate sealing film substituted for the Fellowes brand adhesive. A helicase dependent amplification (HDA) reaction was performed in the chip (i.e. reaction volume was pipetted directly onto the PES pad) with $10^6$ copies of NG template DNA (30-minute incubation at 65° C., 35 mM NaCl). Amplification of product was not detected by polyacrylamide gel electrophoresis (4 µL HDA product) nor LFS (8 µL HDA product).

COP was examined as an alternative to Fellowes brand adhesive for the reaction chamber lid covers (such that COP lids were used to shield the reaction from the adhesive). 25 µL HDA reactions containing $10^6$ copies of DNA template were pipetted onto the PES pads contained within COP reaction chambers. Polyacrylamide gel electrophoresis was performed on 2 µL of HDA product from each replicate. Amplification between replicates exhibited binary behavior wherein either product of the expected size amplified robustly or no amplification was observed at all.

Example 5

Device and Variants Thereof

Figure 25:
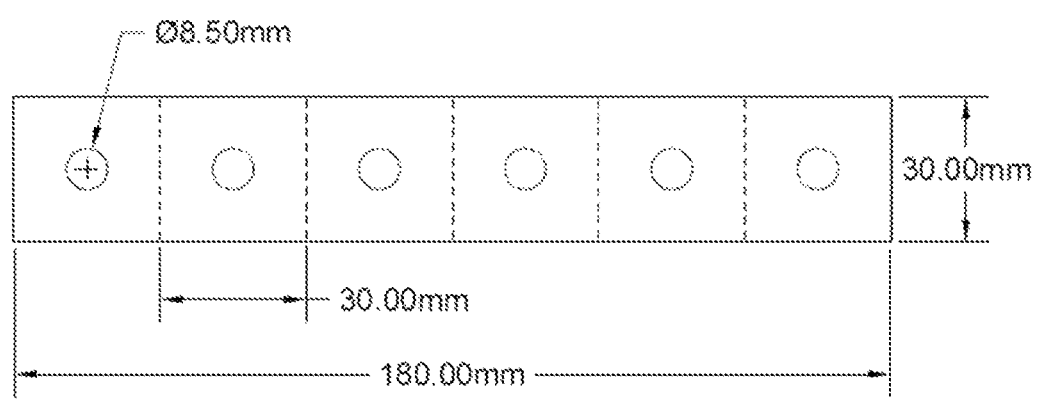
FIG. 25: Scheme for a cutout of a COP reaction chamber.

FIG. 25 shows a cutout of a COP reaction chamber. This component is designed to be accordion folded along the perforations such that the circular holes on each face are concentric when fully compressed. A circular piece of polyethersolfone (PES) with a diameter of 0.375 inches is positioned between two faces of the folded COP component, concentric with the circular holes on each face. When the layers of COP are annealed (via hot pressing) the PES is secured in position without the use of adhesives. The inclusion of a COP-PES reaction chamber in the chip improves HDA reaction efficiency by eliminating adhesive contact with the PES and by creating a chamber wherein the reaction can occur outside of the PES matrix.

Figure 26:
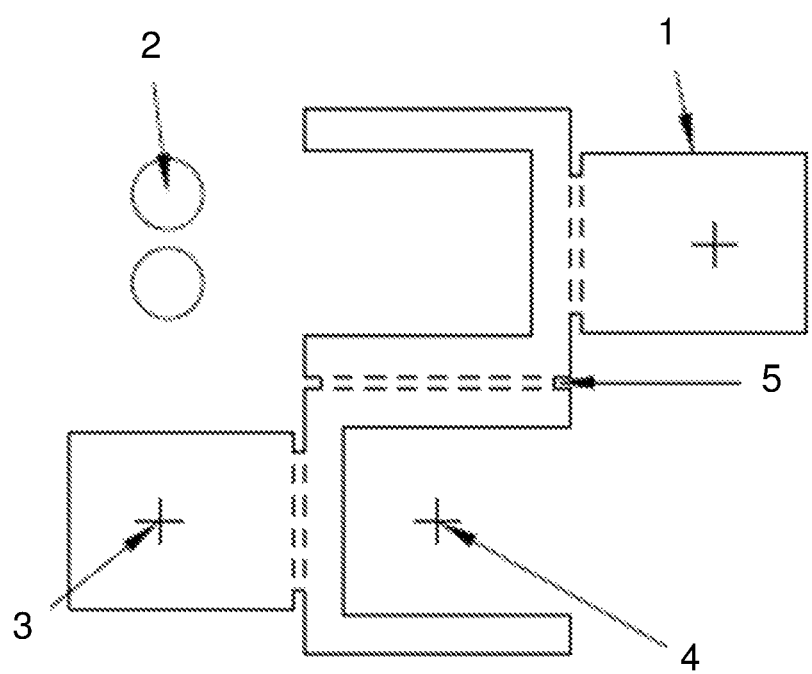
FIG. 26: Scheme for a cutout of an adhesive film housing without integrated waste pad or lateral flow strip. (1) Reaction chamber lid. The two reaction chamber lids included in this design can be folded over to seal the reaction chamber after the HDA reaction mixture has been added to the PES pad. This helps to maintain the integrity of the adhesive film when the lids are opened and closed. (2) Reaction chamber lid covers. Two lid covers made out of the adhesive material are placed onto the reaction chamber lids concentrically. (3) 'X' cut used to properly position the reaction chamber lid covers onto the reaction chamber lids. When the lid covers are placed concentrically with the 'X', they are aligned properly. (4) COP-PES component is positioned here such that the edges of the COP-PES component are flush with the outer edges of the adhesive component. (5) 1.15 mm offset between perforated lines allows the adhesive component to easily be folded over and adhere to both faces of the COP-PES component.

Adhesive components without integrated waste pad or lateral flow strip are shown in FIG. 26. This COP-PES holder is included in the full chip designs described hereafter. The key features are two "U" shaped adhesive components that secure the COP-PES when placed into contact with the top and bottom faces of the COP-PES component and two reaction chamber lids that can be used to seal the reaction chamber, e.g., prior to incubating a reaction.

Figure 27:
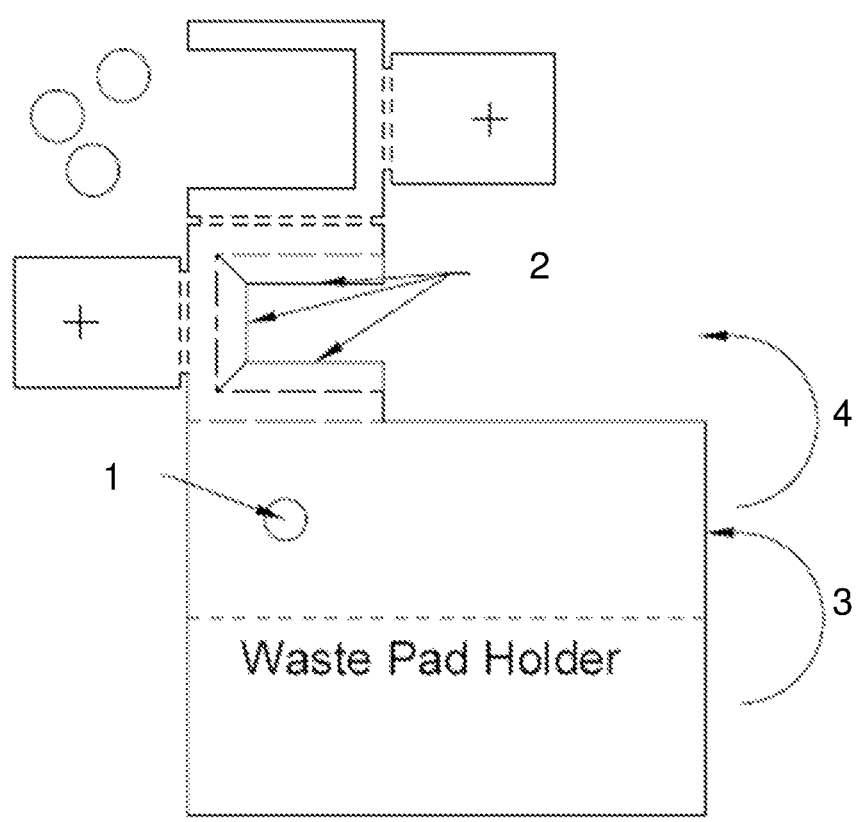
FIG. 27: Scheme for a cutout of one embodiment of an adhesive film housing including an integrated waste pad holder. (1) Insertion point for 0.25" transfer layer, e.g., blotting paper, circular punch which couples the PES pad to the waste pad. (2) Flaps folded 180 degrees to hold waste pad in position. (3) The waste pad placed in the waste pad holder, which is folded 180 degrees (adhesive sides face inward) along the perforation. (4) The now covered waste pad is folded 180 degrees such that the opening to the waste pad is facing the PES pad.

FIG. 27 shows a first embodiment of a chip design, including an integrated waste pad holder. The waste pad is contained between two layers of adhesive with both adhesive faces in contact with the waste pad. Three flaps under the lid are folded 180 degrees such that when the waste pad is brought into contact with the PES the adhesive flaps hold the waste pad in the appropriate position. This design choice circumvents the failure mode wherein the wetted waste pad tears into two parts during waste pad removal. This allowed for the insertion of a 0.25" blotting paper punch-out to maintain contact between the PES and the waste pad.

FIG. 28 shows a second embodiment of a chip design, including an integrated waste pad holder. The waste pad is repositioned relative to the COP-PES holding component. This design decreases the total amount of material that connects the waste pad to the rest of the adhesive components and accordingly makes waste pad removal (via tearing along the perforations) easier. Two adhesive flaps have been added to this design to secure the waste pad in position such that there are four points of contact between the waste pad and the reaction chamber holder.

FIG. 29 shows a third embodiment of a chip design, including an integrated waste pad holder and an integrated detection region (e.g., LFD) holder. This design uses flaps to hold the lateral waste pad in position, but two more have been added (attached to the waste pad holder directly) and the existing flaps have been repositioned. This results in 6 points of contact between the waste pad holder and the rest of the chip which provides additional stability and does not interfere with waste pad removal. Triangular flaps have been added to the reaction lids to create a pull tab for easy opening following the reaction, e.g., HDA reaction. This design incorporates a lateral flow strip (LFS) holder. A LFS is positioned such that the end of the loading pad rests in the center of the reaction chamber, and the holder is folded along the perforation sealing the LFS.

A further embodiment of a chip design is shown in FIG. 30. In this case, the circular opening to the waste pad has been enlarged to decrease contact by the adhesive with the PES. Additionally, the lateral flow strip holder has been opened on top and bottom to eliminate capillary action causing product to flow around the lateral flow strip (as opposed to through the lateral flow strip). In this design, only the waste pad attached to the LFD strip is fully encased in adhesive film.

Example 6

Detection of N. Gonorrhoeae DNA

Figure 31:
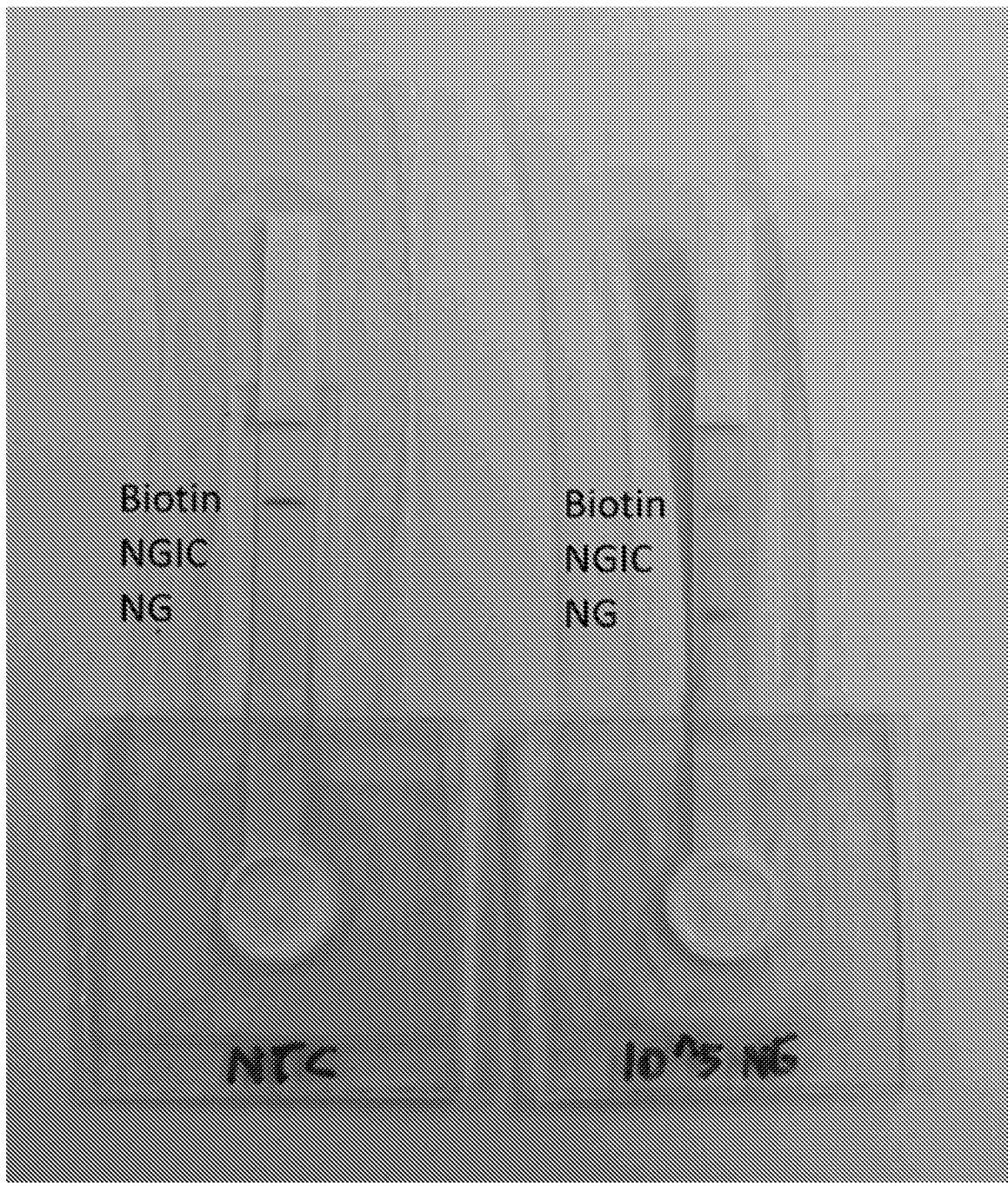
FIG. 31: Photograph of HDA on chip having $10^5$ copies of genomic N. gonorrhoeae DNA.

Example 6 provides a method of detecting N. gonorrhoeae (NG) DNA using a device having an integrated lateral flow strip. Results are shown in FIG. 31. A 15×15 cm piece of gel blotting paper (Whatman, cat. GB003) was cut in half. A 0.25" diameter circular hole punch was used to make 2 discs of blotting paper which were then placed on each piece of blotting paper to facilitate top-to-bottom wicking of fluid. A PES chip with an integrated lateral flow strip was placed onto each disc of blotting paper such that the PES and the blotting paper were concentric and the reaction chamber faced upwards. A positive control (genomic N. gonorrhoeae DNA; $2\times10^4$ genomes/uL) and a non-template control (nuclease free DI water) were examined. 5 µL of sample (either $10^5$ or 0 copies of genomic NG DNA) was mixed with 50 µL guanidinium thiocyanate (6 M), 6 µL sodium chloride (5 M), 3 µL GlycoBlue Coprecipitant (15 mg/mL; ThermoFisher Scientific) and 35 µL 1-butanol in a 200 µL PCR tube. The mixture was briefly vortexed, centrifuged, and added directly to the PES of the COP reaction chamber via pipette in 2 aliquots of 50 µL. Precipitation was visually observed via GlycolBlue staining of the PES. Next, the precipitated sample on the PES was washed with a series of ethanol washes. First, 200 µl of 70% EtOH was added manually in 4 aliquots of 50 µl, followed by 102 µL of 95% EtOH added in 3 aliquots of 34 µl. After washing, the chip was lifted up from the blotting paper, and the 0.25" blotting paper punch was gently separated from the PES using a pipette tip. The PES was allowed to dry for 10 minutes on a piece of blotting paper to evaporate any residual ethanol. Next, 25 µL of tHDA reaction mixture with spiked-in NGIC plasmid was added to the reaction chamber. User-manipulated tabs were used to seal the PES and tHDA mix at the top and bottom of the reaction chamber. The chips were incubated at 65° C. for 45 minutes on a heated press (Carver, hydraulic unit model #3912). After heating, the lid covering the top of the reaction chamber was removed and the lateral flow strip was placed in contact with the HDA solution. The lid was then resealed to secure the lateral flow strip in position. Next, the lid covering the bottom side of the reaction chamber was lifted. 50 µL of running buffer was added to the exposed PES pad allowing the HDA product to wick through the lateral flow strip for downstream visual detection. The photo of FIG. 31 was taken 10 minutes after adding the running buffer to the PES pad. The presence of a test line in the sample containing $10^5$ copies of NG DNA and the absence of a test line in the no template control demonstrates that this device can be used to precipitate DNA, use precipitated DNA as a template for in situ tHDA, and generate a colorimetric readout indicating the presence or absence of target DNA.

Example 7

Method of Folding an Exemplary Chip

This example provides a an exemplary step-by-step protocol for folding a chip having two reaction chamber lids, an integrated waste region, and an integrated LFD strip, such as that including an adhesive film as shown in FIG. 30 (adhesive side down). The following method of folding can be readily applied to any of the detection processes described herein (e.g., LAMP reactions, multiplexed reactions). The terms outward and inward, as used below, refer to the direction relative to the top view shown in FIG. 30. The method proceeds as follows:

1. Fold A outward to encapsulate a waste pad.
2. Fold each flap B outward to stabilize the fold performed in step 1.
3. Fold C outward to encapsulate a LFD strip.
4. Place a COP reaction chamber, including a PES capture region supported therewithin, such that upon outward folding of D, the reaction chamber is sandwiched within the housing and the PES capture region is exposed on both sides.
5. Fold each flap E outward to stabilize the fold performed in step 4.
6. Fold F inward to contact the PES capture region with the waste pad (through the circular opening of the waste pad holder).
7. Add sample and reagent to the PES capture region.
8. Fold G outward to close the top reaction chamber lid and incubate.
9. Unfold G to open the top reaction chamber lid.
10. Add wash buffer to the PES capture region. The wash buffer and waste will wick into the waste pad below.
11. Unfold F and tear at F to remove the waste region from the chip.
12. Fold H outward to close the bottom reaction chamber lid.
13. Add elution buffer to the PES capture region from the top.
14. Remove the adhesive tab separating the LFD strip from the PES capture region to allow detection to occur.

Example 8

Multiplexed HPV 16 and 18 LAMP

Figure 32:
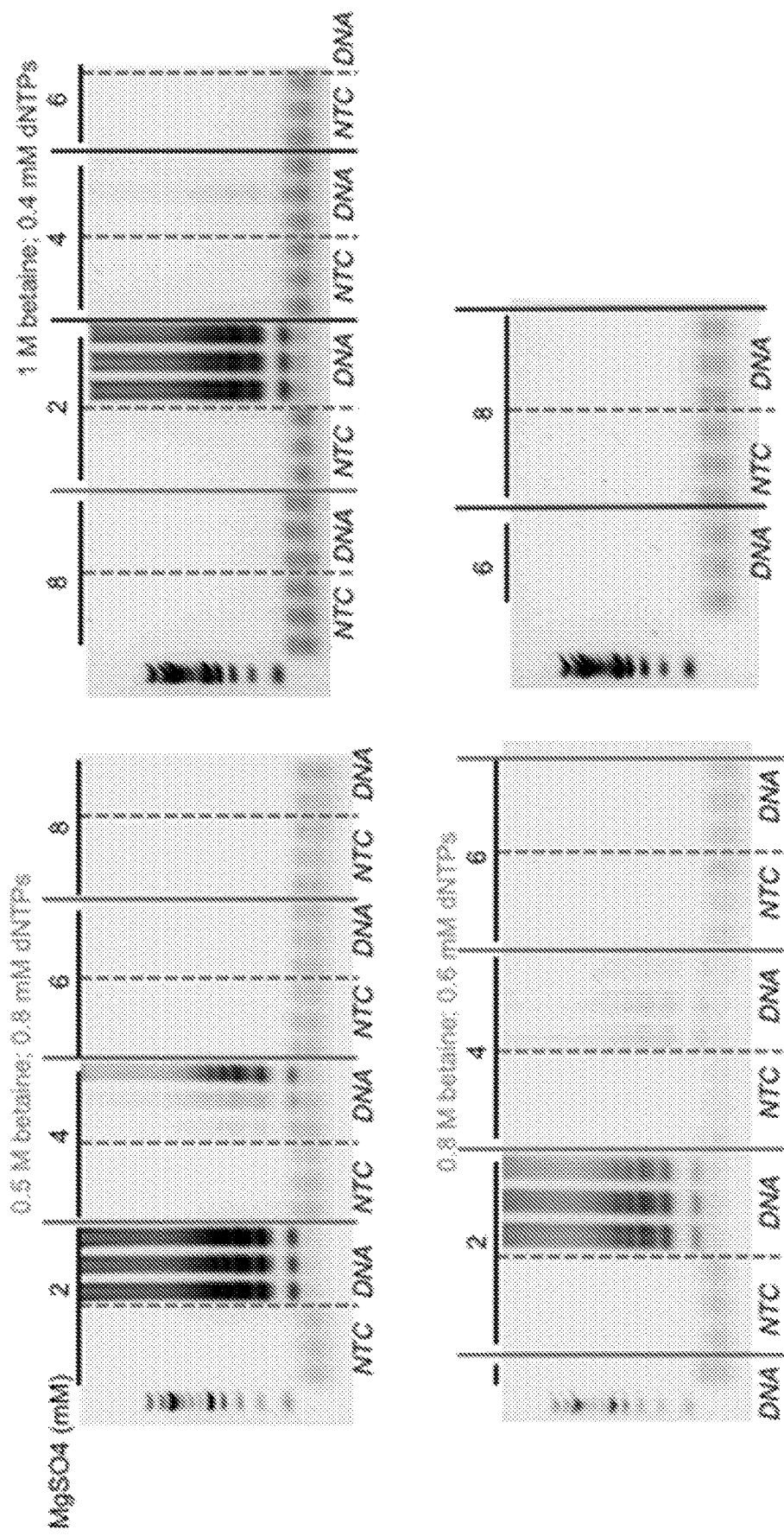
FIG. 32: Image showing HPV 18 LAMP optimization for 30 minutes by varying betaine, dNTPs, and $MgSO_4$ concentrations. To achieve amplification in 30 minutes, the HPV18 LAMP assay required double the original dNTP concentration but the same concentrations of betaine and $MgSO_4$ (condition 1-0.5 M betaine, 0.8 mM dNTPs, 2 mM $MgSO_4$).

Multiplexed LAMP (mLAMP) was achieved by first optimizing the HPV 16 and HPV 18 singleplex assays for a reaction time of 30 minutes. The singleplex HPV 16 LAMP assay was originally optimized for 30 minutes, while the singleplex HPV 18 LAMP assay was originally optimized for 60 minutes. Therefore, the optimization for reaction time focused on reducing the HPV 18 LAMP assay to 30 minutes without compromising amplification efficiency. Different concentrations of dNTPs (0.4-1 mM), betaine (0.5-1 M), and $MgSO_4$ (2-8 mM) were tested (FIG. 32). Conditions yielding positive amplification were (1) 0.5 M betaine, 0.8 mM dNTPs, 2 mM $MgSO_4$; (2) 0.5 M betaine, 0.8 mM dNTPs, 4 mM $MgSO_4$; (3) 0.8 M betaine, 0.6 mM dNTPs, 2 mM $MgSO_4$; and (4) 1 M betaine, 0.4 mM dNTPs, 2 mM $MgSO_4$. These 4 conditions were repeated and found to achieve amplification in 30 minutes. The HPV18 LAMP assay required double the original dNTP concentration but the same concentrations of betaine and $MgSO_4$ (Condition 1).

Figure 33:
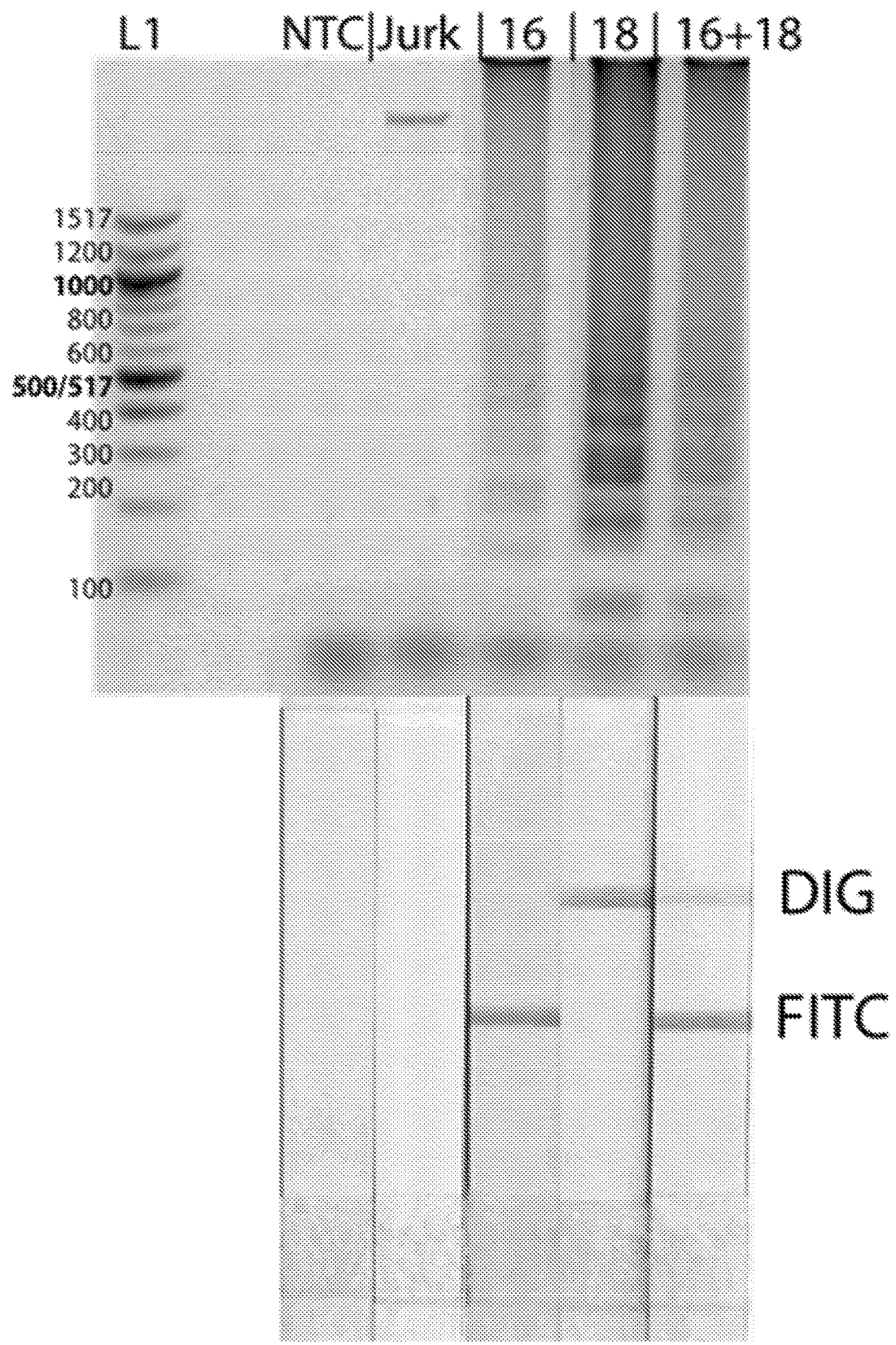
FIG. 33: Images of multiplexed HPV 16 and 18 LAMP in tube at 63° C. for 30 minutes and differential detection on lateral flow strips. HPV 16 LAMP was tagged with FITC and HPV 18 LAMP was tagged with digoxigenin (DIG) L1=New England Biolabs (NEB) 100 bp ladder. 16=HPV 16 DNA, $10^5$ copies. 18=HPV 18 DNA, $10^5$ copies. 16+18=HPV 16 and HPV 18 DNA, $10^5$ copies. NTC=no template control (water). Jurk=100 ng Jurkat cell DNA.

After each assay was optimized for 30 minutes, a 1:1 ratio of each assay was used in the final multiplexed reaction, as is commonly employed in the literature for mLAMP assays. If this did not yield successful amplification, then different ratios would have been tested to account for the variability in amplification efficiency between assays. LAMP primers for each HPV were tagged with probes that could be detected on an agarose gel and lateral flow strip (LFS) (FIG. 33). HPV 16 was tagged with fluorescein isothiocyanate (FITC) and HPV 18 was tagged with digoxigenin (DIG). The LFS has lines for anti-FITC and anti-DIG. Jurkat cell DNA was used as a genomic DNA negative control. The lower limit of detection of the tube assay is currently $10^5$ cp.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and can be applied to the essential features hereinbefore set forth, and follows in the scope of the claims.

Other embodiments are in the claims.

What is claimed is:

1. A detection device, the device comprising:
   (a) a capture region for binding a target in a sample;
   (b) a waste region connected to the capture region, wherein the waste region can absorb a non-target fraction of the sample, wherein the waste region can be disconnected from the capture region by folding or tearing;
   (c) a detection region separated from the capture region by a removable tab that prevents transfer of liquid from the capture region to the detection region; and
   (d) a non-absorbent housing that prevents moisture transfer,
   wherein the housing comprises a film, and wherein the film is perforated for tearing.

2. The device of claim 1, wherein the removable tab can be disconnected from the device by tearing.

3. The device of claim 1, further comprising a protective flap connected to the housing that can be folded onto the capture region to prevent moisture loss.

4. The device of claim 3, wherein the film comprises the protective flap.

5. The device of claim 1, wherein the removable tab and the housing are connected and cut from a single planar sheet of film.

6. The device of claim 1, wherein the waste region comprises cellulose.

7. The device of claim 1, wherein the detection region comprises a lateral flow detection strip; the detection region comprises one or more detection probes; and/or the detection region comprises one or more visible particles or detection antibodies.

8. The device of claim 1, wherein a portion of the housing in contact with the capture region comprises cyclo olefin polymer (COP) and/or a transfer layer is sandwiched between the capture region and the waste region, the transfer layer configured to wick fluid into the waste region.

9. The device of claim 1, wherein the capture region comprises a polyethersulfone (PES) membrane.

10. The device of claim 1, wherein the capture region is impregnated with one or more isothermal nucleic acid amplification reagents.

11. The device of claim 10, wherein the isothermal nucleic acid amplification reagents comprise reagents for loop-mediated isothermal amplification (LAMP), helicase dependent amplification (HDA), rolling circle amplification (RCA), multiple displacement amplification (MDA), recombinase polymerase amplification (RPA), or nucleic acid sequence base amplification (NASBA).

12. The device of claim 1, wherein the film comprises the removable tab.

13. A method for detecting the presence or absence of at least one target in a sample, the method comprising:
  (a) providing the device of claim 1;
  (b) applying a sample to the capture region, wherein the sample comprises the target and a non-target fraction, and wherein the target binds to the capture region and the non-target fraction wicks into the waste region;
  (c) eluting the target from the capture region to the detection region; and
  (d) detecting the presence of the target in the detection region.

14. The method of claim 13, wherein the target comprises a nucleic acid.

15. The method of claim 14, wherein step (b) further comprises isothermal nucleic acid amplification.

16. The method of claim 15, wherein the isothermal nucleic acid amplification comprises loop-mediated isothermal amplification (LAMP), helicase dependent amplification (HDA), rolling circle amplification (RCA), multiple displacement amplification (MDA), recombinase polymerase amplification (RPA), or nucleic acid sequence base amplification (NASBA).

17. The method of claim 13, wherein the capture region comprises polyethersulfone (PES) or the capture region is impregnated with one or more isothermal nucleic acid amplification reagents.

18. The method of claim 13, wherein step (c) comprises disconnecting the removable tab.

19. The method of claim 13, further comprising applying a liquid buffer to the capture region.

20. The method of claim 13, further comprising heating the capture region.

21. The method of claim 20, wherein the heating brings the capture region to a temperature of between 30° C. and 80° C.

22. The method of claim 21, wherein the temperature is about 65° C.

23. The method of claim 20, wherein the heating is provided by a heat block, a battery-powered heater, a thin-film heater, or a disposable exothermic heat pack.

24. A method of constructing the device of claim 1, the method comprising:
  (a) providing the capture region, the waste region, and the detection region;
  (b) folding a thin sheet to cover more than 50% of the surface area of the detection region to produce the housing.

* * * * *